(12) United States Patent
Diwu et al.

(10) Patent No.: US 9,012,643 B2
(45) Date of Patent: Apr. 21, 2015

(54) HYDROXAMATE SUBSTITUTED AZAINDOLINE-CYANINE DYES AND BIOCONJUGATES OF THE SAME

(71) Applicant: Becton, Dickinson and Company, Franklin Lakes, NJ (US)

(72) Inventors: Zhenjun Diwu, Sunnyvale, CA (US); Haitao Guo, Santa Clara, CA (US); Xing Han, San Jose, CA (US); Mirion Schultz, San Jose, CA (US); Timothy Dubrovsky, Davis, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 14/061,670

(22) Filed: Oct. 23, 2013

(65) Prior Publication Data
US 2014/0127717 A1    May 8, 2014

Related U.S. Application Data

(60) Provisional application No. 61/717,983, filed on Oct. 24, 2012.

(51) Int. Cl.
| | |
|---|---|
| *C07D 491/02* | (2006.01) |
| *G01N 33/567* | (2006.01) |
| *G01N 33/58* | (2006.01) |
| *C09B 23/01* | (2006.01) |
| *C09B 23/06* | (2006.01) |
| *C09B 23/08* | (2006.01) |

(52) U.S. Cl.
CPC .......... *G01N 33/582* (2013.01); *C09B 23/0025* (2013.01); *C09B 23/0066* (2013.01); *C09B 23/06* (2013.01); *C09B 23/083* (2013.01); *C09B 23/086* (2013.01)

(58) Field of Classification Search
None
See application file for complete search history.

(56) References Cited

U.S. PATENT DOCUMENTS

| | | | |
|---|---|---|---|
| 5,714,386 A | 2/1998 | Roederer | |
| 5,767,287 A | 6/1998 | Bobrow et al. | |
| 6,008,373 A | 12/1999 | Waggoner et al. | |
| 6,217,848 B1 | 4/2001 | Achilefu et al. | |
| 6,534,041 B1 | 3/2003 | Licha et al. | |
| 6,673,943 B2 | 1/2004 | Waggoner et al. | |
| 7,087,744 B2 | 8/2006 | Nishigaki et al. | |
| 7,465,810 B2 | 12/2008 | Diwu et al. | |
| 7,510,700 B2 | 3/2009 | Achilefu et al. | |
| 7,790,893 B2 | 9/2010 | Leung et al. | |
| 7,910,753 B2 | 3/2011 | Diwu et al. | |
| 8,431,416 B2 | 4/2013 | Diwu et al. | |
| 2003/0165918 A1 | 9/2003 | Nakamura et al. | |
| 2009/0258385 A1 | 10/2009 | Letestu et al. | |
| 2009/0305410 A1 | 12/2009 | Mao et al. | |
| 2010/0151493 A1 | 6/2010 | Wolfers et al. | |
| 2010/0255504 A1 | 10/2010 | Diwu et al. | |
| 2011/0008785 A1 | 1/2011 | Tan et al. | |
| 2011/0262898 A1 | 10/2011 | Dong et al. | |
| 2012/0035346 A1 | 2/2012 | Terpetschnig et al. | |
| 2012/0183954 A1 | 7/2012 | Diwu et al. | |

FOREIGN PATENT DOCUMENTS

| | | |
|---|---|---|
| WO | 0102374 A1 | 1/2001 |
| WO | 2012054749 A1 | 4/2012 |
| WO | 2012054784 A1 | 4/2012 |
| WO | 2012129128 A1 | 9/2012 |

OTHER PUBLICATIONS

Goncalves, "Fluorescent Labeling of Biomolecules with Organic Probes", Chemical Reviews, vol. 109, No. 1, pp. 190-212 (2009).

*Primary Examiner* — Nyeemah A Grazier
(74) *Attorney, Agent, or Firm* — Glenn J. Foulds; Bret E. Field; Bozicevic, Field & Francis LLP

(57) ABSTRACT

Hydroxamate substituted azaindoline cyanine dyes, conjugates thereof and methods of using the same are provided. The subject cyanine dyes include an azaindoline ring having a hydroxamate substituent. The dyes may further include a reactive group moieties (RGM) and/or a water soluble group. Also provided are conjugates of the subject dyes. Also provided are tandem conjugates including a fluorescent protein capable of energy transfer to the dye. Methods of detecting an analyte in a sample by contacting the sample with a detection reagent are provided. The detection agent may be a dye-conjugate that specifically binds the analyte, or may be a reactive dye which conjugates to the analyte. Also provided are compositions, e.g., kits, etc., incorporating such dyes which facilitate use in such methods.

19 Claims, 13 Drawing Sheets

US 9,012,643 B2
1

HYDROXAMATE SUBSTITUTED AZAINDOLINE-CYANINE DYES AND BIOCONJUGATES OF THE SAME

CROSS-REFERENCE TO RELATED APPLICATIONS

Pursuant to 35 U.S.C. §119 (e), this application claims priority to the filing date of the U.S. Provisional Patent Application Ser. No. 61/717,983, filed Oct. 24, 2012, the disclosure of which is incorporated herein by reference.

INTRODUCTION

Fluorescent probes are valuable tools for biological detections in a number of applications, including histology, cytology and immunology applications. Specifically, fluorescent probes find utility in the identification and separation of subpopulations of cells in a mixture of cells by flow cytometry, fluorescence-activated cell sorting and fluorescence microscopy; determination of the concentration of binding moieties (e.g., antigen-antibody binding) in fluorescence immunoassays; localization of substances in gels or other supports by staining. Fluorescent compounds may be covalently or non-covalently attached to other materials to impart fluorescence. Brightly fluorescent dyes permit detection or location of the attached materials with great sensitivity.

When employing fluorescent dyes for the above purposes, there are many considerations on the choice of the fluorescent dye. One consideration is the absorption and emission characteristics of the fluorescent dye, since many ligands, receptors, and materials in the sample under test, e.g. blood, urine, cerebrospinal fluid, will fluoresce and interfere with an accurate determination of the fluorescence of the fluorescent label. This phenomenon is called autofluorescence or background fluorescence. Another consideration is the ability to conjugate the fluorescent dye to ligands and receptors and other biological and non-biological materials and potential effects of such conjugation on the properties of the molecules, such as changes in quantum efficiency of the fluorescent dye. It is also possible that conjugation with the fluorescent dye will inactivate the function of the molecule that is labeled. A third consideration is the quantum efficiency of the fluorescent dye which should be high for sensitive detection. A fourth consideration is the light absorbing capability, or extinction coefficient, of the fluorescent dye, which should also be as large as possible. Also of interest is whether the fluorescent molecules will interact with each other when in close proximity, resulting in self-quenching. A fifth consideration is the photostability of the labeling dye since dye conjugates are often subject to repeated irradiation for optimal detection. An additional consideration is whether there is non-specific binding of the fluorescent dye to other compounds or container walls, either by itself or in conjunction with the compound to which the fluorescent dye is conjugated.

Therefore, fluorescent dyes and conjugates that have one or more properties such as high quantum efficiency, good photostability, absorption and emission at longer wavelengths, higher conjugation yield, low nonspecific interference, low quenching and low self-aggregation, are of interest.

SUMMARY

Hydroxamate substituted azaindoline cyanine dyes, bioconjugates thereof and methods of using the same are provided. The subject dyes include a cyanine dye structure having an azaindoline ring, where a pyridium moiety is incorporated into an indoline ring structure to form the azaindoline ring, and a hydroxamate moiety is attached to the azaindoline ring as a substituent. In some cases, the hydroxamate moiety is incorporated at position 5 of the azaindoline ring. The dyes further includes a reactive group moiety (RGM) at one or more of a variety of positions.

Aspects of the invention include reactive hydroxamate substituted azaindoline cyanine dyes and their conjugates, where a subject dye is conjugated to a substrate of interest. In some cases, the substrate includes a binding moiety that specifically binds to an analyte of interest. In certain cases, the dye-conjugate is a tandem conjugate where the dye is conjugated to a fluorescent protein. The dye may be capable of FRET with the conjugated fluorescent protein. The dye-fluorescent protein conjugate may be further conjugated to a binding moiety that specifically binds to an analyte of interest.

Methods of detecting an analyte in a sample are provided. Aspects of the method include contacting the sample with a detection reagent. In some cases, the detection agent is a dye conjugate that includes a specific binding moiety, which specifically binds the analyte. In some cases, the detection agent is a reactive dye, which conjugates to the analyte. Aspects of the method further include detecting the analyte by fluorescence. The dye compounds and dye conjugates find use in locating or detecting the interaction or presence of analytes or ligands in a sample. Also provided are compositions, e.g., kits, etc., incorporating such dyes or dye conjugates facilitate their use in such methods.

DEFINITIONS

Figure 1:
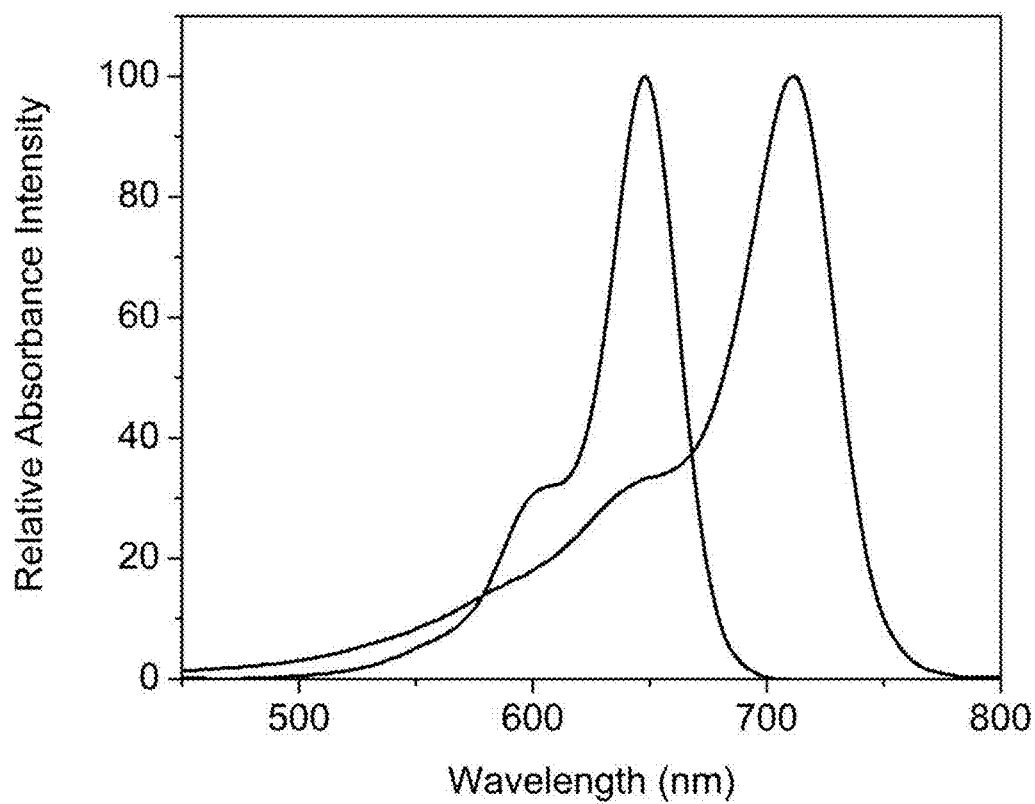
FIG. 1 shows absorption spectra of Compound 26 (right) and Cy5 (left) in PBS buffer (pH=7.4). The absorption maximum wavelength of the Compound 26 is red-shifted by ~63 nm compared to Cy5.
Figure 2:
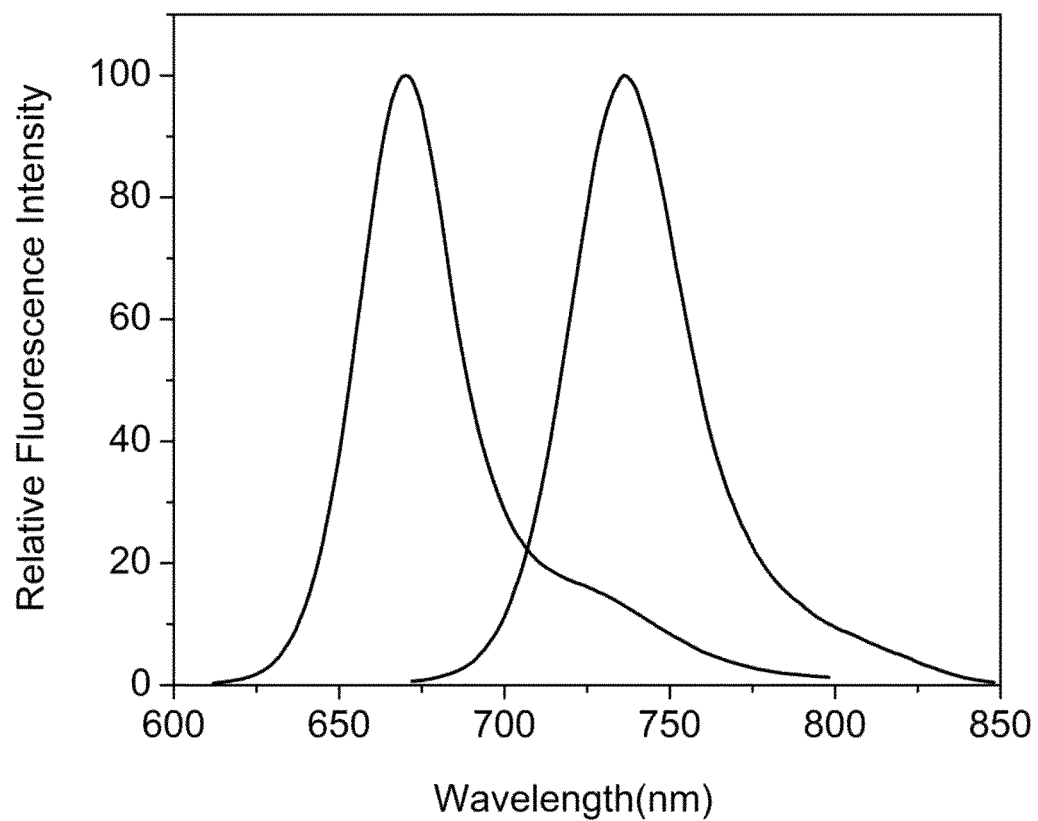
FIG. 2 shows fluorescence spectra of Compound 26 (right) and Cy5 (left) in PBS buffer (pH=7.4, excited at 630 nm). The fluorescence maximum wavelength of the Compound 26 is red-shifted by ~66 nm compared to Cy5.

The following terms have the following meanings unless otherwise indicated. Any undefined terms have their art recognized meanings.

"Alkyl" refers to monovalent saturated aliphatic hydrocarbyl groups having from 1 to 10 carbon atoms and such as 1 to 6 carbon atoms, or 1 to 5, or 1 to 4, or 1 to 3 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

The term "substituted alkyl" refers to an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R' and R" may be the same or different and are chosen from hydrogen, optionally substituted alkyl, cycloalkyl, alkenyl, cycloalkenyl, alkynyl, aryl, heteroaryl and heterocyclic.

"Alkylene" refers to divalent aliphatic hydrocarbyl groups preferably having from 1 to 6 and more preferably 1 to 3 carbon atoms that are either straight-chained or branched, and which are optionally interrupted with one or more groups selected from —O—, —NR$^{10}$—, —NR$^{10}$C(O)—, —C(O)NR$^{10}$— and the like. This term includes, by way of example, methylene (—CH$_2$—), ethylene (—CH$_2$CH$_2$—), n-propylene (—CH$_2$CH$_2$CH$_2$—), iso-propylene (—CH$_2$CH(CH$_3$)—), (—C(CH$_3$)$_2$CH$_2$CH$_2$—), (—C(CH$_3$)$_2$CH$_2$C(O)—), (—C(CH$_3$)$_2$CH$_2$C(O)NH—), (—CH(CH$_3$)CH$_2$—), and the like.

"Substituted alkylene" refers to an alkylene group having from 1 to 3 hydrogens replaced with substituents as described for carbons in the definition of "substituted" below.

The term "alkane" refers to alkyl group and alkylene group, as defined herein.

The term "alkylaminoalkyl", "alkylaminoalkenyl" and "alkylaminoalkynyl" refers to the groups R'NHR"— where R' is alkyl group as defined herein and R" is alkylene, alkenylene or alkynylene group as defined herein.

The term "alkaryl" or "aralkyl" refers to the groups -alkylene-aryl and -substituted alkylene-aryl where alkylene, substituted alkylene and aryl are defined herein.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkoxyamino" refers to the group —NH-alkoxy, wherein alkoxy is defined herein.

The term "haloalkoxy" refers to the groups alkyl-O— wherein one or more hydrogen atoms on the alkyl group have been substituted with a halo group and include, by way of examples, groups such as trifluoromethoxy, and the like.

The term "haloalkyl" refers to a substituted alkyl group as described above, wherein one or more hydrogen atoms on the alkyl group have been substituted with a halo group. Examples of such groups include, without limitation, fluoroalkyl groups, such as trifluoromethyl, difluoromethyl, trifluoroethyl and the like.

The term "alkylalkoxy" refers to the groups -alkylene-O-alkyl, alkylene-O-substituted alkyl, substituted alkylene-O-alkyl, and substituted alkylene-O-substituted alkyl wherein alkyl, substituted alkyl, alkylene and substituted alkylene are as defined herein.

The term "alkylthioalkoxy" refers to the group -alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein.

"Alkenyl" refers to straight chain or branched hydrocarbyl groups having from 2 to 6 carbon atoms and preferably 2 to 4 carbon atoms and having at least 1 and preferably from 1 to 2 sites of double bond unsaturation. This term includes, by way of example, bi-vinyl, allyl, and but-3-en-1-yl. Included within this term are the cis and trans isomers or mixtures of these isomers.

The term "substituted alkenyl" refers to an alkenyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Alkynyl" refers to straight or branched monovalent hydrocarbyl groups having from 2 to 6 carbon atoms and preferably 2 to 3 carbon atoms and having at least 1 and preferably from 1 to 2 sites of triple bond unsaturation. Examples of such alkynyl groups include acetylenyl (—C≡CH), and propargyl (—CH$_2$C≡CH).

The term "substituted alkynyl" refers to an alkynyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl, and —$SO_2$-heteroaryl.

"Alkynyloxy" refers to the group —O-alkynyl, wherein alkynyl is as defined herein. Alkynyloxy includes, by way of example, ethynyloxy, propynyloxy, and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group $CH_3C(O)$—

"Acylamino" refers to the groups —$NR^{20}C(O)$alkyl, —$NR^{20}C(O)$substituted alkyl, $NR^{20}C(O)$cycloalkyl, —$NR^{20}C(O)$substituted cycloalkyl, —$NR^{20}C(O)$cycloalkenyl, —$NR^{20}C(O)$substituted cycloalkenyl, —$NR^{20}C(O)$alkenyl, —$NR^{20}C(O)$substituted alkenyl, —$NR^{20}C(O)$alkynyl, —$NR^{20}C(O)$substituted alkynyl, —$NR^{20}C(O)$aryl, —$NR^{20}C(O)$substituted aryl, —$NR^{20}C(O)$heteroaryl, —$NR^{20}C(O)$substituted heteroaryl, —$NR^{20}C(O)$heterocyclic, and —$NR^{20}C(O)$substituted heterocyclic, wherein $R^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyl" or the term "aminoacyl" refers to the group —$C(O)NR^{21}R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group —$NR^{21}C(O)NR^{22}R^{23}$ where $R^{21}$, $R^{22}$, and $R^{23}$ are independently selected from hydrogen, alkyl, aryl or cycloalkyl, or where two R groups are joined to form a heterocyclyl group.

The term "alkoxycarbonylamino" refers to the group —NRC(O)OR where each R is independently hydrogen, alkyl, substituted alkyl, aryl, heteroaryl, or heterocyclyl wherein alkyl, substituted alkyl, aryl, heteroaryl, and heterocyclyl are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclyl-C(O)O— wherein alkyl, substituted alkyl, cycloalkyl, substituted cycloalkyl, aryl, heteroaryl, and heterocyclyl are as defined herein.

"Aminosulfonyl" refers to the group —$SO_2NR^{21}R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic and where $R^{21}$ and $R^{22}$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Sulfonylamino" refers to the group —$NR^{21}SO_2R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the atoms bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 18 carbon atoms having a single ring (such as is present in a phenyl group) or a ring system having multiple condensed rings (examples of such aromatic ring systems include naphthyl, anthryl and indanyl) which condensed rings may or may not be aromatic, provided that the point of attachment is through an atom of an aromatic ring. This term includes, by way of example, phenyl and naphthyl. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —$SO_2$-alkyl, —$SO_2$-substituted alkyl, —$SO_2$-aryl, —$SO_2$-heteroaryl and trihalomethyl.

"Aryloxy" refers to the group —O-aryl, wherein aryl is as defined herein, including, by way of example, phenoxy, naphthoxy, and the like, including optionally substituted aryl groups as also defined herein.

"Amino" refers to the group —$NH_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

The term "azido" refers to the group —$N_3$.

"Carboxyl," "carboxy" or "carboxylate" refers to —$CO_2H$ or salts thereof.

"Carboxyl ester" or "carboxy ester" or the terms "carboxyalkyl" or "carboxylalkyl" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" or "carbonate" refers to the groups —O—C(O)O-alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" or "nitrile" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl.

"Cycloalkenyl" refers to non-aromatic cyclic alkyl groups of from 3 to 10 carbon atoms having single or multiple rings and having at least one double bond and preferably from 1 to 2 double bonds.

The term "substituted cycloalkenyl" refers to cycloalkenyl groups having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl.

"Cycloalkynyl" refers to non-aromatic cycloalkyl groups of from 5 to 10 carbon atoms having single or multiple rings and having at least one triple bond.

"Cycloalkoxy" refers to —O-cycloalkyl.

"Cycloalkenyloxy" refers to —O-cycloalkenyl.

"Halo" or "halogen" refers to fluoro, chloro, bromo, and iodo.

"Hydroxy" or "hydroxyl" refers to the group —OH.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic and at least one ring within the ring system is aromatic, provided that the point of attachment is through an atom of an aromatic ring. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl, and trihalomethyl.

In certain embodiments, any aryl or heteroaryl ring system may be unsubstituted or optionally and independently substituted by any synthetically accessible and chemically stable combination of substituents, such as H, halogen, cyano, sulfo, alkali or ammonium salt of sulfo, nitro, carboxy, alkyl, perfluoroalkyl, alkoxy, alkylthio, amino, monoalkylamino, dialkylamino or alkylamido, the alkyl portions of which having 18 or fewer carbons.

The term "heteroaralkyl" refers to the groups -alkylene-heteroaryl where alkylene and heteroaryl are defined herein. This term includes, by way of example, pyridylmethyl, pyridylethyl, indolylmethyl, and the like.

"Heteroaryloxy" refers to —O-heteroaryl.

The term "heteroatom", as used herein, by itself or as part of another group, means an oxygen atom ("O"), a sulfur atom ("S") or a nitrogen atom ("N"). It will be recognized that when the heteroatom is nitrogen, it may form an $NR_1R_2$ moiety, where $R_1$ and $R_2$ are, independently from one another, hydrogen or alkyl, or together with the nitrogen to which they are bound, form a saturated or unsaturated 5-, 6-, or 7-membered ring.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 20 ring atoms (such as from 5 to 14 ring atoms), including 1 to 10 hetero atoms (such as 1, 2, 3 or 4 oxygen, nitrogen or sulfur heteroatoms). These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$— moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Examples of heterocycle groups include thienyl, benzo[b]thienyl, naphtho[2,3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, carbazolyl, phenanthridinyl, acridinyl, perimidinyl, phenanthrolinyl, phenazinyl, isothiazolyl, phenothiazinyl, isoxazolyl, furazanyl, phenoxazinyl, and tetrazolyl groups).

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

"Heterocyclyloxy" refers to the group —O-heterocyclyl.

The term "heterocyclylthio" refers to the group heterocyclic-S—.

The term "heterocyclene" refers to the diradical group formed from a heterocycle, as defined herein.

The term "hydroxyamino" refers to the group —NHOH.

"Nitro" refers to the group —NO$_2$.

"Oxo" refers to the atom (═O).

"Sulfonyl" refers to the group SO$_2$-alkyl, SO$_2$-substituted alkyl, SO$_2$-alkenyl, SO$_2$-substituted alkenyl, SO$_2$-cycloalkyl, SO$_2$-substituted cylcoalkyl, SO$_2$-cycloalkenyl, SO$_2$-substituted cylcoalkenyl, SO$_2$-aryl, SO$_2$-substituted aryl, SO$_2$-heteroaryl, SO$_2$-substituted heteroaryl, SO$_2$-heterocyclic, and SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-SO$_2$—, phenyl-SO$_2$—, and 4-methylphenyl-SO$_2$—.

"Sulfonyloxy" refers to the group —OSO$_2$-alkyl, OSO$_2$-substituted alkyl, OSO$_2$-alkenyl, OSO$_2$-substituted alkenyl, OSO$_2$-cycloalkyl, OSO$_2$-substituted cylcoalkyl, OSO$_2$-cycloalkenyl, OSO$_2$-substituted cylcoalkenyl, OSO$_2$-aryl, OSO$_2$-substituted aryl, OSO$_2$-heteroaryl, OSO$_2$-substituted heteroaryl, OSO$_2$-heterocyclic, and OSO$_2$ substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

The term "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

"Thiol" refers to the group —SH.

"Thioxo" or the term "thioketo" refers to the atom (═S).

"Alkylthio" or the term "thioalkoxy" refers to the group —S-alkyl, wherein alkyl is as defined herein. In certain embodiments, sulfur may be oxidized to —S(O)—. The sulfoxide may exist as one or more stereoisomers.

The term "substituted thioalkoxy" refers to the group —S-substituted alkyl.

The term "thioaryloxy" refers to the group aryl-S— wherein the aryl group is as defined herein including optionally substituted aryl groups also defined herein.

The term "thioheteroaryloxy" refers to the group heteroaryl-S— wherein the heteroaryl group is as defined herein including optionally substituted aryl groups as also defined herein.

The term "thioheterocyclooxy" refers to the group heterocyclyl-S— wherein the heterocyclyl group is as defined herein including optionally substituted heterocyclyl groups as also defined herein.

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with ═O, ═NR$^{70}$, ═N—OR$^{70}$, ═N$_2$ or ═S) on saturated carbon atoms in the specified group or radical are, unless otherwise specified, —R$^{60}$, halo, ═O, —OR$^{70}$, —SR$^{70}$, —NR$^{80}$R$^{80}$, trihalomethyl, —CN, —OCN, —SCN, —NO, —NO$_2$, ═N$_2$, —N$_3$, —SO$_2$R$^{70}$, —SO$_2$O$^-$M$^+$, —SO$_2$OR$^{70}$, —OSO$_2$R$^{70}$, —OSO$_2$O$^-$M$^+$, —OSO$_2$OR$^{70}$, —P(O)(O$^-$)$_2$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —C(O)O$^-$ M$^+$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)O$^-$M$^+$, —OC(O)OR$^{70}$, —OC(S)OR$^{70}$, —NR$^{70}$C(O)R$^{70}$, —NR$^{70}$C(S)R$^{70}$, —NR$^{70}$CO$_2^-$ M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each R$^{70}$ is independently hydrogen or R$^{60}$; each R$^{80}$ is independently R$^{70}$ or alternatively, two R$^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or C$_1$-C$_3$ alkyl substitution; and each M$^+$ is a counter ion with a net single positive charge. Each M$^+$may independently be, for example, an alkali ion, such as K$^+$, Na$^+$, Li$^+$; an ammonium ion, such as +N(R$^{60}$)$_4$; or an alkaline earth ion, such as [Ca$^{2+}$]$_{0.5}$, [Mg$^{2+}$]$_{0.5}$, or [Ba$^{2+}$]$_{0.05}$ ("subscript 0.5 means that one of the counter ions for such divalent alkali earth ions can be an ionized form of a compound of the invention and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, —NR$^{80}$R$^{80}$ is meant to include —NH$_2$, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, —R$^{60}$, halo, —O$^-$M$^+$, —OR$^{70}$, —SR$^{70}$, —S$^-$M$^+$, —NR$^{80}$R$^{80}$, trihalomethyl, —CF$_3$, —CN, —OCN, —SCN, —NO, —NO$_2$, —N$_3$, —SO$_2$R$^{70}$, —SO$_3$$^-$M$^+$, —SO$_3$R$^{70}$, —OSO$_2$R$^{70}$, —OSO$_3$$^-$M$^+$, —OSO$_3$R$^{70}$, —PO$_3$$^{-2}$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —CO$_2$$^-$M$^+$, —CO$_2$R$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OCO$_2$$^-$M$^+$, —OCO$_2$R$^{70}$, —OC(S)OR$^{70}$, —NR$^{70}$C(O)R$^{70}$, —NR$^{70}$C(S)R$^{70}$, —NR$^{70}$CO$_2$$^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined, provided that in case of substituted alkene or alkyne, the substituents are not —O$^-$M$^+$, —OR$^{70}$, —SR$^{70}$, or —S$^-$M$^+$.

In addition to the groups disclosed with respect to the individual terms herein, substituent groups for hydrogens on nitrogen atoms in "substituted" heteroalkyl and cycloheteroalkyl groups are, unless otherwise specified, —R$^{60}$, —O$^-$M$^+$, —OR$^{70}$, —SR$^{70}$, —S$^-$M$^+$, —NR$^{80}$R$^{80}$ trihalomethyl, —CF$_3$, —CN, —NO, —NO$_2$, —S(O)$_2$R$^{70}$, —S(O)$_2$O$^-$M$^+$, —S(O)$_2$OR$^{70}$, —OS(O)$_2$R$^{70}$, —OS(O)$_2$O$^-$M$^+$, —O S(O)$_2$ OR$^{70}$, —P(O)(O—)$_2$(M$^+$)$_2$, —P(O)(OR$^{70}$)O$^-$M$^+$, —P(O)(OR$^{70}$)(OR$^{70}$), —C(O)R$^{70}$, —C(S)R$^{70}$, —C(NR$^{70}$)R$^{70}$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)OR$^{70}$, —OC(S)OR$^{70}$, —NR$^{70}$C(O)R$^{70}$, —NR$^{70}$C(S)R$^{70}$, —NR$^{70}$C(O)OR$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

In some embodiments, where a compound, chemical moiety or functional group is described as substituted, the alternative radical substituent moiety is generally selected from the group consisting of hydroxy, oxo, nitro, trifluoromethyl, halogen, alkoxy, alkylenedioxy, aminoalkyl, aminoalkoxy, amino, monoalkylamino, dialkylamino, alkylcarbonylamino, alkoxycarbonylamino, alkoxycarbonyl, carboxy, hydroxyalkoxy, alkoxyalkoxy, monoalkylaminoalkoxy, dialkylaminoalkoxymono(carboxyalkyl)amino, bis(carboxyalkyl)amino, alkoxycarbonyl, alkynylcarbonyl, alkylsulfonate, alkenylsulfonate, alkynylsulfonate, arylsulfonate, alkylsulfinyl, alkylsulfonamido, arylsulfonamido, alkylsulfonamido, carboxyalkoxy, carboxyalkyl, carboxyalkylamino, cyano, trifluoromethoxy, perfluoroethoxy, guanidine, amidino, oxyguanidino, alkylimino, formylimino, acyl nitrile, acyl azide, acetyl azide, dichlorotriazene, isothiocyante, sulfonyl halide, sulfosuccinimidyl ester, isocyante, acyl halide, aldehyde, haloacetamide, maleimido, aziridinyl, alkylthio (disulfide), acrylo, haloalkylcarbonyl, boronate, hydrazide, semicarbazide, carbohydrazide, arylalkyl, heteroarylalkyl, cycloalkylalkyl, cycloalkenylalkyl, cycloheteroalkylalkyl, and cycloheteroalkenylalkyl.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N=C(H)—NH— ring atom arrangement, such as pyrazoles, imidazoles, benzimidazoles, triazoles, and tetrazoles. A person of ordinary skill in the art would recognize that other tautomeric ring atom arrangements are possible.

It will be appreciated that the term "or a salt or solvate or stereoisomer thereof" is intended to include all permutations of salts, solvates and stereoisomers, such as a solvate of a pharmaceutically acceptable salt of a stereoisomer of subject compound.

As used herein, the term "biopolymer" is used generically to refer to amino acid polymers, nucleic acid polymers, carbohydrates, polysaccharides, and lipids, each as broadly defined herein.

The terms "amino acid polymer", "polypeptide," "peptide," and "protein" are used interchangeably herein to refer to a polymeric form of amino acids of any length, including proteins that have been subject to co-translational or post-translational modification, such as glycoproteins. The amino acid polymer may comprise both standard (i.e., one of the 20 amino acids encoded by the standard genetic code, also referred to as proteinogenic) and nonstandard amino acids, may be derivatized, protected, or substituted, such as, for example, by phosphates, carbohydrates, or $C_1$ to $C_{25}$ carboxylic acids. The terms "peptide", "polypeptide", and "protein" are used herein interchangeably without a distinction as to the length of the polymer, although short polymers of amino acids are typically referred to as peptides or polypeptides and longer polymers of amino acids, particularly those that are naturally occurring and/or have a biological function, are referred to as proteins. The term includes fusion proteins, including, but not limited to, fusion proteins with a heterologous amino acid sequence, fusions with heterologous and homologous leader sequences, proteins which contain at least one N-terminal methionine residue (e.g., to facilitate production in a recombinant bacterial host cell); immunologically tagged proteins; and the like.

"Native amino acid sequence" or "parent amino acid sequence" are used interchangeably herein to refer to the amino acid sequence of a polypeptide prior to modification to include a modified amino acid residue.

The terms "amino acid analog," "unnatural amino acid," and the like may be used interchangeably, and include amino acid-like compounds that are similar in structure and/or overall shape to one or more amino acids commonly found in naturally occurring proteins (e.g., Ala or A, Cys or C, Asp or D, Glu or E, Phe or F, Gly or G, His or H, Ile or I, Lys or K, Leu or L, Met or M, Asn or N, Pro or P, Gln or Q, Arg or R, Ser or S, Thr or T, Val or V, Trp or W, Tyr or Y). Amino acid analogs also include natural amino acids with modified side chains or backbones. Amino acids also include naturally occurring amino acids in D-, rather than L-form. In some instances, the amino acid analogs share backbone structures, and/or the side chain structures of one or more natural amino acids, with difference(s) being one or more modified groups in the molecule. Such modification may include, but is not limited to, substitution of an atom (such as N) for a related atom (such as S), addition of a group (such as methyl, or hydroxyl, etc.) or an atom (such as Cl or Br, etc.), deletion of a group, substitution of a covalent bond (single bond for double bond, etc.), or combinations thereof. For example, amino acid analogs may include α-hydroxy acids, and α-amino acids, and the like.

As used herein, the term "antibody" includes all products, derived or derivable from antibodies or from antibody genes, which are useful as target-specific binding reagents. The term "antibody" is used in the broadest sense and includes monoclonal antibodies (including full length monoclonal antibodies), polyclonal antibodies, and multispecific antibodies (e.g., bispecific antibodies), genetically-engineered antibodies, humanized antibodies, single-chain antibodies, chimeric antibodies, antibody fragments (e.g., Fab fragments), antibody derivatives and the like. An antibody is capable of binding a target antigen. (Janeway, C., Travers, P., Walport, M., Shlomchik (2001) Immuno Biology, 5th Ed., Garland Publishing, New York). A target antigen can have one or more binding sites, also called epitopes, recognized by complementarity determining regions (CDRs) formed by one or more variable regions of an antibody.

The term "natural antibody" refers to an antibody in which the heavy and light chains of the antibody have been made and paired by the immune system of a multi-cellular organism. Spleen, lymph nodes, bone marrow and serum are examples of tissues that produce natural antibodies. For example, the antibodies produced by the antibody producing cells isolated from a first animal immunized with an antigen are natural antibodies.

The term "humanized antibody" or "humanized immunoglobulin" refers to a non-human (e.g., mouse or rabbit) antibody containing one or more amino acids (in a framework region, a constant region or a CDR, for example) that have been substituted with a correspondingly positioned amino acid from a human antibody. In general, humanized antibodies produce a reduced immune response in a human host, as compared to a non-humanized version of the same antibody. Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska. et al., PNAS 91:969-973 (1994)), and chain shuffling (U.S. Pat. No. 5,565,332). In certain embodiments, framework substitutions are identified by modeling of the interactions of the CDR and framework residues to identify framework residues important for antigen binding and sequence comparison to identify unusual framework residues at particular positions (see, e.g., U.S. Pat. No. 5,585,089; Riechmann et al., Nature 332:323 (1988)). Additional methods for humanizing antibodies contemplated for use in the present invention are described in U.S. Pat. Nos. 5,750,078; 5,502,167; 5,705,154; 5,770,403; 5,698,417; 5,693,493; 5,558,864; 4,935,496; and 4,816,567, and PCT publications WO 98/45331 and WO 98/45332. In particular embodiments, a subject rabbit antibody may be humanized according to the methods set forth in US20040086979 and US20050033031. Accordingly, the antibodies described above may be humanized using methods that are well known in the art.

The term "chimeric antibodies" refer to antibodies whose light and heavy chain genes have been constructed, typically by genetic engineering, from antibody variable and constant region genes belonging to different species. For example, the variable segments of the genes from a mouse monoclonal antibody may be joined to human constant segments, such as gamma 1 and gamma 3. An example of a therapeutic chimeric antibody is a hybrid protein composed of the variable or antigen-binding domain from a mouse antibody and the constant or effector domain from a human antibody, although domains from other mammalian species may be used.

As used herein, the terms "nucleic acid polymer", "nucleic acid", and "oligonucleotide" refer to polydeoxyribonucleotides (containing 2-deoxy-D-ribose), to polyribonucleotides (containing D-ribose), and to any other type of polynucleotide which is an N glycoside of a purine or pyrimidine base, or modified purine or pyrimidine base. There is no intended distinction in length between the terms "nucleic acid" and "oligonucleotide", and these terms will be used interchangeably. These terms refer only to the primary structure of the molecule. Thus, these terms include double- and single-stranded DNA, as well as double- and single-stranded RNA. Nucleic acid polymers is intended to include peptide nucleic acids, such as N-(2-aminoethyl)glycine units (see Nielsen et al., U.S. Pat. No. 5,539,082).

By "genetically-encodable" as used in reference to an amino acid sequence of polypeptide, peptide or protein means that the amino acid sequence is composed of amino acid residues that are capable of production by transcription and translation of a nucleic acid encoding the amino acid sequence, where transcription and/or translation may occur in a cell or in a cell-free in vitro transcription/translation system.

The term "control sequences" refers to DNA sequences that facilitate expression of an operably linked coding sequence in a particular expression system, e.g. mammalian cell, bacterial cell, cell-free synthesis, etc. The control sequences that are suitable for prokaryote systems, for example, include a promoter, optionally an operator sequence, and a ribosome binding site. Eukaryotic cell systems may utilize promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate the initiation of translation. Generally, "operably linked" means that the DNA sequences being linked are contiguous, and, in the case of a secretory leader, contiguous and in reading frame. Linking is accomplished by ligation or through amplification reactions. Synthetic oligonucleotide adaptors or linkers may be used for linking sequences in accordance with conventional practice.

The term "expression cassette" as used herein refers to a segment of nucleic acid, usually DNA, that can be inserted into a nucleic acid (e.g., by use of restriction sites compatible with ligation into a construct of interest or by homologous recombination into a construct of interest or into a host cell genome). In general, the nucleic acid segment comprises a polynucleotide that encodes a polypeptide of interest, and the cassette and restriction sites are designed to facilitate insertion of the cassette in the proper reading frame for transcription and translation. Expression cassettes can also comprise elements that facilitate expression of a polynucleotide encoding a polypeptide of interest in a host cell. These elements may include, but are not limited to: a promoter, a minimal promoter, an enhancer, a response element, a terminator sequence, a polyadenylation sequence, and the like.

As used herein the term "isolated" is meant to describe a compound of interest that is in an environment different from that in which the compound naturally occurs. "Isolated" is meant to include compounds that are within samples that are substantially enriched for the compound of interest and/or in which the compound of interest is partially or substantially purified.

As used herein, the term "substantially purified" refers to a compound that is removed from its natural environment and is at least 60% free, at least 75% free, at least 80% free, at least 85% free, at least 90% free, at least 95% free, at least 98% free, or more than 98% free, from other components with which it is naturally associated.

The term "physiological conditions" is meant to encompass those conditions compatible with living cells, e.g., predominantly aqueous conditions of a temperature, pH, salinity, etc. that are compatible with living cells.

By "reactive partner" is meant a molecule or molecular moiety that specifically reacts with another reactive partner to produce a reaction product. Exemplary reactive partners include a cysteine or serine of sulfatase motif and Formylglycine Generating Enzyme (FGE), which react to form a reaction product of a converted aldehyde tag containing a formylglycine (fGly) in lieu of cysteine or serine in the motif. Other exemplary reactive partners include an aldehyde of an fGly residue of a converted aldehyde tag and an "aldehyde-reactive reactive partner", which comprises an aldehyde-reactive group and a moiety of interest, and which reacts to form a reaction product of a modified aldehyde tagged polypeptide having the moiety of interest conjugated to the modified polypeptide through a modified fGly residue.

"N-terminus" refers to the terminal amino acid residue of a polypeptide having a free amine group, which amine group in non-N-terminus amino acid residues normally forms part of the covalent backbone of the polypeptide.

"C-terminus" refers to the terminal amino acid residue of a polypeptide having a free carboxyl group, which carboxyl group in non-C-terminus amino acid residues normally forms part of the covalent backbone of the polypeptide.

By "internal site" as used in referenced to a polypeptide or an amino acid sequence of a polypeptide means a region of the polypeptide that is not at the N-terminus or at the C-terminus.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed, to the extent that such combinations embrace subject matter that are, for example, compounds that are stable compounds (i.e., compounds that can be made, isolated, characterized, and tested for biological activity). In addition, all sub-combinations of the various embodiments and elements thereof (e.g., elements of the chemical groups listed in the embodiments describing such variables) are also specifically embraced by the present invention and are disclosed herein just as if each and every such sub-combination was individually and explicitly disclosed herein.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is to be noted that, as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination, without departing from the scope or spirit of the present invention. Any recited method can be carried out in the order of events recited or in any other order which is logically possible.

DETAILED DESCRIPTION

The present disclosure provides hydroxamate substituted azaindoline-cyanine dyes, dye-conjugates, and methods of making and using the same. Embodiments of each are described in more detail in the sections below.

In some cases, the incorporation of a hydroxamate and an azaindoline ring system into a cyanine dye results in dye-substrate conjugates (e.g., proteins, nucleic acids and other biopolymer conjugates) that are substantially more fluorescent, and have any one of a variety of improved fluorescent properties as compared to conjugates labeled with conventional dyes. Conjugates of the subject dyes may provide for reduced undesirable effects such as quenching, lack of photostability, low quantum efficiency, or any undesirable changes in fluorescence properties of the dyes. The enhanced fluorescence intensity of dye-biomolecule conjugates of the invention results in greater assay sensitivity and decreased artifacts in their absorption spectra upon conjugation to biopolymers. In addition, the subject dyes may also have significantly enhanced photostability. The addition of the hydroxamate substituent increases the photostability of the subject dyes. These improvements result in significantly greater sensitivity in assays that use the subject dyes and conjugates thereof, while utilizing existing filters and instrumentation already commercially available for use with similar dyes such as Cy5, Cy5.5, Alexa Fluor 700 and Cy7.

Furthermore, in some cases, the subject dyes exhibit absorbance maxima longer than the common carbocyanine dyes, so these dyes can be selected to match the principal emission lines of the HeNe laser (633 nm) or longer-wavelength laser diodes. They are useful for samples that are transparent to infrared wavelengths. In some instances, the dyes of the invention have an absorbance maximum within 30 nm (such as within 20 nm, within 10 nm, or within 5 nm) of the principle emission line of the HeNe laser.

In some instances, the dyes have an absorption maximum that is 550 nm or greater, such as 580 nm or greater, 590 nm or greater, 600 nm or greater, 610 nm or greater, 620 nm or greater, 630 nm or greater, 640 nm or greater, 650 nm or greater, 660 nm or greater, 680 nm or greater, 690 nm or greater, 700 nm or greater, 710 nm or greater, 720 nm or greater, 730 nm or greater, 740 nm or greater, 750 nm or greater, or even greater.

In some instances, the dyes have an emission maximum that is 600 nm or greater, such as 620 nm or greater, 640 nm or greater, 650 nm or greater, 660 nm or greater, 680 nm or greater, 700 nm or greater, 720 nm or greater, 740 nm or greater, 750 nm or greater, 760 nm or greater, 780 nm or greater, 800 nm or greater, or even greater.

The subject dyes and conjugates thereof may have a variety of useful properties for biological detections. In some embodiments, the dye compounds and/or conjugates, have high photostability (e.g., are photostable). In some embodiments, the dye compounds and/or conjugates have desirable absorption and emission characteristics at longer wavelengths, which reduce any interference from autofluorescence or background fluorescence of many ligands, receptors, and materials in the sample under test, e.g. blood, urine, cerebrospinal fluid. In some embodiments, the dye compounds are readily conjugated to a biological molecule (e.g., an antibody) in high yield with little or no change in the fluorescence properties of the dye and binding properties of the ligand. In some embodiments, the dyes have high quantum efficiency. In some embodiments, the dyes have large extinction coefficients.

Hydroxamate Substituted Azaindoline-Cyanine Dye Compounds

The hydroxamate substituted azaindoline-cyanine dyes are cyanine-based dyes that include a first ring system and a second ring system connected via a polymethine linking group. The first ring system may be an azaindoline ring system that is substituted with a hydroxamate group at any convenient position. The second ring system may be any convenient ring system. In some embodiments, the second ring system includes a 5-membered heterocyclic ring. The dye may further include one or more reactive group moieties for conjugation of the dye to a substrate. The dye may include one or more water soluble groups at any convenient positions.

The azaindoline ring system may be connected to the polymethine linking group at any convenient position. In some cases, the azaindoline ring system is connected to the polymethine linking group at the 2-position. In some cases, the azaindoline ring system includes a pyridium moiety incorporated into an indoline ring structure to form the azaindoline ring. As used herein, the terms "azaindoline ring system", "azaindoline" and "azaindoline derivative", are used interchangeably and, by itself or as part of another group, means any moiety that contains one of the following fused ring structures or a derivative thereof:

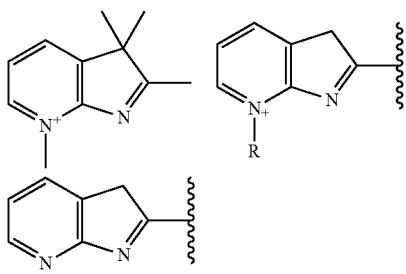

Azaindoline Structure (R is a N substitutent)

It is to be understood that the azaindoline moieties of the invention have been drawn in one or another particular electronic resonance structure. Every aspect of the instant invention applies equally to dyes that are formally drawn with other permitted resonance structures, as the electronic charge on the subject dyes are delocalized throughout the dye itself.

In some embodiments, the azaindoline ring system is substituted with a hydroxamate group at the 4-position. In some embodiments, the azaindoline ring system is substituted with a hydroxamate group at the 5-position. In some embodiments, the azaindoline ring system is substituted with a hydroxamate group at the 6-position. As used herein, the terms "hydroxamate", "hydroxamic acid", "hydroxamic ester", "hydroxamic", "hydroxamic derivative" are used interchangeably and, by itself or as part of another group, refer to a moiety that contains the following structure or a derivative thereof:

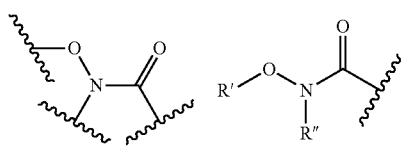

Hydroxamate Structures where R' and R" are independently hydrogen or a substituent. As such, as used herein the term hydroxamate encompasses both hydroxamic acid groups and hydroxamic esters. The hydroxamate group may be attached to a ring system of the dye via any convenient atom, the O, the N or the carbonyl of the hydroxamate. In some cases, the hydroxamate group is attached via the carbonyl to the azaindoline ring system. In some cases, the dye is a 5-hydroxamate substituted azaindoline-cyanine dye compound, e.g., where a first azaindoline ring system is substituted at the 5-position with a hydroxamate group.

In some embodiments, the second ring system includes a 5-membered heterocyclic ring that is connected to the polymethine linking group of the dye via any convenient position of the ring. In certain embodiments, the 5-membered heterocyclic ring includes a carbon atom in the ring that forms a double bond to the divalent polymethine linking group. In some instances, the five-membered heterocyclic ring includes one or more nitrogen atoms in the ring. In some cases, each atom of the five-membered heterocyclic ring is independently selected from the group consisting of C, CH, C(alkyl), C(aryl), O, S, N, N(aryl), N(acyl) and N(alkyl). In certain instances, the five-membered heterocyclic ring containing one nitrogen atom. In some embodiments, the five-membered heterocyclic ring is a saturated five membered heterocycle ring fused to an unsaturated aromatic ring or ring system. In some instances, the five-membered heterocyclic ring is a pyrrolidine ring. In some instances, the pyrrolidine ring is optionally fused at the 4/5 positions to an aryl or heteroaryl ring or ring system. In some instances, the pyrrolidine ring is substituted at the 2-position with a polymethine linking group of the dye.

The 5-membered heterocyclic ring may be optionally fused at any convenient positions to one or more aromatic rings, e.g., one or more aryl or heteroaryl rings as described above to provide for the second ring system of the dye compounds. Any convenient aryl and heteroaryl rings may be selected for inclusion in the second ring system. In some cases, the one or more aryl or heteroaryl rings fused to the 5-membered heterocyclic ring include only six-membered rings. Aryl and heteroaryl rings and ring systems of interest for including in the second ring system of the dye compounds include, but are not limited to, pyridinyl, pyrrolyl, indolyl, In certain instances, in Formula I, B is optionally fused to one aryl or heteroaryl ring. In some instances, the 5-membered heterocyclic ring is optionally fused to two aryl and/or heteroaryl rings. In certain cases, the 5-membered heterocyclic ring is optionally fused to three aryl and/or heteroaryl rings. In some embodiments, the 5-membered heterocyclic ring is fused to a benzo ring. In some instances, the 5-membered heterocyclic ring is fused to a pyridyl ring. In some embodiments, the second ring system is an indoline or azaindoline ring system. In certain embodiments, the 5-membered heterocyclic ring is fused to a polycyclic aryl. In certain embodiments, the 5-membered heterocyclic ring is fused to a naphthalene. In certain embodiments, the 5-membered heterocyclic ring is fused to an anthracene. The five-membered heterocyclic ring and the zero to three aromatic rings are each optionally substituted with one or more substituents.

In some instances, the polymethine linking group is selected to form a conjugated system of unsaturated bonds between a first azaindoline ring system and a second ring system including a 5-membered heterocyclic ring. The divalent polymethine linking group may include a backbone of 1 to 15 carbon atoms (e.g., 1, 3, 5, 7, 9, 11, 13 or 15 atoms), where every carbon atom of the backbone may be optionally independently substituted. As used herein, the divalent polymethine linking group encompasses a linking group that includes one methine group, e.g., 1 carbon atom. In some embodiments, the polymethine linking group includes a backbone of 3 carbon atoms. In certain embodiments, the polymethine linking group includes a backbone of 5 carbon atoms. In certain embodiments, the polymethine linking group includes a backbone of 7 carbon atoms. In some instances, the polymethine linking group is substituted with a RGM. In certain instances, the RGM group is connected via a non-terminal carbon atom of the backbone.

The hydroxamate substituted azaindoline-cyanine dye may be further substituted at any convenient positions with one or more substituents. Any convenient substituents may be included. In some instances, the compound includes one or more substituents that include a reactive group moiety (RGM). In some cases, the compound includes one or more substituents that include a substrate. In certain instances, the compound includes one or more substituents (e.g., 1, 2, 3 or more substituents) that include a water-soluble group (e.g., a polar group or a charged group such as a sulfonate, a carboxy, an ammonium or a phosphate group).

One or more RGM groups may be included directly or indirectly at any convenient positions of the dye structure. In some instances, the 5-membered heterocyclic ring includes one N atom, and the N-atom is substituted with a linker-RGM. In certain cases, the 5-hydroxamate substituent of the azaindoline group is further substituted with a linker-RGM. In some cases, the polymethine linking group is substituted to include a linker-RGM.

As used herein, a "reactive group moiety", denoted "RGM", refers to a moiety on a compound that is capable of chemically reacting with a functional group on a different compound to form a covalent linkage (e.g., conjugating). A variety of reactive group moieties (RGM) and conjugation chemistries may be utilized in the subject dye compounds and conjugates thereof, as described in greater detail below. RGMs of interest include, but are not limited to, an acrylamide, an amine, a carboxylic acid, an activated ester of a carboxylic acid, an acyl azide, an acyl nitrile, an aldehyde, an alkyl halide, an anhydride, an aryl halide, an azide, an aziridine, a boronate, a diazoalkane, a haloacetamide, a halotriazine, a hydrazine, a hydroxylamine, an imido ester, an isocyanate, an isothiocyanate, a maleimide, a reactive platinum complex, a sulfonyl halide or a psoralen derivative. In certain cases, RGM is a succinimidyl ester, or a maleimide. In some cases, the reactive group moiety is an electrophile or a nucleophile that can form a covalent linkage through exposure to a corresponding functional group of a substrate that is a compatible nucleophile or electrophile, respectively. In other cases, the reactive group moiety may a photoactivatable group, which becomes chemically reactive only after illumination with light of an appropriate wavelength. In some instances, the conjugation reaction between the reactive dye and the substance to be conjugated results in one or more atoms of the reactive group RGM to be incorporated into a new linkage L attaching the dye to the conjugated substrate. Some examples of reactive groups and linkages are shown in Table 3 where the reaction of an electrophilic group and a nucleophilic group yields a covalent linkage.

L is a linker that may connect the cyanine dye moiety and an RGM. In some cases, the cyanine dye compounds can be conjugated either directly to a RGM or a substrate or, alternatively, indirectly to a RGM or a substrate through a linker, L. For economy of notation, both alternatives are described herein by a single structure having an optional linker. An embodiment of a structure having an optional linker, L, in which the linker is not present can be described as the structure in which L is "none" or "absent". As used herein, a "linker", denoted "L", between two moieties is referred to as "optional" if the two moieties can be bound either directly to each other or through the linker as an intermediate. This language is used to simplify the description of alternative structures that differ only by the presence or absence of the linker. In the present invention, for example, the cyanine dye molecules can be conjugated either directly to the biopolymer or, alternatively, indirectly to the biopolymer through a linker, L. For economy of notation, both alternatives are described herein by a single structure having an optional linker. An embodiment of a structure having an optional linker, L, in which the linker is not present can be described as the structure in which L is "none". Any convenient linker groups may be utilized in the subject dyes. For example, the linker moiety may include one or more monomer units, such as ethylene oxide of the formula —($CH_2$—$CH_2$—O)— or —(O—$CH_2$—$CH_2$)—. The number of such units can vary, with the number of such units being from 2 to 10, 2 to 8, 2 to 6, 2 to 4, for example some embodiments include 2 units. Furthermore, the last monomer unit (e.g., an ethylene oxide group) in the linker group may be further substituted by one or more functional groups as defined herein, such as, for example, alkyl, substituted alkyl, alkenyl, substituted alkenyl, alkynyl, substituted alkynyl, hydroxyl, alkoxy, substituted alkoxy, amino, substituted amino, acyl, carboxyl, carboxyl ester, acylamino, aminoacyl, alkylamide, substituted alkylamide, aryl, substituted aryl, heteroaryl, substituted heteroaryl, cycloalkyl, substituted cycloalkyl, heterocyclyl, or substituted heterocyclyl. In some instances, the last monomer unit (e.g., a last ethylene oxide group) in the linker group may be further substituted by a carboxyl, or a protected carboxyl group, such as a perfluorophenyl protected carboxyl group. In some cases, L is none, an alkyl, an alkoxy, a thioalkyl, an amino acid, a sulfo amino acid, polyamine, a polyethyleneglycol, an aryl, an arylalkyl, a heteroaryl alkyl, or a heteroaryl. In certain embodiments, the linking group comprises 10-15 carbon atoms and/or 0-6 heteroatoms. Additionally, linkers can comprise modified or unmodified nucleotides, nucleosides, polymers, sugars and other carbohydrates, polyethers, such as for example, polyethylene glycols, polyalcohols, polypropylenes, propylene glycols, mixtures of ethylene and propylene glycols, polyalkylamines, polyamines such as spermidine, polyesters such as poly(ethyl acrylate), polyphosphodiesters, and alkylenes. In certain embodiments, L is none, an alkyl, or a polyethyleneglycol. A linker may be cleavable or non-cleavable.

In some embodiments, the dye compound contains one or more L-RGM substitutent, where RGM is a reactive group moiety that is attached to the dye via a covalent linkage L. In certain embodiments, the dye compound is substituted with only one RGM or conjugated substrate. In some embodiments, the dye compound contains two or more L-RGM groups, such as 2, 3, 4, 5, 6, 7, 8, 9, 10, 12, 14, 16, 18, 20, 30, 40, 50 or even more L-RGM groups, where RGM is a reactive group that is attached to the dye via a covalent linkage L. In certain embodiments, L is a covalent linkage attaching the dye to RGM contains multiple intervening atoms that serve as a spacer.

The dye compounds may include one or more water-soluble substituents at any convenient positions (e.g., a polar or charged substituent) that may be included to impart increased water solubility on the dye. In some instances, the compounds incorporate at least one charged group to increase water solubility. Any convenient charged groups may be incorporated. Charged groups of interest, include but are not limited to, a sulfonate, an ammonium, a carboxy, a phosphate, an amino, a substituted amino and the like. The term "sulfonate", by itself or as part of another group, refers to any compound or substituent that contains sulfonic acid, a salt thereof, e.g., one or more moieties having the following structure:

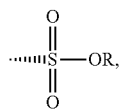

where R is hydrogen or a counter ion, such as a metal ion or ammonium ion. Similarly, by "carboxy" is meant carboxylic acid or salt of carboxylic acid. "Phosphate", as used herein, is an ester of phosphoric acid, and includes salts of phosphate. "Phosphonate", as used herein, means phosphonic acid and includes salts of phosphonate. As used herein, unless otherwise specified, the alkyl portions of substituents such as alkyl, alkoxy, arylalkyl, alylamino, dialkylamino, trialkylammonium, or perfluoroalkyl are optionally saturated, unsaturated, linear or branched, and all alkyl, alkoxy, alkylamino, and dialkylamino substituents are themselves optionally further substituted by carboxy, sulfonate, amino, or hydroxy. Any convenient polar substituents may be incorporated. Polar substituents of interest include, but are not limited to, hydroxyl containing substituents, carbohydrates, and polyethylene glycol groups or linkers.

In some embodiments, the dye is a hydroxamate substituted azaindoline cyanine dye, including a 5-hydroxamate-azaindoline group linked to a 5-membered heterocyclic ring via a divalent polymethine linking group, where one or more of the 5-hydroxamate-azaindoline group, the divalent polymethine linking group and the 5-membered heterocyclic ring is substituted with a reactive group moiety (RGM).

In some cases, the dye is described by Formula I:

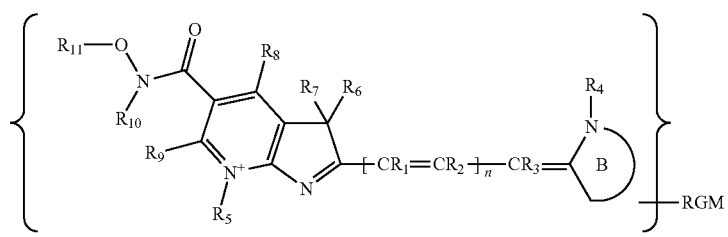

Formula I where ring B represents the atoms necessary to form a nitrogen-containing five-membered heterocyclic ring and further comprises zero to three fused aromatic rings; wherein each atom of the five-membered heterocyclic ring and the zero to three fused aromatic rings is independently selected from the group consisting of C, CH, C(alkyl), C(aryl), O, S, N, N(aryl), N(acyl) and N(alkyl), and the five-membered heterocyclic ring and the zero to three aromatic rings are optionally substituted with one or more substituents selected from the group consisting of a hydrogen, an alkyl having 1-20 carbons, a hydroxy, an alkoxy having 1-20 carbons, a trifluoromethyl, a halogen, a methylthio, a carbonyl, an amino, a thiol, a sulfonate, a phosphonyl, and a L-RGM; n is 0 to 3; $R_1$-$R_3$ are each independently a hydrogen, a halogen, an alkyl having 1-20 carbons, a cycloalkyl having 3-20 carbons, an aryl, a heteroaryl, an amino, an alkylamino, an arylamino, a thiol, an alkylhiol, an arylthiol, a heteroarylthiol, a polyethyleneglycol, an alkoxy, an aryloxy, a carboxyalkyl, a phosphonylalkyl, a sulfonylalkyl, or a L-RGM; $R_4$ and $R_5$ are each independently an alkyl having 1-20 carbons, a cycloalkyl having 3-20 carbons, an arylalkyl, a heteroarylalkyl, a carboxyalkyl, a phosphonylalkyl, a sulfoalkyl, or a L-RGM; $R_6$ and $R_7$ are each independently an alkyl having 1-20 carbons, a cycloalkyl having 3-20 carbons, an aryl, an arylalkyl, a heteroaryl, a heteroarylalkyl, a carboxyalkyl, a carboxylaryl, a phosphonylalkyl, a sulfoalkyl, or a L-RGM; $R_8$ and $R_9$ are each independently a hydrogen, an alkyl having 1-20 carbons, a hydroxy, an alkoxy having 1-20 carbons, a trifluoromethyl, a halogen, a methylthio, a carbonyl, an amino, a thiol, a sulfonate, a phosphonyl or a L-RGM; $R_{10}$ and $R_{11}$ are each independently a hydrogen, an alkyl, an aryl, an arylalkyl, a heteroaryl, a heteroarylalkyl, a carboxyalkyl, a phosphonylalkyl, a sulfoalkyl, or a L-RGM; RGM is a chemically reactive group; and L is a linker.

In some instances, in Formula I, Ring B represents the atoms necessary to form a nitrogen-containing five-membered heterocyclic ring and further includes zero to three fused aromatic rings; where each atom of the five-membered heterocyclic ring and the zero to three fused aromatic ring is independently selected from the group consisting of C, CH, C(alkyl), C(aryl), O, S, N, N(aryl), N(acyl) and N(alkyl). In certain instances, B is a five-membered heterocyclic ring containing one nitrogen atom. In some embodiments, B is a saturated five membered heterocycle ring fused to an unsaturated aromatic ring. In certain cases, each atom of the B ring is independently selected from the group consisting of C, CH, C(alkyl), C(aryl), N, N(aryl), N(acyl) and N(alkyl). In some instances, B is a pyrrolidine ring. In some instances, B is a pyrrolidine ring optionally fused at the 4/5 positions to an aryl or heteroaryl ring or ring system. In some instances, Ring B is a pyrrolidine ring substituted at the 2-position with a polymethine group.

Ring B may be optionally fused to one or more aromatic rings, e.g., one or more aryl or heteroaryl rings as described above to provide for the second ring system of the dye compounds. Any convenient aryl and heteroaryl rings may be selected for inclusion in the second ring system. In some cases, the one or more aryl or heteroaryl rings fused to B include only six-membered rings. Aryl and heteroaryl rings and ring systems of interest for including in the second ring system of the dye compounds include, but are not limited to, pyridinyl, pyrrolyl, indolyl, In certain instances, in Formula I, B is optionally fused to one aryl or heteroaryl ring. In some instances, in Formula I, B is optionally fused to two aryl and/or heteroaryl rings. In certain cases, in Formula I, B is optionally fused to three aryl and/or heteroaryl rings. In some embodiments, Ring B is fused to a benzo ring. In some instances, B is fused to a pyridyl ring. In some embodiments, the second ring system is an indoline or azaindoline ring system. In certain embodiments, Ring B is fused to a polycyclic aryl. In certain embodiments, Ring B is fused to a naphthalene. In certain embodiments, Ring B is fused to an anthracene.

The five-membered heterocyclic ring and the zero to three aromatic rings are optionally substituted with one or more substituents independently selected from the group consisting of a hydrogen, an alkyl having 1-20 carbons, a hydroxy, an alkoxy having 1-20 carbons, a trifluoromethyl, a halogen, a methylthio, a carbonyl, an amino, a thiol, a sulfonate, a phosphonyl, and a L-RGM.

In some embodiments, in Formula I, n is 0. In some embodiments, in Formula I, n is 1. In some embodiments, in Formula I, n is 2. In some embodiments, in Formula I, n is 3.

In some cases, in Formula I, $R_1$-$R_3$ are independently a hydrogen, a halogen, an alkyl having 1-20 carbons, a cycloalkyl having 3-20 carbons, an aryl, a heteroaryl, an amino, an alkylamino, an arylamino, a thiol, an alkylhiol, an arylthiol, a heteroarylthiol, a polyethyleneglycol, an alkoxy, an aryloxy, a carboxyalkyl, or a L-RGM. In certain cases, $R_1$-$R_3$ are each hydrogen. In certain cases, in Formula I, two of $R_1$-$R_3$ are cyclically linked to form a six-membered carbocycle or heterocycle ring. In certain embodiments, in Formula I, one of $R_1$-$R_3$ is an alkoxy, an aryloxy, or a L-RGM.

In some cases, in Formula I, $R_4$ and $R_5$ are independently an alkyl having 1-20 carbons, a cycloalkyl having 3-20 carbons, an arylalkyl, a heteroarylalkyl, a carboxyalkyl, a sulfoalkyl, or a L-RGM.

In some cases, in Formula I, $R_4$ and $R_5$ are each independently selected from an alkyl having 1-20 carbons, where the alkyl may be substituted with one or more substituents selected from a RGM, a sulfonate, a phosphate, amino, a substituted amino, an ammonium, a carboxy, and a hydroxyl. In certain embodiments, $R_4$ and $R_5$ are each independently selected from —$(CH_2)_m$—Z, where m is 1-12 and Z is selected from —H, —$CO_2H$, —$NH_2$, —$SO_3^-$, —$PO_3H$ and RGM.

In certain instances, in Formula I, $R_6$ and $R_7$ are independently an alkyl having 1-20 carbons, a cycloalkyl having 3-20 carbons, an aryl, an arylalkyl, a heteroaryl, a heteroarylalkyl, a carboxyalkyl, a carboxyaryl, a sulfoalkyl, or a L-RGM. In certain instances, in Formula I, $R_6$ and $R_7$ are each independently an alkyl having 1-20 carbons. In certain instances, in Formula I, $R_6$ and $R_7$ are each independently a lower alkyl. In certain instances, in Formula I, $R_6$ and $R_7$ are each methyl. In some embodiments, $R_6$ is a lower alkyl (e.g., a methyl or an ethyl) and $R_7$ is L-RGM. In some embodiments, $R_7$ is L-Z (e.g., —$(CH_2)_m$—Z, where m is 1-12 and Z is selected from —H, —$CO_2H$, —$NH_2$, —$SO_3^-$, —$PO_3H$ and RGM).

In some instances, in Formula I, $R_8$ and $R_9$ are independently a hydrogen, an alkyl having 1-20 carbons, a hydroxy, an alkoxy having 1-20 carbons, a trifluoromethyl, a halogen, a methylthio, a sulfonate, a carbonyl, a hydroxy, an amino, a thiol, a phosphonyl, or a L-RGM. In some instances, in Formula I, $R_8$ and $R_9$ are each independently a hydrogen or an alkyl having 1-20 carbons. In some instances, in Formula I, $R_8$ and $R_9$ are each independently a hydrogen or L-RGM. In some instances, in Formula I, $R_8$ and $R_9$ are each hydrogen. In certain embodiments, $R_9$ is cyclically linked to the adjacent N of the azaindoline ring, e.g., to form a 6 membered ring.

In some embodiments, in Formula I, $R_{10}$ and $R_{11}$ are each independently, a hydrogen, an alkyl, an aryl, an arylalkyl, a heteroaryl, a heteroarylalkyl, a carboxyalkyl, a sulfoalkyl, or a L-RGM. In certain embodiments, in Formula I, $R_{10}$ and $R_{11}$ are each independently hydrogen, an alkyl, an aryl or L-RGM. In some instances, in Formula I, $R_{10}$ and $R_{11}$ are each independently an alkyl, such as a lower alkyl (e.g., methyl, ethyl, propyl, isopropyl, etc.). In certain instances, in Formula I, $R_{10}$ is L-RGM. In certain cases, in Formula I, $R_{11}$ is L-RGM.

In some cases, L is none, an alkyl, or a polyethyleneglycol.

In certain embodiments, RGM is a succinimidyl ester, or a maleimide.

In certain embodiments, in Formula I, at least one of $R_1$-$R_{11}$ includes a L-RGM. In certain instances, in Formula I, B includes a L-RGM. In certain embodiments, in Formula I, two of $R_1$-$R_{11}$ include a L-RGM. In other instances, in Formula I, -RGM is optional.

In some embodiments, the dye compound is described by Formula II:

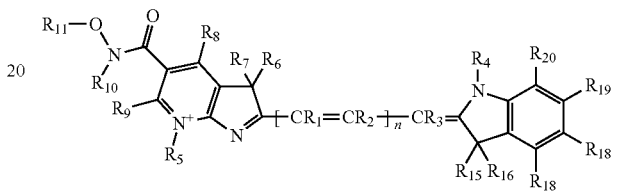

Formula II where, n is 0 to 3; $R_1$-$R_3$ are each independently a hydrogen, a halogen, an alkyl having 1-20 carbons, a cycloalkyl having 3-20 carbons, an aryl, a heteroaryl, an amino, an alkylamino, an arylamino, a thiol, an alkylhiol, an arylthiol, a heteroarylthiol, a polyethyleneglycol, an alkoxy, an aryloxy, a carboxyalkyl, a phosphonylalkyl, a sulfonylalkyl, or a L-RGM; $R_4$ and $R_5$ are each independently an alkyl having 1-20 carbons, an arylalkyl, a carboxyalkyl, a phosphonylalkyl, a sulfoalkyl, or a L-RGM; $R_6$, $R_7$, $R_{15}$ and $R_{16}$ are each independently an alkyl having 1-20 carbons, a cycloalkyl having 3-20 carbons, an aryl, an arylalkyl, a heteroaryl, a heteroarylalkyl, a carboxyalkyl, a carboxylaryl, a sulfoalkyl, or a L-RGM; $R_8$, $R_9$ and $R_{17}$-$R_{20}$ are each independently a hydrogen, an alkyl having 1-20 carbons, a hydroxy, an alkoxy having 1-20 carbons, a trifluoromethyl, a halogen, a methylthio, a carbonyl, an amino, a thiol, a sulfonate, a phosphonyl, or a L-RGM; $R_{10}$ and $R_{11}$ are each independently a hydrogen, an alkyl, an aryl, an arylalkyl, a heteroaryl, a heteroarylalkyl, a carboxyalkyl, a phosphonylalkyl, a sulfoalkyl, or a L-RGM; RGM is a chemically reactive group; L is a linker; and optionally, one or more of $R_4$ and $R_5$, $R_6$ and $R_7$, $R_5$ and $R_9$, $R_{15}$ and $R_{16}$, $R_4$ and $R_{20}$, $R_4$ and $R_6$/$R_7$, or $R_6$/$R_7$ and $R_{15}$/$R_{16}$ is taken in combination to form a 5- to 50-membered ring.

In some instances, in Formula II, $R_1$-$R_3$ are each independently a hydrogen, an alkyl having 1-20 carbons, a cycloalkyl having 3-20 carbons, an aryl, an alkylamino, an arylamino, a thioalkyl, a thiol aryl, an aryloxy, or a L-RGM; $R_4$ and $R_5$ are each independently an alkyl having 1-20 carbons, a carboxyalkyl, a sulfoalkyl, or a L-RGM; $R_6$, $R_7$, $R_{15}$ and $R_{16}$ are each independently an alkyl having 1-20 carbons, a cycloalkyl having 3-20 carbons, an aryl, an arylalkyl, a carboxyalkyl, a carboxylaryl, a sulfoalkyl, or a L-RGM; $R_8$, $R_9$ and $R_{17}$-$R_{20}$ are each independently a hydrogen, an alkyl having 1-20 carbons, a halogen, sulfonate, or a L-RGM; $R_{10}$ and $R_{11}$ are each independently an alkyl, an aryl, an arylalkyl, a carboxyalkyl, a sulfoalkyl, or a L-RGM.

In certain instances, in Formula II, $R_1$-$R_3$ are each a hydrogen; $R_4$ and $R_5$ are each independently an alkyl having 1-20 carbons, a carboxyalkyl, a sulfoalkyl, or a L-RGM; $R_6$, $R_7$, $R_{15}$ and $R_{16}$ are each independently an alkyl having 1-20 carbons, a cycloalkyl having 3-20 carbons, a carboxyalkyl, a carboxyaryl, a sulfoalkyl, a sulfoalkyl, or a L-RGM; $R_8$, $R_9$ and $R_{17}$-$R_{20}$ are each independently a hydrogen, a halogen, sulfonate, or a L-RGM; and $R_{10}$ and $R_{11}$ are each independently an alkyl, or a L-RGM.

In some cases, in Formula II, $R_1$-$R_3$ are each a hydrogen; $R_4$ and $R_5$ are each independently an alkyl having 1-20 carbons, a carboxyalkyl, a sulfoalkyl, or a L-RGM; $R_6$, $R_7$, $R_{15}$ and $R_{16}$ are each independently an alkyl having 1-20 carbons, a cycloalkyl having 3-20 carbons, an aryl, an arylalkyl, a carboxyalkyl, a carboxyaryl, a sulfoalkyl, or a L-RGM; $R_8$, $R_9$, $R_{17}$, $R_{19}$ and $R_{20}$ are each hydrogen; $R_{18}$ is sulfonate; and $R_{10}$ and $R_{11}$ are each independently an alkyl, or a L-RGM.

In certain cases, in Formula II, L is none, an alkyl, an alkoxy, a thioalkyl, an amino acid, a sulfo amino acid, polyamine, a polyethyleneglycol, an aryl, an arylalkyl, a heteroaryl alkyl, or a heteroaryl. In some embodiments, in formula II, L is none, an alkyl, or a polyethyleneglycol.

In some embodiments, in Formula II, n is 0. In some embodiments, in Formula II, n is 1. In some embodiments, in Formula II, n is 2. In some embodiments, in Formula II, n is 3.

In certain instances, in Formula II, $R_1$-$R_3$ are independently a hydrogen, a halogen, an alkyl having 1-20 carbons, a cycloalkyl having 3-20 carbons, an aryl, a heteroaryl, an amino, an alkylamino, an arylamino, a thiol, an alkylhiol, an arylthiol, a heteroarylthiol, a polyethyleneglycol, an alkoxy, an aryloxy, a carboxyalkyl, or a L-RGM. In certain cases, $R_1$-$R_3$ are each hydrogen. In certain cases, in Formula II, two of $R_1$-$R_3$ are cyclically linked to form a six-membered carbocycle or heterocycle ring. In certain embodiments, in Formula II, one of $R_1$-$R_3$ is an alkoxy, an aryloxy, or a L-RGM.

In some cases, in Formula II, $R_4$ and $R_5$ are independently an alkyl having 1-20 carbons, a cycloalkyl having 3-20 carbons, an arylalkyl, a heteroarylalkyl, a carboxyalkyl, a sulfoalkyl, or a L-RGM.

In some cases, in Formula II, $R_4$ and $R_5$ are each independently selected from an alkyl having 1-20 carbons, where the alkyl may be substituted with one or more substituents selected from a RGM, a sulfonate, a phosphate, amino, a substituted amino, an ammonium, a carboxy, and a hydroxyl. In certain embodiments, $R_4$ and $R_5$ are each independently selected from —$(CH_2)_m$—Z, where m is 1-12 and Z is selected from —H, —$CO_2H$, —$NH_2$, —$SO_3^-$, —$PO_3H$ and RGM.

In some embodiments, in Formula II $R_6$, $R_7$, $R_{15}$ and $R_{16}$ are independently an alkyl having 1-20 carbons, a cycloalkyl having 3-20 carbons, an aryl, an arylalkyl, a heteroaryl, a heteroarylalkyl, a carboxyalkyl, a carboxyaryl, a sulfoalkyl, or a L-RGM. In certain instances, in Formula II, $R_6$, $R_7$, $R_{15}$ and $R_{16}$ are each independently an alkyl having 1-20 carbons. In certain instances, in Formula II, $R_6$, $R_7$, $R_{15}$ and $R_{16}$ are each independently a lower alkyl. In certain instances, in Formula II, $R_6$ and $R_7$ are each methyl. In certain instances, in Formula II, $R_{15}$ and $R_{16}$ are each methyl. In some embodiments, $R_6$ is a lower alkyl (e.g., a methyl or an ethyl) and $R_7$ is L-RGM. In some embodiments, $R_7$ is L-Z (e.g., —$(CH_2)_m$—Z, where m is 1-12 and Z is selected from —H, —$CO_2H$, —$NH_2$, —$SO_3^-$, —$PO_3H$ and RGM.) In some embodiments, $R_{15}$ is a lower alkyl (e.g., a methyl or an ethyl) and $R_{16}$ is L-RGM. In some embodiments, $R_{16}$ is L-Z (e.g., —$(CH_2)_m$—Z, where m is 1-12 and Z is selected from —H, —$CO_2H$, —$NH_2$, —$SO_3^{31}$, —$PO_3H$ and RGM.)

In some instances, in Formula II, $R_9$, $R_9$ and $R_{17}$-$R_{20}$ are each independently a hydrogen, an alkyl having 1-20 carbons, a hydroxy, an alkoxy having 1-20 carbons, a trifluoromethyl, a halogen, a methylthio, a carbonyl, an amino, a thiol, a sulfonate, a phosphonyl, or a L-RGM. In some instances, in Formula II, $R_8$, $R_9$ and $R_{17}$-$R_{20}$ are each independently a hydrogen or an alkyl having 1-20 carbons. In some instances, in Formula II, $R_8$, $R_9$ and $R_{17}$-$R_{20}$ are independently a hydrogen or L-RGM. In some instances, in Formula II, $R_8$ and $R_9$ are each hydrogen. In some instances, in Formula II, $R_{17}$-$R_{20}$ are each hydrogen. In certain embodiments, $R_9$ is cyclically linked to the adjacent N of the azaindoline ring, e.g., to form a 6 membered ring.

In some cases, in Formula II, $R_{10}$ and $R_{11}$ are each independently hydrogen, an alkyl, an aryl, an arylalkyl, a heteroaryl, a heteroarylalkyl, a carboxyalkyl, a sulfoalkyl, or a L-RGM. In certain embodiments, in Formula II, $R_{10}$ and $R_{11}$ are each independently hydrogen, an alkyl, an aryl or L-RGM. In some instances, in Formula II, $R_{10}$ and $R_{11}$ are each independently an alkyl, such as a lower alkyl (e.g., methyl, ethyl, propyl, isopropyl, etc.). In certain instances, in Formula II, $R_{10}$ is L-RGM. In certain cases, in Formula II, $R_{11}$ is L-RGM.

One or more of $R_4$ and $R_5$, $R_6$ and $R_7$, $R_5$ and $R_9$, $R_{15}$ and $R_{16}$, $R_4$ and $R_{20}$, $R_4$ and $R_6/R_7$, or $R_6/R_7$ and $R_{15}/R_{16}$ might be taken in combination to form a 5- to 50-membered ring (e.g., a 5- to 12-membered ring, such as a 5, 6, 7 or 8-membered ring).

In some cases, L is none, an alkyl, or a polyethyleneglycol.

In certain embodiments, RGM is a succinimidyl ester, or a maleimide.

In certain embodiments, in Formula II, at least one of $R_1$-$R_{11}$ and $R_{15}$-$R_{20}$ includes a L-RGM. In certain embodiments, in Formula II, two of $R_1$-$R_{11}$ and $R_{15}$-$R_{20}$ include a L-RGM. In other instances, in Formula II, -RGM is optional.

In some embodiments, the dye compound is described by Formula III:

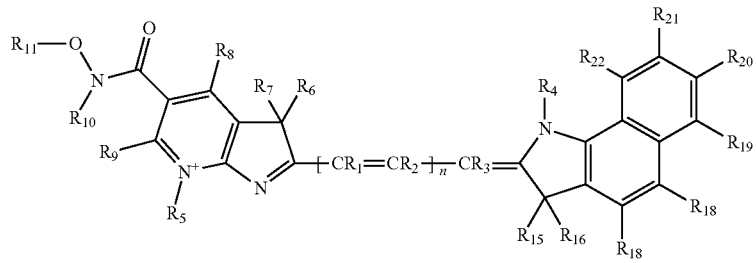

Formula III where, n is 0 to 3; $R_1$-$R_3$ are each independently a hydrogen, a halogen, an alkyl having 1-20 carbons, a cycloalkyl having 3-20 carbons, an aryl, a heteroaryl, an amino, an alkylamino, an arylamino, a thiol, an alkylhiol, an arylthiol, a heteroarylthiol, a polyethyleneglycol, an alkoxy, an aryloxy, a carboxyalkyl, a phosphonylalkyl, a sulfonaylalkyl, or a L-RGM; $R_4$ and $R_5$ are each independently an alkyl having 1-20 carbons, a cycloalkyl having 3-20 carbons, an arylalkyl, a heteroarylalkyl, a carboxyalkyl, a phosphonylalkyl, a sulfonylalkyl, or a L-RGM; $R_6$, $R_7$, $R_{15}$ and $R_{16}$ are each independently an alkyl having 1-20 carbons, a cycloalkyl having 3-20 carbons, an aryl, an arylalkyl, a heteroaryl, a heteroarylalkyl, a carboxyalkyl, a carboxyalkyl, a carboxyaryl, a phosphonylalkyl, a sulfonylalkyl, or a L-RGM; $R_8$, $R_9$ and $R_{17}$-$R_{22}$ are each independently a hydrogen, an alkyl having 1-20 carbons, a hydroxy, an alkoxy having 1-20 carbons, a trifluoromethyl, a halogen, a methylthio, a carbonyl, an amino, a thiol, a sulfonate, a phosphonyl, or a L-RGM; $R_{10}$ and $R_{11}$ are a hydrogen, an alkyl, an aryl, an arylalkyl, a heteroaryl, a heteroarylalkyl, a carboxyalkyl, a sulfoalkyl, or a L-RGM; RGM is a chemically reactive group; L is a linker; and optionally, one or more of $R_4$ and $R_5$, $R_6$ and $R_7$, $R_5$ and $R_9$, $R_{15}$ and $R_{16}$, $R_4$ and $R_{22}$, $R_4$ and $R_6$/$R_7$, or $R_6$/$R_7$ and $R_{15}$/$R_{16}$ is taken in combination to form a 5- to 50-membered ring.

In some embodiments, in Formula III, n is 0. In some embodiments, in Formula III, n is 1. In some embodiments, in Formula III, n is 2. In some embodiments, in Formula III, n is 3.

In certain cases, in Formula III, $R_1$-$R_3$ are independently a hydrogen, a halogen, an alkyl having 1-20 carbons, a cycloalkyl having 3-20 carbons, an aryl, a heteroaryl, an amino, an alkylamino, an arylamino, a thiol, an alkylthiol, an arylthiol, a heteroarylthiol, a polyethyleneglycol, an alkoxy, an aryloxy, a carboxyalkyl, or a L-RGM. In certain instances, in Formula III, $R_1$-$R_3$ are each a hydrogen. In certain cases, in Formula III, two of $R_1$-$R_3$ are cyclically linked to form a six-membered carbocycle or heterocycle ring. In certain embodiments, in Formula III, one of $R_1$-$R_3$ is an alkoxy, an aryloxy, or a L-RGM.

In some embodiments, in Formula III, $R_4$ and $R_5$ are independently an alkyl having 1-20 carbons, a cycloalkyl having 3-20 carbons, an arylalkyl, a heteroarylalkyl, a carboxyalkyl, a sulfoalkyl, or a L-RGM. In certain embodiments, in Formula III, $R_4$ and $R_5$ are each independently an alkyl having 1-20 carbons, a carboxyalkyl, a sulfoalkyl, or a L-RGM. In some cases, in Formula III, $R_4$ and $R_5$ are each independently selected from an alkyl having 1-20 carbons, where the alkyl may be substituted with one or more substituents selected from a RGM, a sulfonate, a phosphate, amino, a substituted amino, an ammonium, a carboxy, and a hydroxyl. In certain embodiments, $R_4$ and $R_5$ are each independently selected from —$(CH_2)_m$—Z, where m is 1-12 and Z is selected from —H, —$CO_2H$, —$NH_2$, —$SO_3^-$, —$PO_3H$ and RGM.

In some embodiments, in Formula III, $R_6$, $R_7$, $R_{15}$ and $R_{16}$ are independently an alkyl having 1-20 carbons, a cycloalkyl having 3-20 carbons, an aryl, an arylalkyl, a heteroaryl, a heteroarylalkyl, a carboxyalkyl, a carboxyaryl, a sulfoalkyl, or a L-RGM. In certain instances, in Formula III, $R_6$, $R_7$, $R_{15}$ and $R_{16}$ are each independently an alkyl having 1-20 carbons. In certain instances, in Formula III, $R_6$, $R_7$, $R_{15}$ and $R_{16}$ are each independently a lower alkyl. In certain instances, in Formula III, $R_6$ and $R_7$ are each methyl. In certain instances, in Formula III, $R_{15}$ and $R_{16}$ are each methyl. In some embodiments, $R_6$ is a lower alkyl (e.g., a methyl or an ethyl) and $R_7$ is L-RGM. In some embodiments, $R_7$ is L-Z (e.g., —$(CH_2)_m$—Z, where m is 1-12 and Z is selected from —H, —$CO_2H$, —$NH_2$, —$SO_3^-$, —$PO_3H$ and RGM.) In some embodiments, $R_{15}$ is a lower alkyl (e.g., a methyl or an ethyl) and $R_{16}$ is L-RGM. In some embodiments, $R_{16}$ is L-Z (e.g., —$(CH_2)_m$—Z, where m is 1-12 and Z is selected from —H, —$CO_2H$, —$NH_2$, —$SO_3^-$, —$PO_3H$ and RGM.)

In some embodiments, in Formula III, $R_8$, $R_9$ and $R_{17}$-$R_{22}$ are independently a hydrogen, an alkyl having 1-20 carbons, a hydroxy, an alkoxy having 1-20 carbons, a trifluoromethyl, a halogen, a methylthio, a carbonyl, an amino, a thiol, a sulfonate, a phosphonyl, or a L-RGM. In some instances, in Formula III, $R_8$, $R_9$ and $R_{17}$-$R_{22}$ are each independently a hydrogen or an alkyl having 1-20 carbons. In some instances, in Formula III, $R_8$, $R_9$ and $R_{17}$-$R_{22}$ are independently a hydrogen or L-RGM. In some instances, in Formula III, $R_8$ and $R_9$ are each hydrogen. In some instances, in Formula III, $R_{17}$-$R_{22}$ are each hydrogen. In certain embodiments, $R_9$ is cyclically linked to the adjacent N of the azaindoline ring, e.g., to form a 6 membered ring.

In some embodiments, in Formula III, $R_{10}$ and $R_{11}$ are each independently hydrogen, an alkyl, an aryl, an arylalkyl, a heteroaryl, a heteroarylalkyl, a carboxyalkyl, a sulfoalkyl, or a L-RGM. In certain embodiments, in Formula III, $R_{10}$ and $R_{11}$ are each independently hydrogen, an alkyl, an aryl or L-RGM.

In some instances, in Formula III, $R_{10}$ and $R_{11}$ are each independently an alkyl, such as a lower alkyl (e.g., methyl, ethyl, propyl, isopropyl, etc.). In certain instances, in Formula III, $R_{10}$ is L-RGM. In certain cases, in Formula II, $R_{11}$ is L-RGM.

In some embodiments, in Formula III, one or more of $R_4$ and $R_5$, $R_6$ and $R_7$, $R_5$ and $R_9$, $R_{15}$ and $R_{16}$, $R_4$ and $R_{22}$, $R_4$ and $R_6$/$R_7$, or $R_6$/$R_7$ and $R_{15}$/$R_{16}$ might be taken in combination to form a 5- to 50-membered ring (e.g., a 5- to 12-membered ring, such as a 5, 6, 7 or 8-membered ring).

In some cases, L is none, an alkyl, or a polyethyleneglycol.

In certain embodiments, RGM is a succinimidyl ester, or a maleimide.

In some instances, in Formula III, at least one of $R_1$-$R_{11}$ and $R_{15}$-$R_{22}$ includes a L-RGM. In certain embodiments, in Formula III, two of $R_1$-$R_{11}$ and $R_{15}$-$R_{22}$ include a L-RGM. In other instances, in Formula III, -RGM is optional.

In some instances, the dye compound is described by Formula IV:

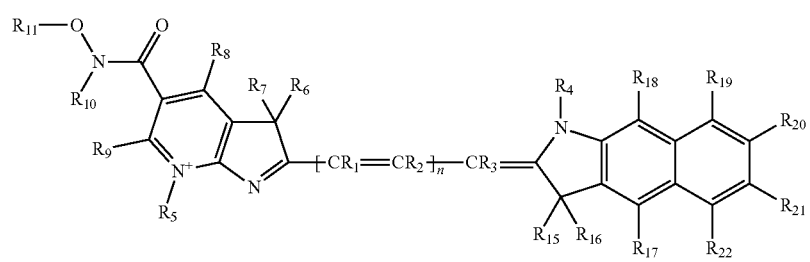

Formula IV where $R_1$-$R_3$ are each independently a hydrogen, a halogen, an alkyl having 1-20 carbons, a cycloalkyl having 3-20 carbons, an aryl, a heteroaryl, an amino, an alkylamino, an arylamino, a thiol, an alkylthiol, an arylthiol, a heteroarylthiol, a polyethyleneglycol, an alkoxy, an aryloxy, a carboxyalkyl, or a L-RGM; $R_4$ and $R_5$ are each independently an alkyl having 1-20 carbons, a cycloalkyl having 3-20 carbons, an arylalkyl, a heteroarylalkyl, a carboxyalkyl, a sulfoalkyl, or a L-RGM; $R_6$, $R_7$, $R_{15}$ and $R_{16}$ are each independently an alkyl having 1-20 carbons, a cycloalkyl having 3-20 carbons, an aryl, an arylalkyl, a heteroaryl, a heteroarylalkyl, a carboxyalkyl, a carboxyaryl, a sulfoalkyl, or a L-RGM; $R_8$, $R_9$ and $R_{17}$-$R_{22}$ are each independently a hydrogen, an alkyl having 1-20 carbons, a hydroxy, an alkoxy having 1-20 carbons, a trifluoromethyl, a halogen, a methylthio, a carbonyl, an amino, a thiol, a sulfonate, a phosphonyl, or a L-RGM; $R_{10}$ and $R_{11}$ are each independently a hydrogen, an alkyl, an aryl, an arylalkyl, a heteroaryl, a heteroarylalkyl, a carboxyalkyl, a sulfoalkyl, or a L-RGM; one or more of $R_4$ and $R_5$, $R_6$ and $R_7$, $R_5$ and $R_9$, $R_{15}$ and $R_{16}$, $R_4$ and $R_{18}$, $R_4$ and $R_6$/$R_7$, or $R_6$/$R_7$ and $R_{15}$/$R_{16}$ might be taken in combination to form a 5- to 50-membered ring.

In some embodiments, in Formula IV, n is 0. In some embodiments, in Formula IV, n is 1. In some embodiments, in Formula IV, n is 2. In some embodiments, in Formula IV, n is 3.

In certain cases, in Formula IV, $R_1$-$R_3$ are independently a hydrogen, a halogen, an alkyl having 1-20 carbons, a cycloalkyl having 3-20 carbons, an aryl, a heteroaryl, an amino, an alkylamino, an arylamino, a thiol, an alkylthiol, an arylthiol, a heteroarylthiol, a polyethyleneglycol, an alkoxy, an aryloxy, a carboxyalkyl, or a L-RGM. In certain instances, in Formula IV, $R_1$-$R_3$ are each a hydrogen. In certain cases, in Formula IV, two of $R_1$-$R_3$ are cyclically linked to form a six-membered carbocycle or heterocycle ring. In certain embodiments, in Formula IV, one of $R_1$-$R_3$ is an alkoxy, an aryloxy, or a L-RGM.

In some embodiments, in Formula IV, $R_4$ and $R_5$ are independently an alkyl having 1-20 carbons, a cycloalkyl having 3-20 carbons, an arylalkyl, a heteroarylalkyl, a carboxyalkyl, a sulfoalkyl, or a L-RGM. In certain embodiments, in Formula IV, $R_4$ and $R_5$ are each independently an alkyl having 1-20 carbons, a carboxyalkyl, a sulfoalkyl, or a L-RGM. In some cases, in Formula IV, $R_4$ and $R_5$ are each independently selected from an alkyl having 1-20 carbons, where the alkyl may be substituted with one or more substituents selected from a RGM, a sulfonate, a phosphate, amino, a substituted amino, an ammonium, a carboxy, and a hydroxyl. In certain embodiments, $R_4$ and $R_5$ are each independently selected from —$(CH_2)_m$—Z, where m is 1-12 and Z is selected from —H, —$CO_2H$, —$NH_2$, —$SO_3^-$, —$PO_3H$ and RGM.

In some embodiments, in Formula IV, $R_6$, $R_7$, $R_{15}$ and $R_{16}$ are independently an alkyl having 1-20 carbons, a cycloalkyl having 3-20 carbons, an aryl, an arylalkyl, a heteroaryl, a heteroarylalkyl, a carboxyalkyl, a carboxyaryl, a sulfoalkyl, or a L-RGM. In certain instances, in Formula IV, $R_6$, $R_7$, $R_{15}$ and $R_{16}$ are each independently an alkyl having 1-20 carbons. In certain instances, in Formula IV, $R_6$, $R_7$, $R_{15}$ and $R_{16}$ are each independently a lower alkyl. In certain instances, in Formula IV, $R_6$ and $R_7$ are each methyl. In certain instances, in Formula IV, $R_{15}$ and $R_{16}$ are each methyl. In some embodiments, $R_6$ is a lower alkyl (e.g., a methyl or an ethyl) and $R_7$ is L-RGM. In some embodiments, $R_7$ is L-Z (e.g., —$(CH_2)_m$—Z, where m is 1-12 and Z is selected from —H, —$CO_2H$, —$NH_2$, —$SO_3^-$, —$PO_3H$ and RGM.) In some embodiments, $R_{15}$ is a lower alkyl (e.g., a methyl or an ethyl) and $R_{16}$ is L-RGM. In some embodiments, $R_{16}$ is L-Z (e.g., —$(CH_2)_m$—Z, where m is 1-12 and Z is selected from —H, —$CO_2H$, —$NH_2$, —$SO_3^-$, —$PO_3H$ and RGM.)

In some embodiments, in Formula IV, $R_8$, $R_9$ and $R_{17}$-$R_{22}$ are independently a hydrogen, an alkyl having 1-20 carbons, a hydroxy, an alkoxy having 1-20 carbons, a trifluoromethyl, a halogen, a methylthio, a carbonyl, an amino, a thiol, a sulfonate, a phosphonyl, or a L-RGM. In some instances, in Formula IV, $R_8$, $R_9$ and $R_{17}$-$R_{22}$ are each independently a hydrogen or an alkyl having 1-20 carbons. In some instances, in Formula IV, $R_8$, $R_9$ and $R_{17}$-$R_{22}$ are independently a hydrogen or L-RGM. In some instances, in Formula IV, $R_8$ and $R_9$ are each hydrogen. In some instances, in Formula IV, $R_{17}$-$R_{22}$ are each hydrogen. In certain embodiments, $R_9$ is cyclically linked to the adjacent N of the azaindoline ring, e.g., to form a 6 membered ring.

In some embodiments, in Formula IV, $R_{10}$ and $R_{11}$ are each independently hydrogen, an alkyl, an aryl, an arylalkyl, a heteroaryl, a heteroarylalkyl, a carboxyalkyl, a sulfoalkyl, or a L-RGM. In certain embodiments, in Formula IV, $R_{10}$ and $R_{11}$ are each independently hydrogen, an alkyl, an aryl or L-RGM. In some instances, in Formula IV, $R_{10}$ and $R_{11}$ are each independently an alkyl, such as a lower alkyl (e.g., methyl, ethyl, propyl, isopropyl, etc.). In certain instances, in Formula IV, $R_{10}$ is L-RGM. In certain cases, in Formula II, $R_{11}$ is L-RGM.

In some embodiments, in Formula IV, one or more of $R_4$ and $R_5$, $R_6$ and $R_7$, $R_5$ and $R_9$, $R_{15}$ and $R_{16}$, $R_4$ and $R_{22}$, $R_4$ and $R_6$/$R_7$, or $R_6$/$R_7$ and $R_{15}$/$R_{16}$ might be taken in combination to form a 5- to 50-membered ring (e.g., a 5- to 12-membered ring, such as a 5, 6, 7 or 8-membered ring).

In some cases, L is none, an alkyl, or a polyethyleneglycol.

In certain embodiments, RGM is a succinimidyl ester, or a maleimide.

In some instances, in Formula IV, at least one of $R_1$-$R_{11}$ and $R_{15}$-$R_{22}$ includes a L-RGM. In certain embodiments, in Formula IV, two of $R_1$-$R_{11}$ and $R_{15}$-$R_{22}$ include a L-RGM. In other instances, in Formula IV, -RGM is optional.

In some embodiments, the dye compound is described by Formula V:

Formula V

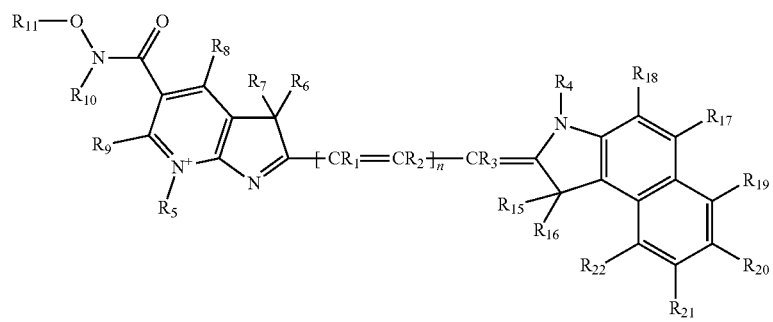

where, n is 0 to 3; $R_1$-$R_3$ are each independently a hydrogen, a halogen, an alkyl having 1-20 carbons, a cycloalkyl having 3-20 carbons, an aryl, a heteroaryl, an amino, an alkylamino, an arylamino, a thiol, an alkylthiol, an arylthiol, a heteroarylthiol, a polyethyleneglycol, an alkoxy, an aryloxy, a carboxyalkyl, a phosphonylalkyl, sulfonylalkyl, or a L-RGM; $R_4$ and $R_5$ are each independently an alkyl having 1-20 carbons, a cycloalkyl having 3-20 carbons, an arylalkyl, a heteroarylalkyl, a carboxyalkyl, a sulfoalkyl, a phosphonylalkyl, or a L-RGM; $R_6$, $R_7$, $R_{15}$ and $R_{16}$ are each independently an alkyl having 1-20 carbons, a cycloalkyl having 3-20 carbons, an aryl, an arylalkyl, a heteroaryl, a heteroarylalkyl, a carboxyalkyl, carboxylaryl, a phosphonylalkyl, a sulfoalkyl, or a L-RGM; $R_8$, $R_9$ and $R_{17}$-$R_{22}$ are each independently a hydrogen, an alkyl having 1-20 carbons, a hydroxy, an alkoxy having 1-20 carbons, a trifluoromethyl, a halogen, a methylthio, a carbonyl, an amino, a thiol, a sulfonate, a phosphonyl, or a L-RGM; $R_{10}$ and $R_{11}$ are each independently a hydrogen, an alkyl, an aryl, an arylalkyl, a heteroaryl, a heteroarylalkyl, a carboxyalkyl, a phosphonylalkyl, a sulfoalkyl, or a L-RGM; RGM is a chemically reactive group; L is a linker; and optionally, one or more of $R_4$ and $R_5$, $R_6$ and $R_7$, $R_5$ and $R_9$, $R_{15}$ and $R_{16}$, $R_4$ and $R_{18}$, $R_4$ and $R_6$/$R_7$, or $R_6$/$R_7$ and $R_{15}$/$R_{16}$ is taken in combination to form a 5- to 50-membered ring.

In certain cases, in formula V, $R_1$-$R_3$ are each independently a hydrogen, or a L-RGM; $R_4$ and $R_5$ are each independently an alkyl having 1-20 carbons, a carboxyalkyl, a sulfoalkyl, or a L-RGM; $R_6$, $R_7$, $R_{15}$ and $R_{16}$ are each independently an alkyl having 1-20 carbons, a cycloalkyl having 3-20 carbons, a carboxyalkyl, a carboxylaryl, a sulfoalkyl, or a L-RGM; $R_8$, $R_9$ and $R_{17}$-$R_{22}$ are each independently a hydrogen, an alkyl having 1-20 carbons, a sulfonate, or a L-RGM; and $R_{10}$ and $R_{11}$ are each independently an alkyl, a carboxyalkyl, or a L-RGM.

In some embodiments, in formula V, $R_1$-$R_3$ are each hydrogen; $R_4$ and $R_5$ are independently an alkyl having 1-20 carbons, a carboxyalkyl, a sulfoalkyl, or a L-RGM; $R_6$, $R_7$, $R_{15}$ and $R_{16}$ are each independently an alkyl having 1-20 carbons, a cycloalkyl having 3-20 carbons, an aryl, an arylalkyl, a carboxyalkyl, a carboxylaryl, a sulfoalkyl, or a L-RGM; $R_8$, $R_9$ and $R_{17}$-$R_{22}$ are each independently a hydrogen or a sulfonate; and $R_{10}$ and $R_{11}$ are each independently an alkyl, or a L-RGM.

In some cases, L is none, an alkyl, or a polyethyleneglycol.

In certain embodiments, RGM is a succinimidyl ester, or a maleimide.

In some embodiments, in Formula V, n is 0. In some embodiments, in Formula V, n is 1. In some embodiments, in Formula V, n is 2. In some embodiments, in Formula V, n is 3.

In certain cases, in Formula V, $R_1$-$R_3$ are independently a hydrogen, a halogen, an alkyl having 1-20 carbons, a cycloalkyl having 3-20 carbons, an aryl, a heteroaryl, an amino, an alkylamino, an arylamino, a thiol, an alkylthiol, an arylthiol, a heteroarylthiol, a polyethyleneglycol, an alkoxy, an aryloxy, a carboxyalkyl, or a L-RGM. In certain instances, in Formula V, $R_1$-$R_3$ are each a hydrogen. In certain cases, in Formula V, two of $R_1$-$R_3$ are cyclically linked to form a six-membered carbocycle or heterocycle ring. In certain embodiments, in Formula V, one of $R_1$-$R_3$ is an alkoxy, an aryloxy, or a L-RGM.

In some embodiments, in Formula V, $R_4$ and $R_5$ are independently an alkyl having 1-20 carbons, a cycloalkyl having 3-20 carbons, an arylalkyl, a heteroarylalkyl, a carboxyalkyl, a sulfoalkyl, or a L-RGM. In certain embodiments, in Formula V, $R_4$ and $R_5$ are each independently an alkyl having 1-20 carbons, a carboxyalkyl, a sulfoalkyl, or a L-RGM. In some cases, in Formula V, $R_4$ and $R_5$ are each independently selected from an alkyl having 1-20 carbons, where the alkyl may be substituted with one or more substituents selected from a RGM, a sulfonate, a phosphate, amino, a substituted amino, an ammonium, a carboxy, and a hydroxyl. In certain embodiments, $R_4$ and $R_5$ are each independently selected from —$(CH_2)_m$—Z, where m is 1-12 and Z is selected from —H, —$CO_2H$, —$NH_2$, —$SO_3^-$, —$PO_3H$ and RGM.

In some embodiments, in Formula V, $R_6$, $R_7$, $R_{15}$ and $R_{16}$ are independently an alkyl having 1-20 carbons, a cycloalkyl having 3-20 carbons, an aryl, an arylalkyl, a heteroaryl, a heteroarylalkyl, a carboxyalkyl, a carboxyaryl, a sulfoalkyl, or a L-RGM. In certain instances, in Formula V, $R_6$, $R_7$, $R_{15}$ and $R_{16}$ are each independently an alkyl having 1-20 carbons. In certain instances, in Formula V, $R_6$, $R_7$, $R_{15}$ and $R_{16}$ are each independently a lower alkyl. In certain instances, in Formula V, $R_6$ and $R_7$ are each methyl. In certain instances, in Formula V, $R_{15}$ and $R_{16}$ are each methyl. In some embodiments, $R_6$ is a lower alkyl (e.g., a methyl or an ethyl) and $R_7$ is L-RGM. In some embodiments, $R_7$ is L-Z (e.g., —$(CH_2)_m$—Z, where m is 1-12 and Z is selected from —H, —$CO_2H$, —$NH_2$, —$SO_3^-$, —$PO_3H$ and RGM.) In some embodiments, $R_{15}$ is a lower alkyl (e.g., a methyl or an ethyl) and $R_{16}$ is L-RGM. In some embodiments, $R_{16}$ is L-Z (e.g., —$(CH_2)_m$—Z, where m is 1-12 and Z is selected from —H, —$CO_2H$, —$NH_2$, —$SO_3^-$, —$PO_3H$ and RGM.)

In some embodiments, in Formula V, $R_8$, $R_9$ and $R_{17}$-$R_{22}$ are independently a hydrogen, an alkyl having 1-20 carbons, a hydroxy, an alkoxy having 1-20 carbons, a trifluoromethyl, a halogen, a methylthio, a carbonyl, an amino, a thiol, a sulfonate, a phosphonyl, or a L-RGM. In some instances, in Formula V, $R_8$, $R_9$ and $R_{17}$-$R_{22}$ are each independently a hydrogen or an alkyl having 1-20 carbons. In some instances, in Formula V, $R_8$, $R_9$ and $R_{17}$-$R_{22}$ are independently a hydrogen or L-RGM. In some instances, in Formula V, $R_8$ and $R_9$ are each hydrogen. In some instances, in Formula V, $R_{17}$-$R_{22}$ are each hydrogen. In certain embodiments, $R_9$ is cyclically linked to the adjacent N of the azaindoline ring, e.g., to form a 6 membered ring.

In some embodiments, in Formula V, $R_{10}$ and $R_{11}$ are each independently hydrogen, an alkyl, an aryl, an arylalkyl, a heteroaryl, a heteroarylalkyl, a carboxyalkyl, a sulfoalkyl, or a L-RGM. In certain embodiments, in Formula V, $R_{10}$ and $R_{11}$ are each independently hydrogen, an alkyl, an aryl or L-RGM. In some instances, in Formula V, $R_{10}$ and $R_{11}$ are each independently an alkyl, such as a lower alkyl (e.g., methyl, ethyl, propyl, isopropyl, etc.). In certain instances, in Formula V, $R_{10}$ is L-RGM. In certain cases, in Formula II, $R_{11}$ is L-RGM.

In some embodiments, in Formula V, one or more of $R_4$ and $R_5$, $R_6$ and $R_7$, $R_5$ and $R_9$, $R_{15}$ and $R_{16}$, $R_4$ and $R_{22}$, $R_4$ and $R_6$/$R_7$, or $R_6$/$R_7$ and $R_{15}$/$R_{16}$ might be taken in combination to form a 5- to 50-membered ring (e.g., a 5- to 12-membered ring, such as a 5, 6, 7 or 8-membered ring).

In some instances, in Formula V, at least one of $R_1$-$R_{11}$ and $R_{15}$-$R_{22}$ includes a L-RGM. In certain embodiments, in Formula V, two of $R_1$-$R_{11}$ and $R_{15}$-$R_{22}$ include a L-RGM. In other instances, in Formula V, -RGM is optional.

In certain instances, the dye compound is described by Formula VI:

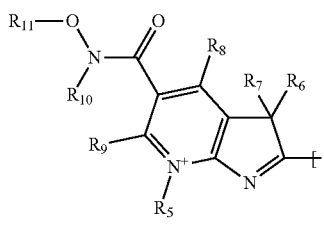
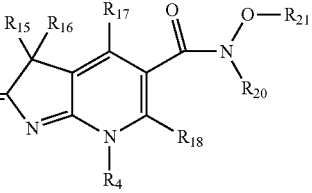

Formula VI where: n is 0, 1, 2 or 3; $R_1$-$R_3$ are each independently a hydrogen, a halogen, an alkyl having 1-20 carbons, a cycloalkyl having 3-20 carbons, an aryl, a heteroaryl, an amino, an alkylamino, an arylamino, a thiol, an alkylthiol, an arylthiol, a heteroarylthiol, a polyethyleneglycol, an alkoxy, an aryloxy, a carboxyalkyl, or a L-RGM; $R_4$ and $R_5$ are each independently an alkyl having 1-20 carbons, a cycloalkyl having 3-20 carbons, an arylalkyl, a heteroarylalkyl, a carboxyalkyl, a sulfoalkyl, or a L-RGM; $R_6$, $R_7$, $R_{15}$ and $R_{16}$ are each independently an alkyl having 1-20 carbons, a cycloalkyl having 3-20 carbons, an aryl, an arylalkyl, a heteroaryl, a heteroarylalkyl, a carboxyalkyl, a carboxylaryl, a sulfoalkyl, or a L-RGM; $R_8$, $R_9$, $R_{17}$ and $R_{18}$ are each independently a hydrogen, an alkyl having 1-20 carbons, a hydroxy, an alkoxy having 1-20 carbons, a trifluoromethyl, a halogen, a methylthio, a carbonyl, an amino, a thiol, a sulfonate, a phosphonyl, or a L-RGM; $R_{10}$, $R_{11}$, $R_{20}$ and $R_{21}$ are each independently a hydrogen, an alkyl, an aryl, an arylalkyl, a heteroaryl, a heteroarylalkyl, a carboxyalkyl, a sulfoalkyl, or a L-RGM; RGM is a chemically reactive group; L is a linker; and optionally, one or more of $R_4$ and $R_5$, $R_6$ and $R_7$, $R_8$ and $R_9$, $R_{15}$ and $R_{16}$, $R_4$ and $R_{18}$, $R_4$ and $R_6$/$R_7$, or $R_6$/$R_7$ and $R_{15}$/$R_{16}$ is taken in combination to form a 5- to 50-membered ring.

In certain cases, $R_1$-$R_3$ are each hydrogen. In certain cases, in Formula VI, two of $R_1$-$R_3$ are cyclically linked to form a six-membered carbocycle or heterocycle ring. In certain embodiments, in Formula VI, one of $R_1$-$R_3$ is an alkoxy, an aryloxy, or a L-RGM.

In some cases, in Formula VI, $R_4$ and $R_5$ are each independently selected from an alkyl having 1-20 carbons, where the alkyl may be substituted with one or more substituents selected from a RGM, a sulfonate, a phosphate, amino, a substituted amino, an ammonium, a carboxy, and a hydroxyl. In certain embodiments, $R_4$ and $R_5$ are each independently selected from $—(CH_2)_m—Z$, where m is 1-12 and Z is selected from $—H$, $—CO_2H$, $—NH_2$, $—SO_3^-$, $—PO_3H$ and RGM.

In certain instances, in Formula VI, $R_6$ and $R_7$ are each independently an alkyl having 1-20 carbons. In certain instances, in Formula VI, $R_6$ and $R_7$ are each independently a lower alkyl. In certain instances, in Formula VI, $R_6$ and $R_7$ are each methyl. In some embodiments, $R_6$ is a lower alkyl (e.g., a methyl or an ethyl) and $R_7$ is L-RGM. In some embodiments, $R_7$ is L-Z (e.g., $—(CH_2)_m—Z$, where m is 1-12 and Z is selected from $—H$, $—CO_2H$, $—NH_2$, $—SO_3^-$, $—PO_3H$ and RGM).

In some instances, in Formula VI, $R_8$ and $R_9$ are each independently a hydrogen or an alkyl having 1-20 carbons. In some instances, in Formula VI, $R_8$ and $R_9$ are each independently a hydrogen or L-RGM. In some instances, in Formula VI, $R_8$ and $R_9$ are each hydrogen. In certain embodiments, $R_9$ is cyclically linked to the adjacent N of the azaindoline ring, e.g., to form a 6 membered ring.

In some instances, in Formula VI, $R_{17}$ and $R_{18}$ are each independently a hydrogen or an alkyl having 1-20 carbons. In some instances, in Formula VI, $R_{17}$ and $R_{18}$ are each independently a hydrogen or L-RGM. In some instances, in Formula VI, $R_{17}$ and $R_{18}$ are each hydrogen. In certain embodiments, $R_{18}$ is cyclically linked to the adjacent N—R4 of the azaindoline ring, e.g., to form a 6 membered ring.

In some instances, in formula VI, $R_1$-$R_3$ are each independently a hydrogen, or a L-RGM; $R_4$ and $R_5$ are each independently an alkyl having 1-20 carbons, a carboxyalkyl, a sulfoalkyl, or a L-RGM; $R_6$, $R_7$, $R_{15}$ and $R_{16}$ are each independently an alkyl having 1-20 carbons, a cycloalkyl having 3-20 carbons, an aryl, an arylalkyl, a carboxyalkyl, carboxylaryl, a sulfoalkyl, or a L-RGM; $R_8$, $R_9$ and $R_{17}$-$R_{22}$ are each independently a hydrogen, an alkyl having 1-20 carbons, a sulfonate, a phosphonyl or a L-RGM; and $R_{10}$ and $R_{11}$ are each independently an alkyl, an aryl, an arylalkyl, a carboxyalkyl, a sulfoalkyl, or a L-RGM.

In certain instances, in formula VI, $R_1$-$R_3$ are each hydrogen; $R_4$ and $R_5$ are each independently an alkyl having 1-20 carbons, a carboxyalkyl, a sulfoalkyl, or a L-RGM; $R_6$, $R_7$, $R_{15}$ and $R_{16}$ are each independently an alkyl having 1-20 carbons, a cycloalkyl having 3-20 carbons, a carboxyalkyl, a carboxylaryl, a sulfoalkyl, or a L-RGM; $R_8$, $R_9$, $R_{17}$, and $R_{18}$ are each independently a hydrogen, or a sulfonate; and $R_{10}$ and $R_{11}$ are each independently an alkyl, or a L-RGM.

In certain cases, in formula VI, L is none, an alkyl, or a polyethyleneglycol.

In certain embodiments, in formula VI, RGM is a succinimidyl ester, or a maleimide.

In some cases, in Formula VI, n is 0. In some instances, in Formula VI, n is 1. In certain cases, in Formula VI, n is 2. In some cases, in Formula VI, n is 3.

In certain embodiments, in Formula VI, at least one of $R_1$-$R_{11}$, $R_{15}$-$R_{18}$ and $R_{17}$-$R_{21}$ includes a L-RGM. In certain embodiments, in Formula VI, two of $R_1$-$R_{11}$, $R_{15}$-$R_{18}$ and $R_{17}$-$R_{21}$ include a L-RGM.

In certain embodiments, in Formulae I-VI, $R_{11}$ includes a L-RGM. In certain embodiments, in Formulae I-VI, $R_4$ includes a L-RGM. In certain instances, in Formulae I-VI, at least one of $R_{15}$ and $R_{16}$ includes a L-RGM.

In certain instances, in Formulae I-VI, $R_6$ and $R_7$ are methyl. In certain instances, in Formulae I-VI, $R_{15}$ and $R_{16}$ are methyl.

In some embodiments, in Formulae I-VI, $R^4$ and $R^5$ are each independently $—(CH_2)_q—Z$, wherein Z is a water-soluble group and q is an integer from 1 to 12. In certain embodiments, Z is $SO_3H$ and n is 3.

In some embodiments, in Formulae II-VI, $R^{15}$ is a lower alkyl and $R^{16}$ is $—(CH_2)_m—Y$-RGM, where Y is a cycloalkyl, a heterocycloalkyl, a heterocycle, or an aryl and m is 0 or an integer from 1 to 6. In some instances, Y is a phenyl, a pyridyl, a cyclohexyl, or a piperidinyl. In certain embodiments, $R^{15}$ is methyl. In certain instances, RGM is an active ester. In some cases, Y is phenyl. In certain embodiments, $R^{16}$ is —$(CH_2)_m$-Ph-C(O)—NHS, where m is 0 or 1 and NHS is N-hydroxy succinimidyl.

In certain cases, in Formulae I-VI, $R^6$ and $R^7$ are each independently a lower alkyl. In certain instances, $R^6$ and $R^7$ are each methyl.

In certain embodiments, the dye compound does not include a PEG-containing substituent. In certain embodiments, the dye compound does not include a water-soluble polyalkylene oxide polymer of MW 300 to 5000.

In certain embodiments, the dye compound does not include a cleavable linker. In certain embodiments, the dye compound does not include a linker that includes a labile —C=N— group. In some instances, the dye compound is described by one of the following structures:

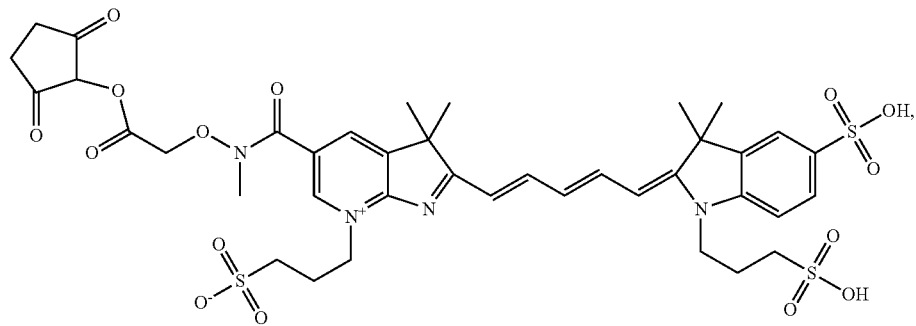

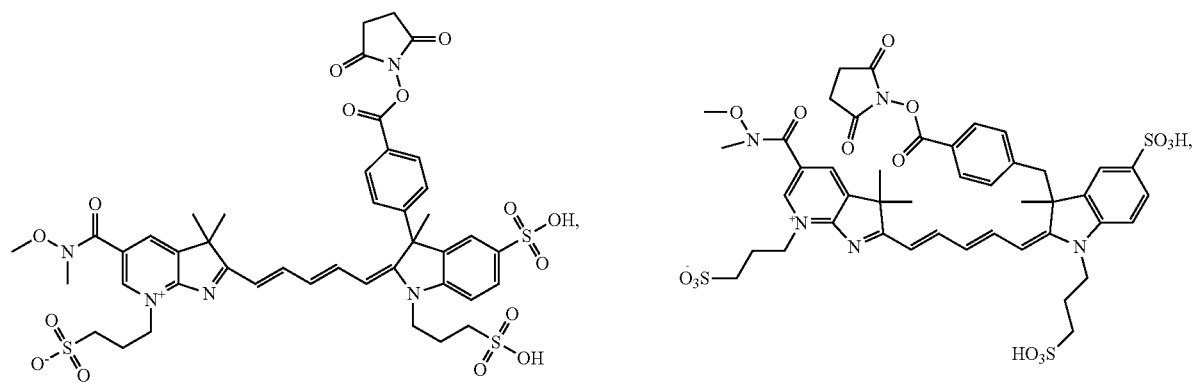

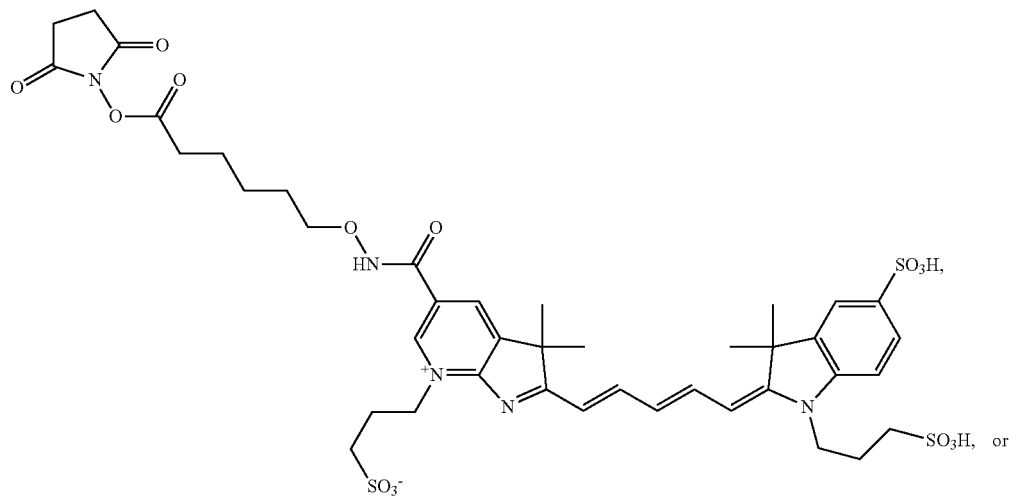

-continued

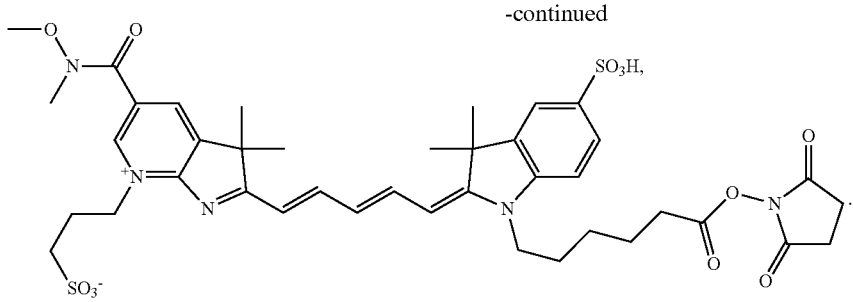

The dyes with a L-RGM label a wide variety of organic or inorganic substances that contain or are modified to contain functional groups with suitable reactivity, resulting in chemical attachment of the conjugated substance. Some embodiments of the reactive dyes of the present disclosure are given in Table 1, below. The number of the reactive dyes in Table 1 corresponds to the numbering of the compounds described in the examples.

TABLE 1

Exemplary Reactive Cyanine Dyes

| Dye | Structure |
|---|---|
| 12 | 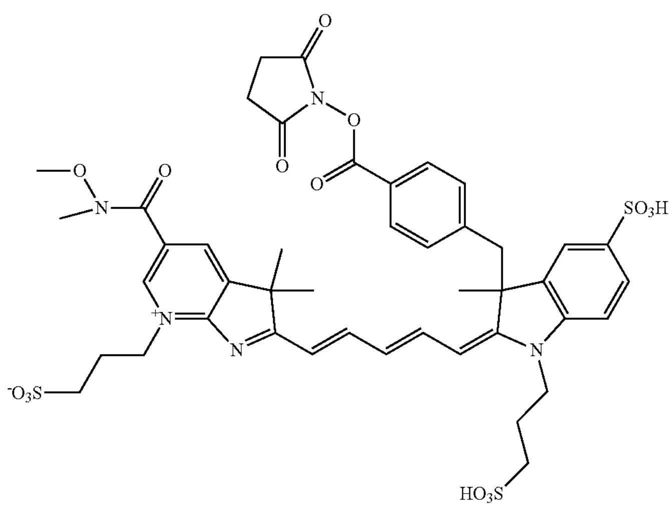 |
| 22 | 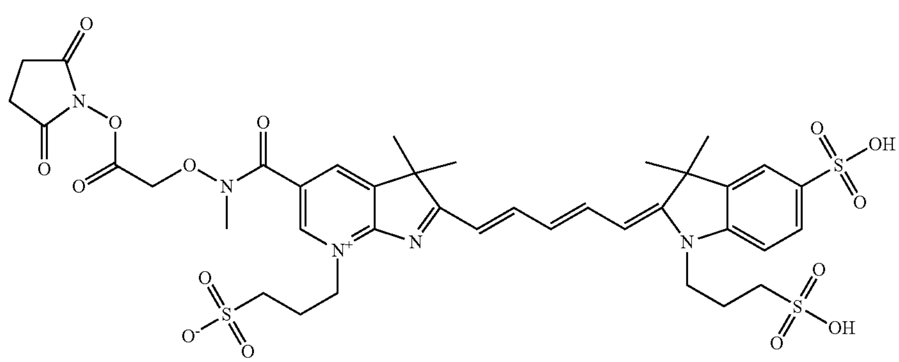 [SMILES: CN(OCC(=O)ON1C(=O)CCC1=O)C(=O)c1cc2c([n+](CCCS(=O)(=O)[O-])c1)N=C(/C=C/C=C/C=C1/N(CCCS(=O)(=O)O)c3ccc(S(=O)(=O)O)cc3C1(C)C)C2(C)C] |

TABLE 1-continued
Exemplary Reactive Cyanine Dyes
| Dye | Structure |
|---|---|
| 24 | 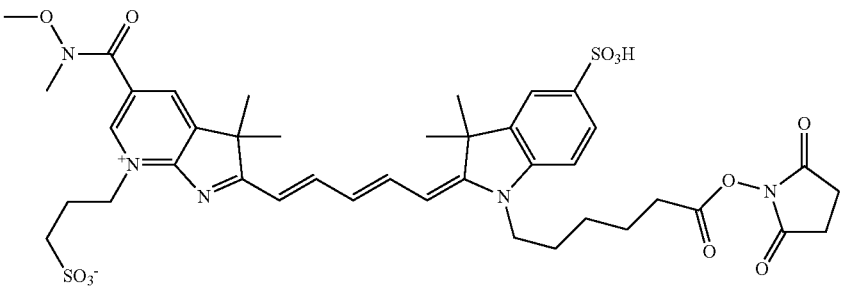 |
| 26 | 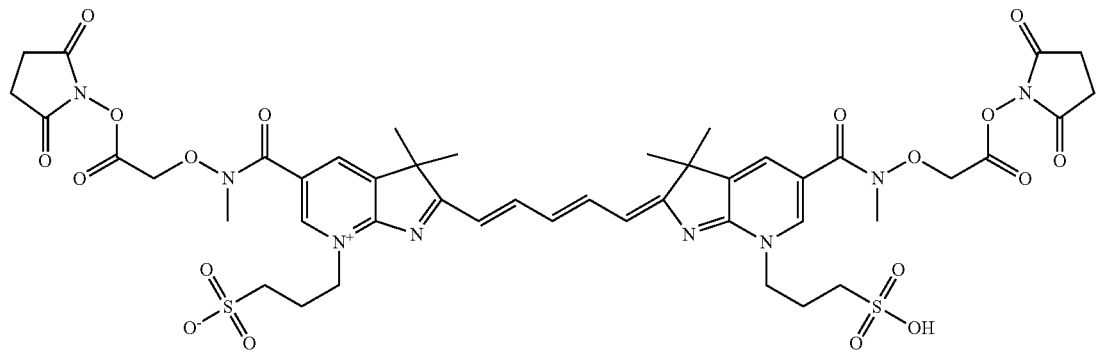 [SMILES: CN(OCC(=O)ON1C(=O)CCC1=O)C(=O)C1=CN(CCCS(=O)(=O)O)C2=N/C(=C/C=C/C=C/C3=Nc4c(cc(C(=O)N(C)OCC(=O)ON5C(=O)CCC5=O)c[n+]4CCCS(=O)(=O)[O-])C3(C)C)C(C)(C)C2=C1] |
| 29 | 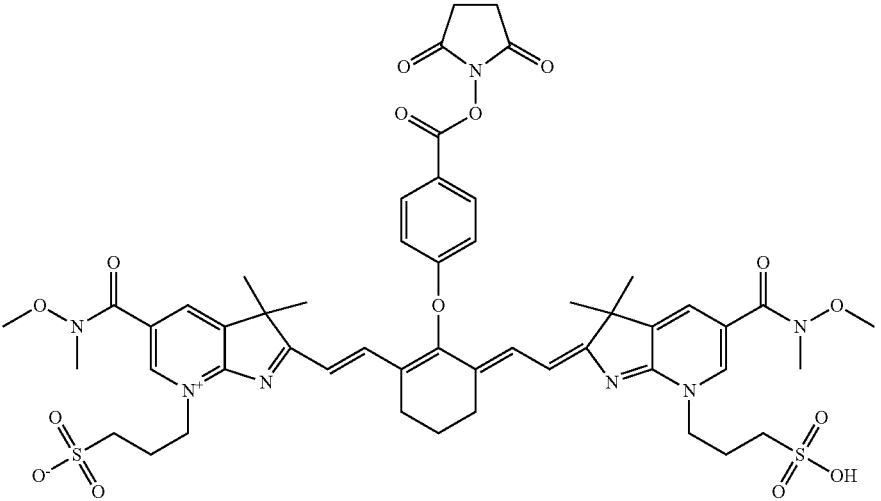 |

TABLE 1-continued
Exemplary Reactive Cyanine Dyes
| Dye | Structure |
|---|---|
| 33 | 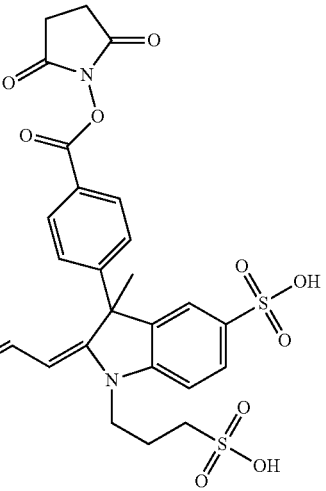 |
| 34 | 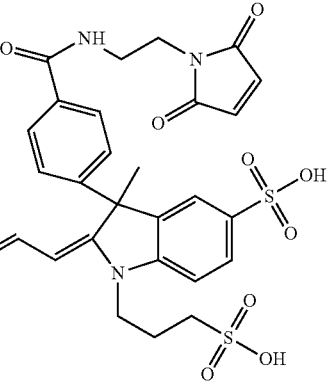 |
| 35 | 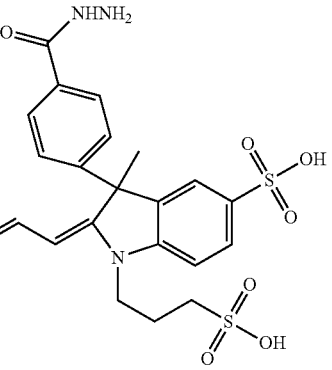 |

TABLE 1-continued
Exemplary Reactive Cyanine Dyes
| Dye | Structure |
|---|---|
| 40 | 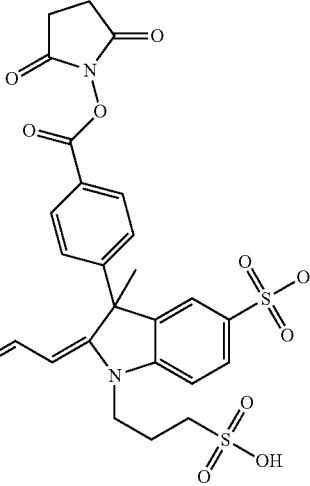 |
| 41 | 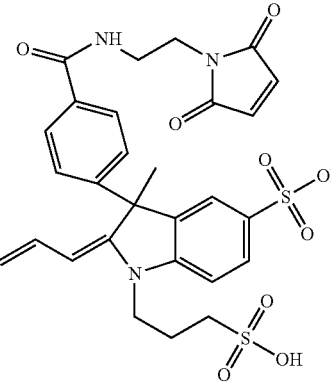 |
| 42 | 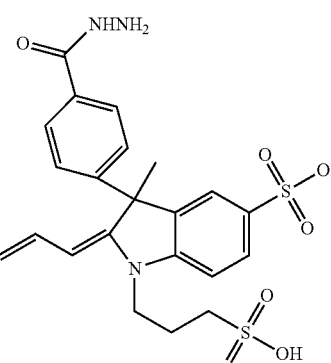 |

US 9,012,643 B2
47
48
TABLE 1-continued
Exemplary Reactive Cyanine Dyes
| Dye | Structure |
|---|---|
| 45 | 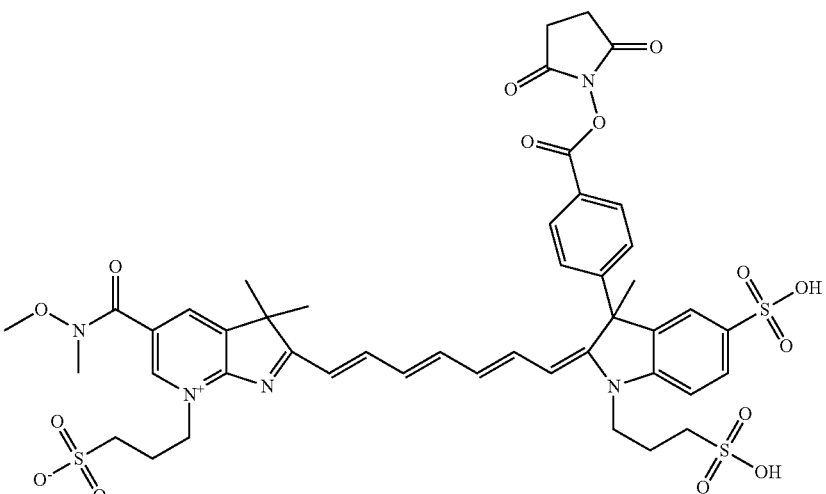 |
| 46 | 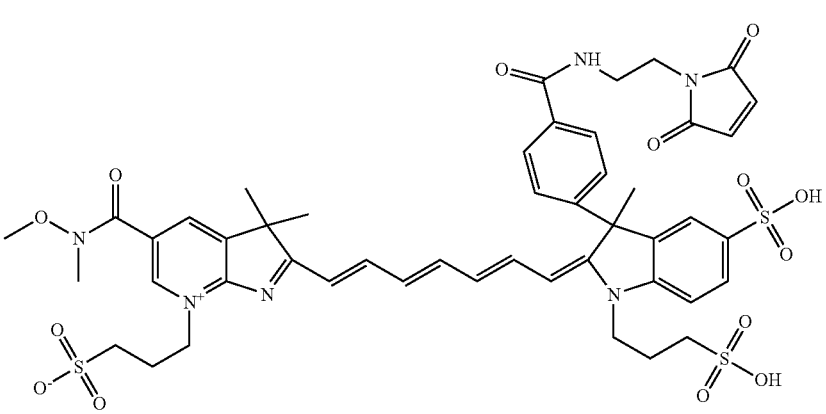 [SMILES: CON(C)C(=O)c1cc2c([n+](CCCS(=O)(=O)[O-])c1)N=C(/C=C/C=C/C=C/C=C1/N(CCCS(=O)(=O)O)c3ccc(S(=O)(=O)O)cc3C1(C)c1ccc(C(=O)NCCN3C(=O)C=CC3=O)cc1)C2(C)C] |
| 47 | 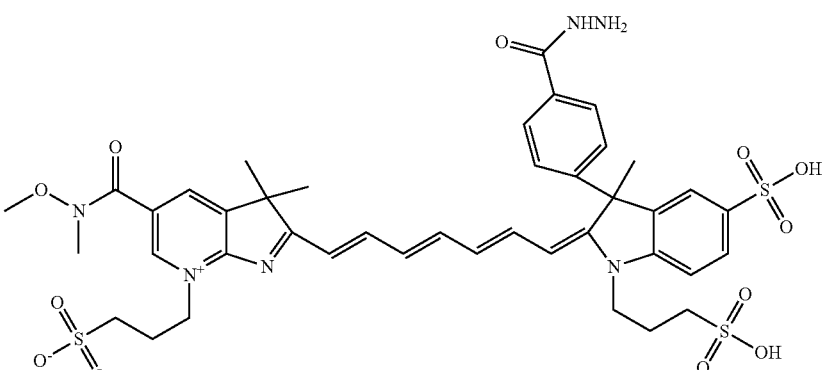 |

TABLE 1-continued

Exemplary Reactive Cyanine Dyes

| Dye | Structure |
|---|---|
| 48 | 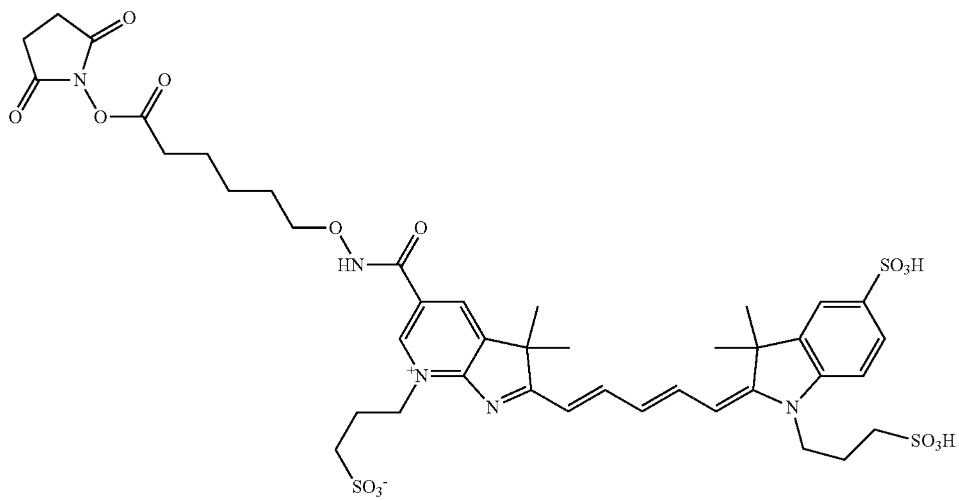 |
| 49 | 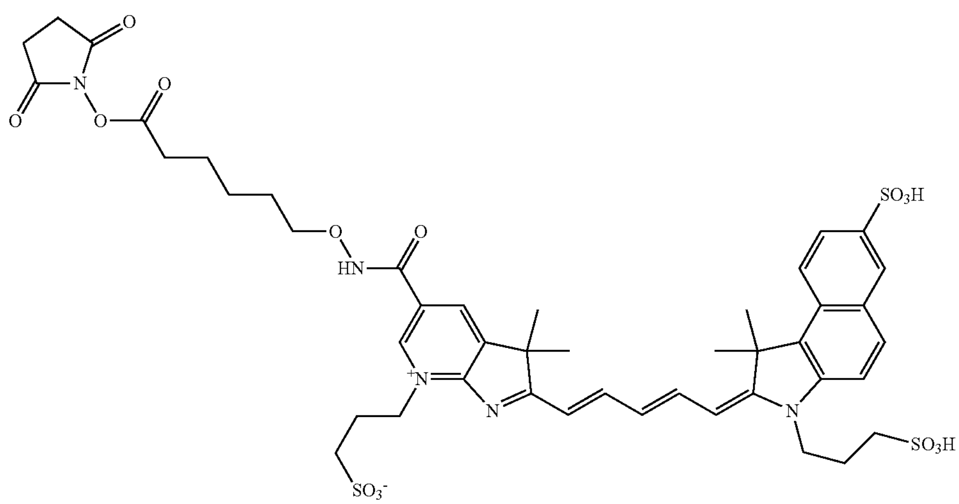 |
| 50 | 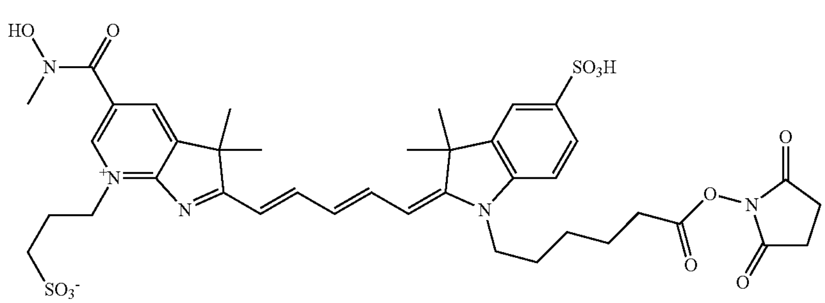 |

US 9,012,643 B2
51 52
TABLE 1-continued
Exemplary Reactive Cyanine Dyes
| Dye | Structure |
|-----|-----------|
| 51 | 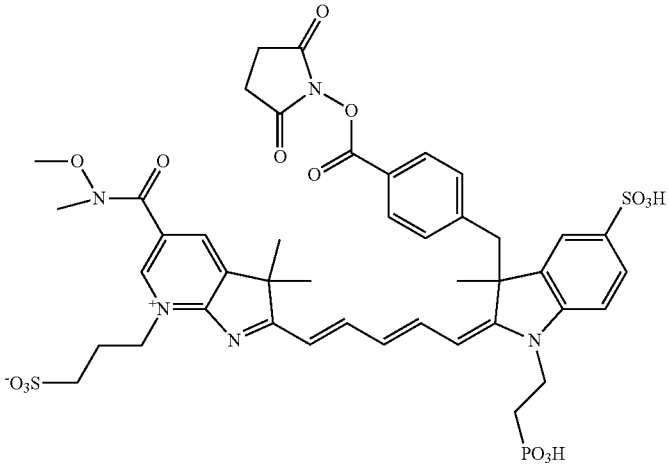 |
| 52 | 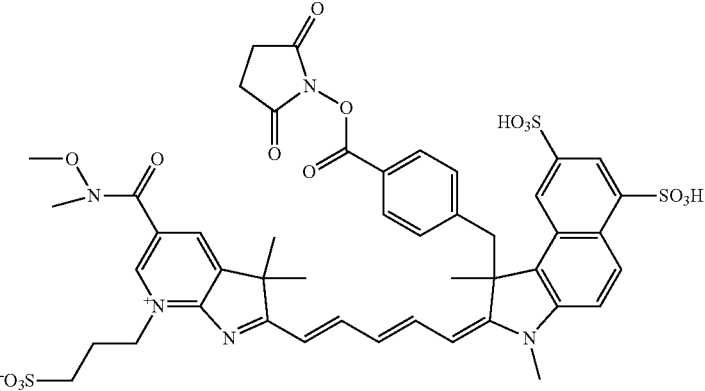 |
| 53 | 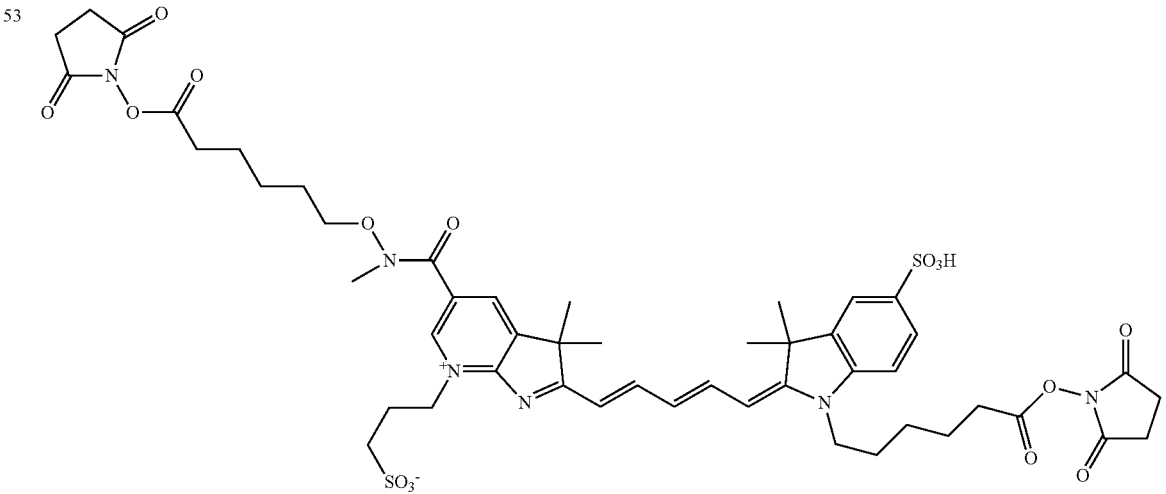 |

TABLE 1-continued

Exemplary Reactive Cyanine Dyes

| Dye | Structure |
|---|---|
| 54 | 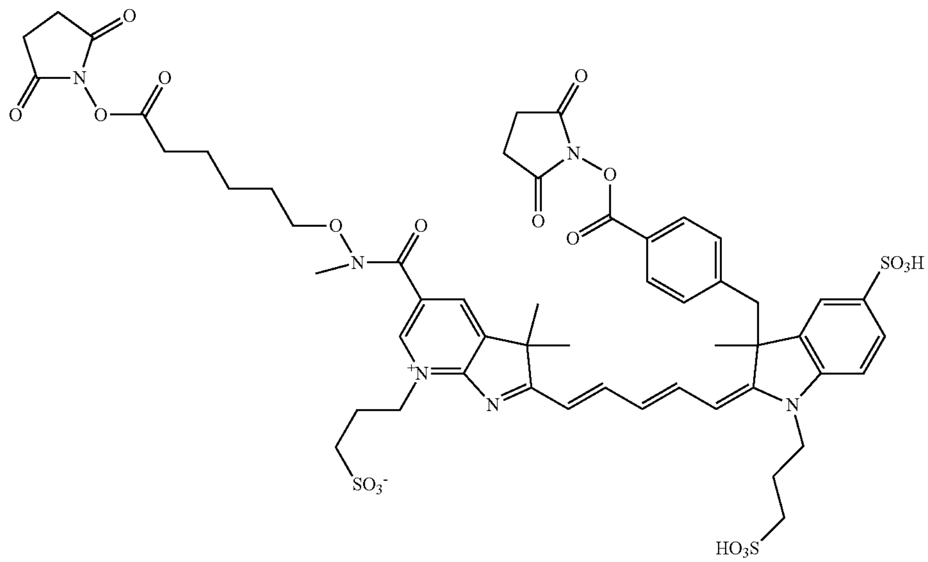 |
| 55 | 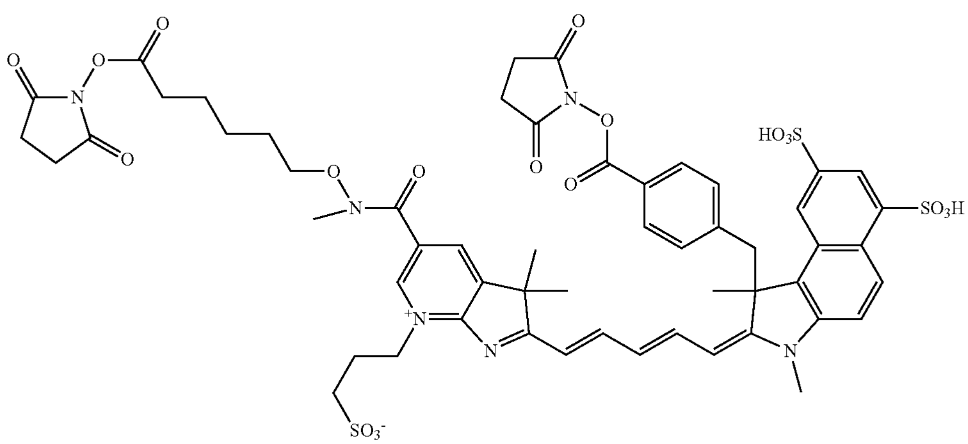 |
| 60 | 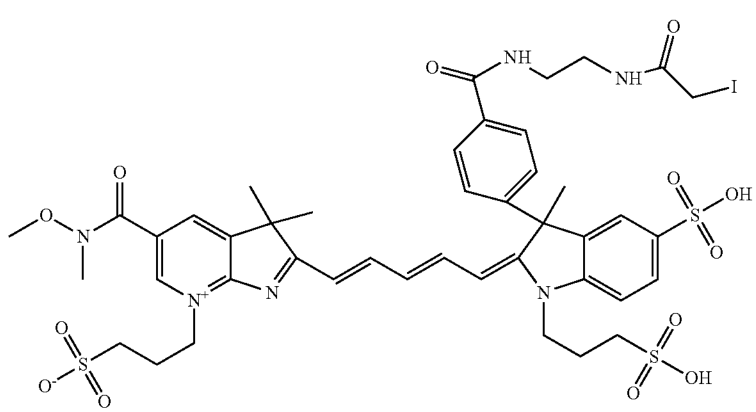 [SMILES: CON(C)C(=O)c1cc2c([n+](CCCS(=O)(=O)[O-])c1)N=C(/C=C/C=C/C=C1/N(CCCS(=O)(=O)O)c3ccc(S(=O)(=O)O)cc3C1(C)c1ccc(C(=O)NCCNC(=O)CI)cc1)C2(C)C] |

TABLE 1-continued

Exemplary Reactive Cyanine Dyes

| Dye | Structure |
|---|---|
| 61 | 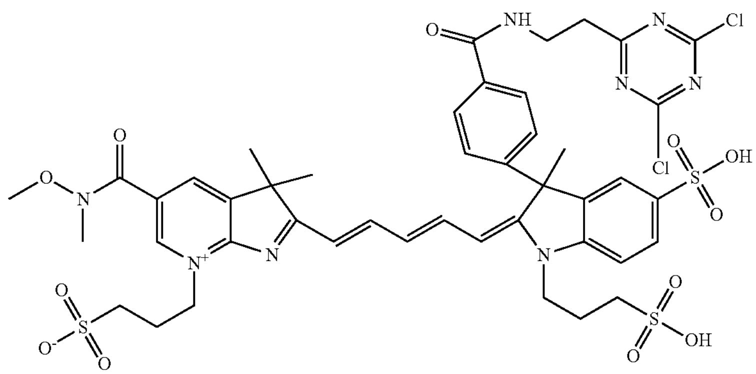 [SMILES: CON(C)C(=O)c1cc2c([n+](CCCS(=O)(=O)[O-])c1)N=C(/C=C/C=C/C=C1/N(CCCS(=O)(=O)O)c3ccc(S(=O)(=O)O)cc3C1(C)c1ccc(C(=O)NCCc3nc(Cl)nc(Cl)n3)cc1)C2(C)C] |
| 62 | 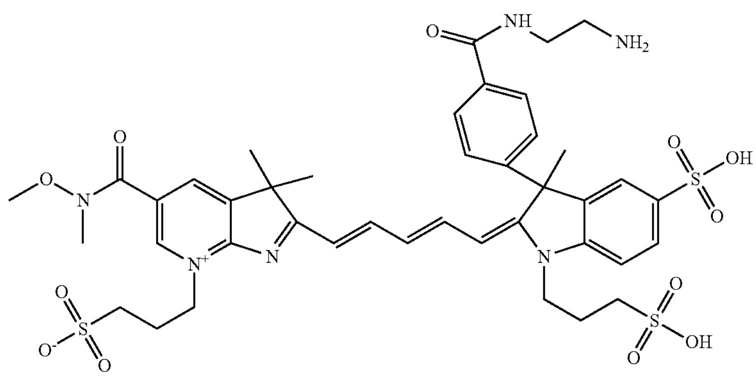 [SMILES: CON(C)C(=O)c1cc2c([n+](CCCS(=O)(=O)[O-])c1)N=C(/C=C/C=C/C=C1/N(CCCS(=O)(=O)O)c3ccc(S(=O)(=O)O)cc3C1(C)c1ccc(C(=O)NCCN)cc1)C2(C)C] |
| 63 | 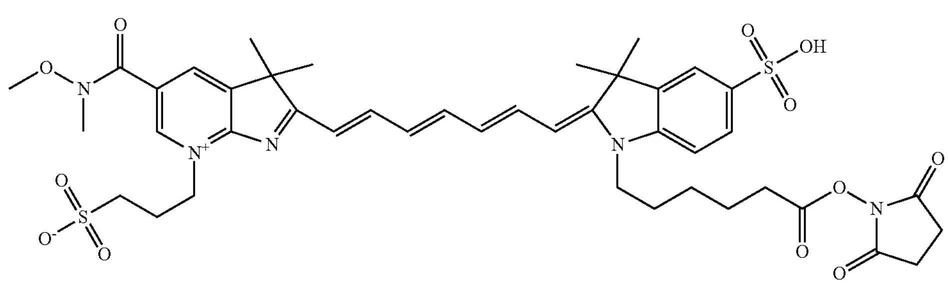 [SMILES: CON(C)C(=O)c1cc2c([n+](CCCS(=O)(=O)[O-])c1)N=C(/C=C/C=C/C=C/C=C1/N(CCCCCC(=O)ON3C(=O)CCC3=O)c3ccc(S(=O)(=O)O)cc3C1(C)C)C2(C)C] |
| 64 | 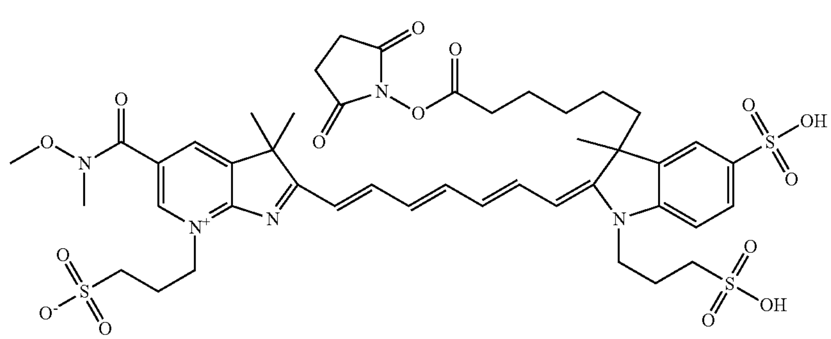 [SMILES: CON(C)C(=O)c1cc2c([n+](CCCS(=O)(=O)[O-])c1)N=C(/C=C/C=C/C=C/C=C1/N(CCCS(=O)(=O)O)c3ccc(S(=O)(=O)O)cc3C1(C)CCCCCC(=O)ON1C(=O)CCC1=O)C2(C)C] |

TABLE 1-continued
Exemplary Reactive Cyanine Dyes
| Dye | Structure |
|---|---|
| 65 | 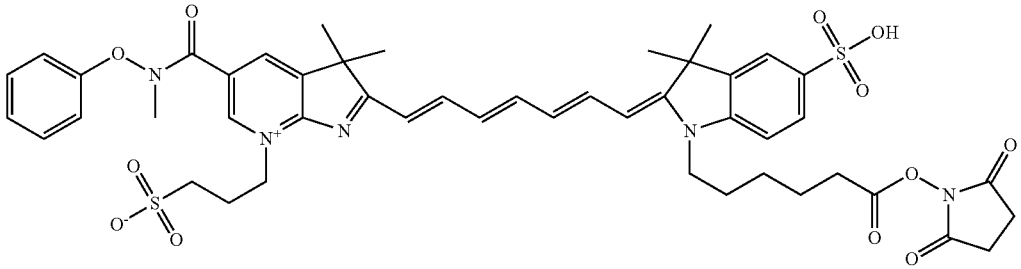 [SMILES: CN(Oc1ccccc1)C(=O)c1cc2c([n+](CCCS(=O)(=O)[O-])c1)N=C(/C=C/C=C/C=C/C=C1/N(CCCCCC(=O)ON3C(=O)CCC3=O)c3ccc(S(=O)(=O)O)cc3C1(C)C)C2(C)C] |
| 66 | 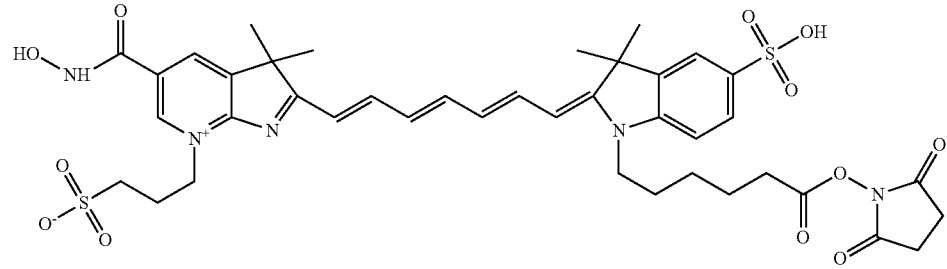 [SMILES: CC1(C)C(/C=C/C=C/C=C/C=C2/N(CCCCCC(=O)ON3C(=O)CCC3=O)c3ccc(S(=O)(=O)O)cc3C2(C)C)=Nc2c1cc(C(=O)NO)c[n+]2CCCS(=O)(=O)[O-]] |
| 67 | 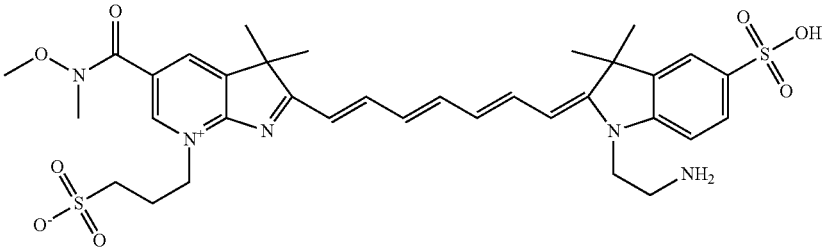 [SMILES: CON(C)C(=O)c1cc2c([n+](CCCS(=O)(=O)[O-])c1)N=C(/C=C/C=C/C=C/C=C1/N(CCN)c3ccc(S(=O)(=O)O)cc3C1(C)C)C2(C)C] |
| 68 | 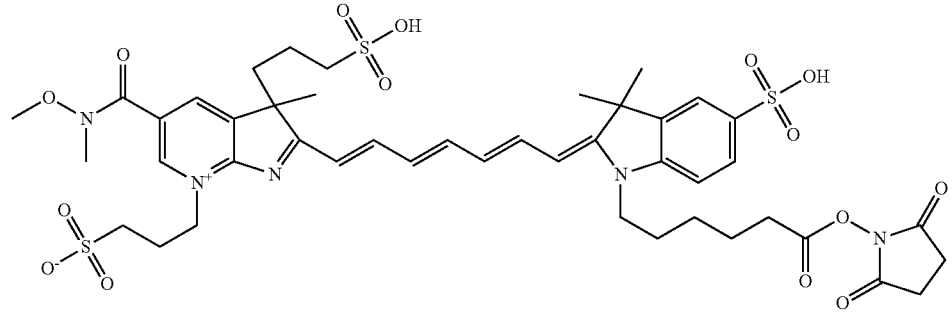 [SMILES: CON(C)C(=O)c1cc2c([n+](CCCS(=O)(=O)[O-])c1)N=C(/C=C/C=C/C=C/C=C1/N(CCCCCC(=O)ON3C(=O)CCC3=O)c3ccc(S(=O)(=O)O)cc3C1(C)C)C2(C)CCCS(=O)(=O)O] |
| 69 | 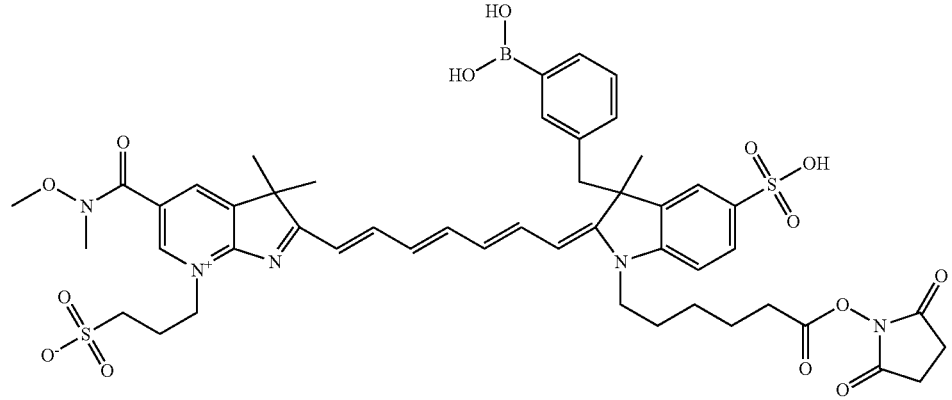 [SMILES: CON(C)C(=O)c1cc2c([n+](CCCS(=O)(=O)[O-])c1)N=C(/C=C/C=C/C=C/C=C1/N(CCCCCC(=O)ON3C(=O)CCC3=O)c3ccc(S(=O)(=O)O)cc3C1(C)Cc1cccc(B(O)O)c1)C2(C)C] |

TABLE 1-continued
Exemplary Reactive Cyanine Dyes
| Dye | Structure |
|---|---|
| 70 | 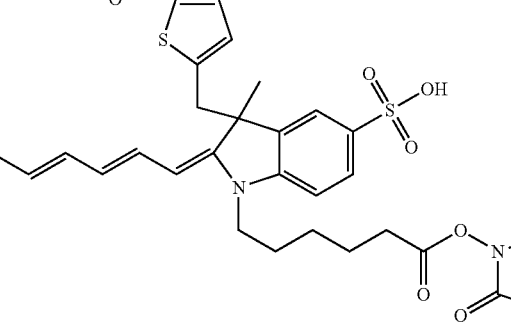 |
| 71 | 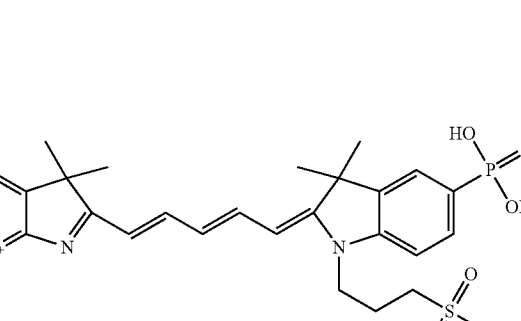 |
| 72 | 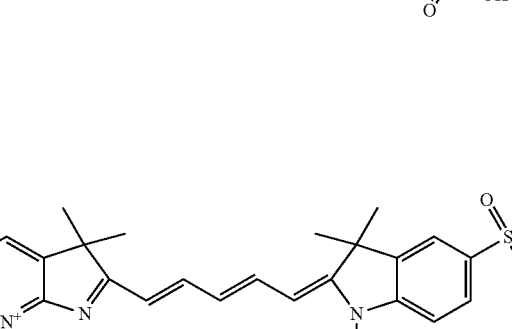 |
| 73 | 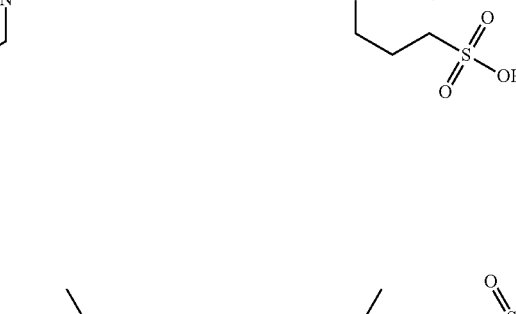 |

TABLE 1-continued

Exemplary Reactive Cyanine Dyes

| Dye | Structure |
|---|---|
| 74 | 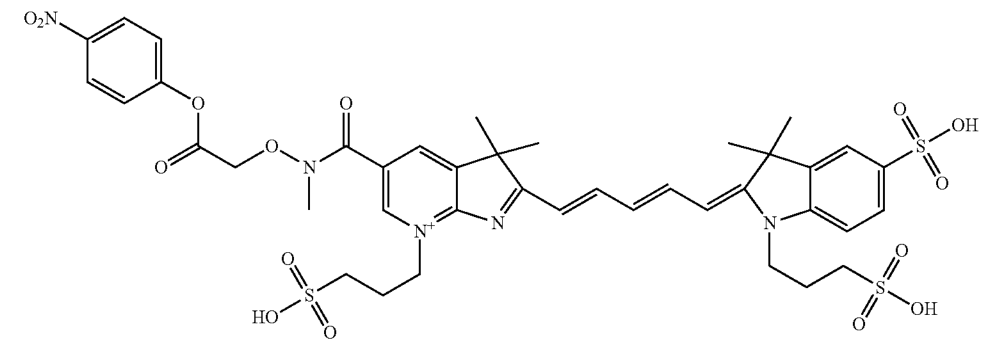 [SMILES: CN(OCC(=O)Oc1ccc([N+](=O)[O-])cc1)C(=O)c1cc2c([n+](CCCS(=O)(=O)O)c1)N=C(/C=C/C=C/C=C1/N(CCCS(=O)(=O)O)c3ccc(S(=O)(=O)O)cc3C1(C)C)C2(C)C] |
| 75 | 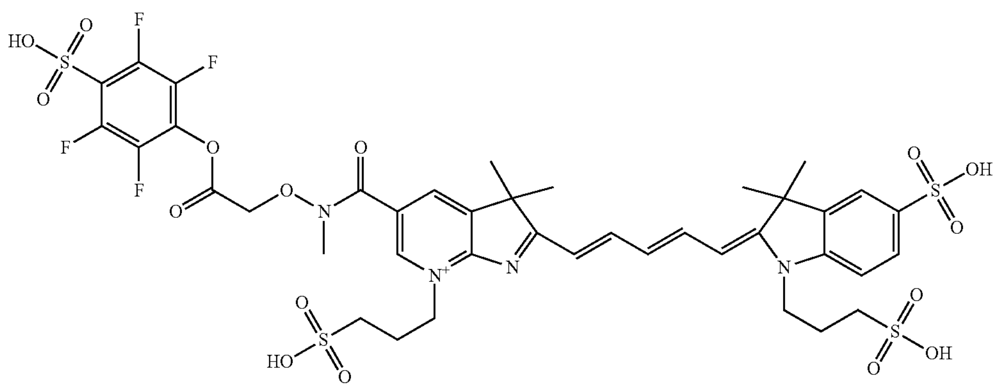 [SMILES: CN(OCC(=O)Oc1c(F)c(F)c(S(=O)(=O)O)c(F)c1F)C(=O)c1cc2c([n+](CCCS(=O)(=O)O)c1)N=C(/C=C/C=C/C=C1/N(CCCS(=O)(=O)O)c3ccc(S(=O)(=O)O)cc3C1(C)C)C2(C)C] |
| 76 | 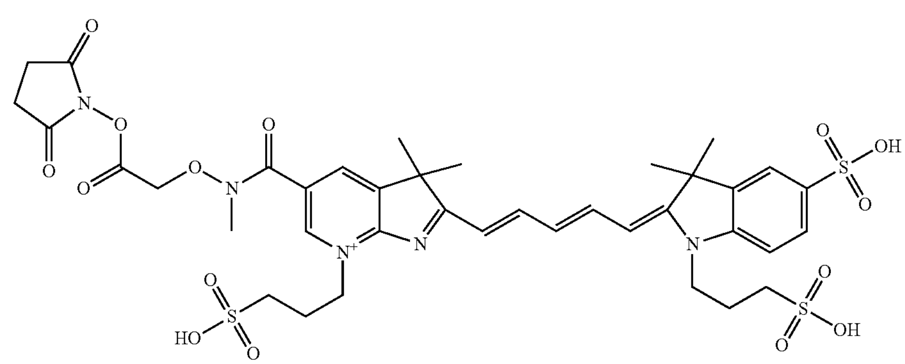 |
| 77 | 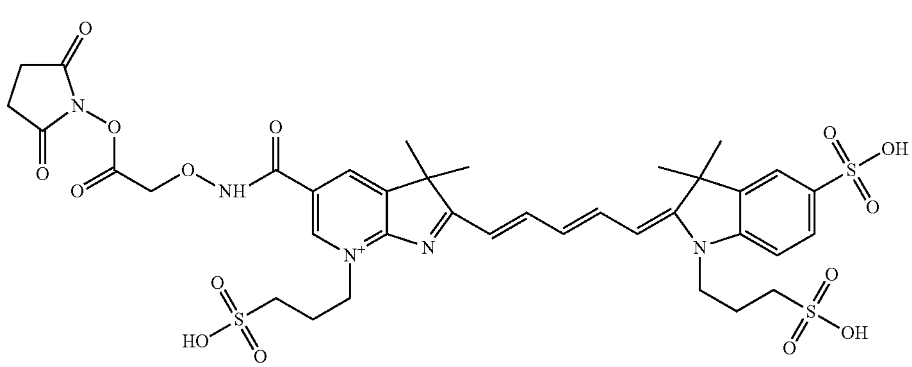 [SMILES: CC1(C)C(/C=C/C=C/C=C2/N(CCCS(=O)(=O)O)c3ccc(S(=O)(=O)O)cc3C2(C)C)=Nc2c1cc(C(=O)NOCC(=O)ON1C(=O)CCC1=O)c[n+]2CCCS(=O)(=O)O] |

TABLE 1-continued
Exemplary Reactive Cyanine Dyes
| Dye | Structure |
|---|---|
| 78 | 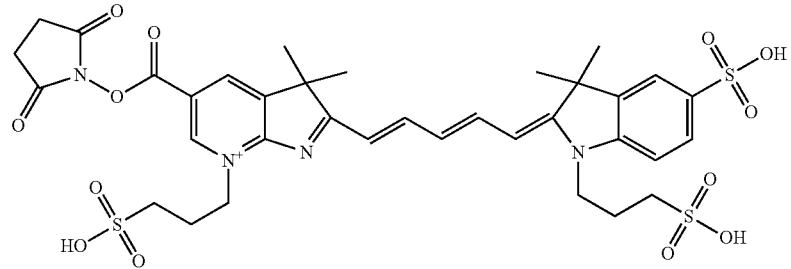 [SMILES: CC1(C)C(/C=C/C=C/C=C2/N(CCCS(=O)(=O)O)c3ccc(S(=O)(=O)O)cc3C2(C)C)=Nc2c1cc(C(=O)ON1C(=O)CCC1=O)c[n+]2CCCS(=O)(=O)O] |
| 79 | 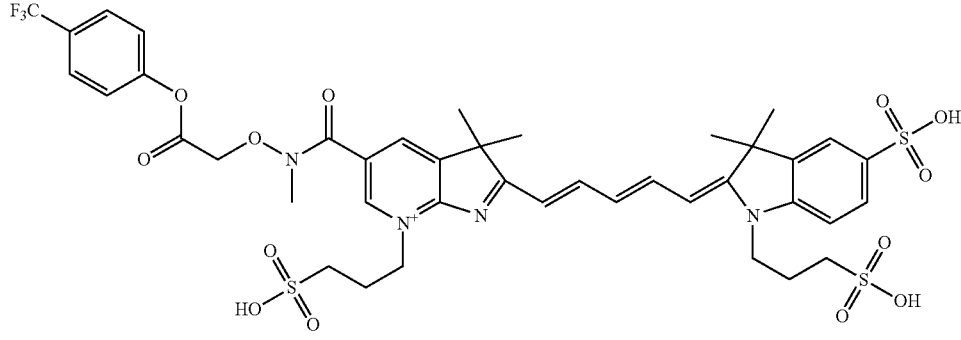 [SMILES: CN(OCC(=O)Oc1ccc(C(F)(F)F)cc1)C(=O)c1cc2c([n+](CCCS(=O)(=O)O)c1)N=C(/C=C/C=C/C=C1/N(CCCS(=O)(=O)O)c3ccc(S(=O)(=O)O)cc3C1(C)C)C2(C)C] |
| 80 | 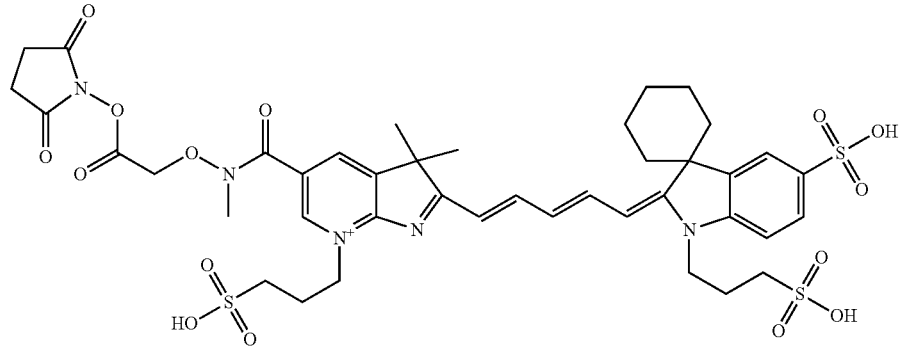 [SMILES: CN(OCC(=O)ON1C(=O)CCC1=O)C(=O)c1cc2c([n+](CCCS(=O)(=O)O)c1)N=C(/C=C/C=C/C=C1/N(CCCS(=O)(=O)O)c3ccc(S(=O)(=O)O)cc3C13CCCCC3)C2(C)C] |
| 81 | 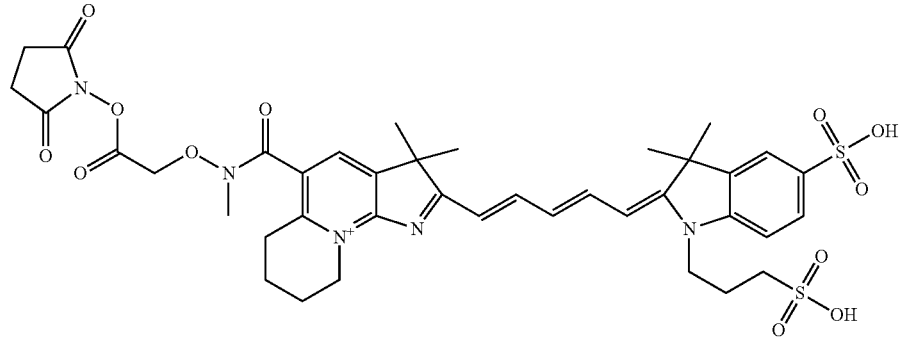 [SMILES: CN(OCC(=O)ON1C(=O)CCC1=O)C(=O)c1cc2c([n+]3c1CCCC3)N=C(/C=C/C=C/C=C1/N(CCCS(=O)(=O)O)c3ccc(S(=O)(=O)O)cc3C1(C)C)C2(C)C] |

TABLE 1-continued

Exemplary Reactive Cyanine Dyes

| Dye | Structure |
|---|---|
| 82 | 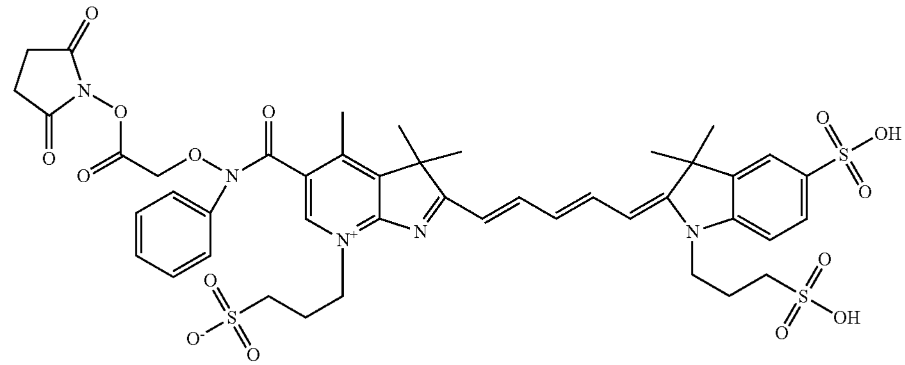 [SMILES: Cc1c(C(=O)N(OCC(=O)ON2C(=O)CCC2=O)c2ccccc2)c[n+](CCCS(=O)(=O)[O-])c2c1C(C)(C)C(/C=C/C=C/C=C1/N(CCCS(=O)(=O)O)c3ccc(S(=O)(=O)O)cc3C1(C)C)=N2] |
| 83 | 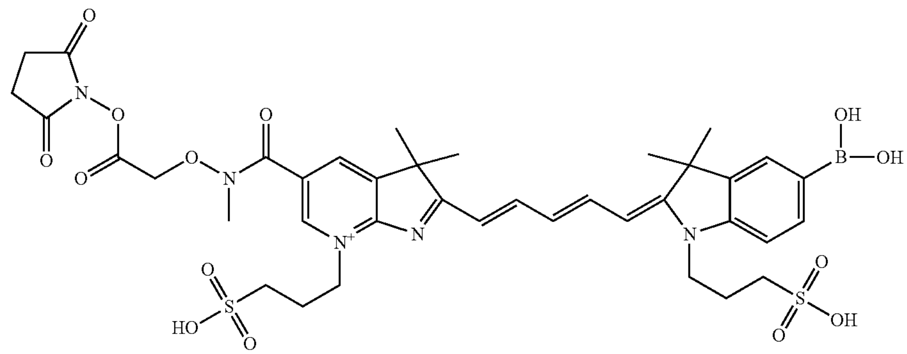 [SMILES: CN(OCC(=O)ON1C(=O)CCC1=O)C(=O)c1cc2c([n+](CCCS(=O)(=O)O)c1)N=C(/C=C/C=C/C=C1/N(CCCS(=O)(=O)O)c3ccc(B(O)O)cc3C1(C)C)C2(C)C] |

Many embodiments of the compounds and conjugates of the invention possess an overall electronic charge. It is to be understood that when such electronic charges are shown to be present, they are balanced by the presence of appropriate counterions, which may or may not be explicitly identified. A biologically compatible counterion, which is preferred for some applications, is not toxic in biological applications, and does not have a substantially deleterious effect on biomolecules. Where the compound of the invention is positively charged, the counterion is typically selected from, but not limited to, chloride, bromide, iodide, sulfate, alkanesulfonate, arylsulfonate, phosphate, perchlorate, tetrafluoroborate, tetraarylboride, nitrate and anions of aromatic or aliphatic carboxylic acids. Where the compound of the invention is negatively charged, the counterion is typically selected from, but not limited to, alkali metal ions, alkaline earth metal ions, transition metal ions, ammonium or substituted ammonium or pyridinium ions. Preferably, any necessary counterion is biologically compatible, is not toxic as used, and does not have a substantially deleterious effect on biomolecules. Counterions are readily changed by methods well known in the art, such as ion-exchange chromatography, or selective precipitation.

It is to be understood that the dyes of the invention have been drawn in one or another particular electronic resonance structure. Every aspect of the instant invention applies equally to dyes that are formally drawn with other permitted resonance structures, as the electronic charge on the subject dyes is delocalized throughout the dye itself.

Synthesis of Reactive Dyes

Many general references providing commonly known chemical synthetic schemes and conditions useful for synthesizing the disclosed dye compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978). General references providing methods for the preparation of nucleoside analogs are available (see, e.g., the review of "Synthetic Procedures in Nucleic Acid Chemistry" Eds. Zorbach and Tipson, Wiley, New York, 1973, Vol. 1 and 2).

Dye compounds as described herein can be purified by any purification protocol known in the art, including chromatography, such as HPLC, preparative thin layer chromatography, flash column chromatography and ion exchange chromatography. Any suitable stationary phase can be used, including normal and reversed phases as well as ionic resins. In certain embodiments, the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject dye compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, 4$^{th}$ edition, Vol. 15/1, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art.

The subject dye compounds can be synthesized via a variety of different synthetic routes using commercially available starting materials and/or starting materials prepared by any convenient synthetic methods. Examples of methods that can be adapted to synthesize the compounds disclosed herein are described below. Those of skill in the art will also be able to readily adapt these methods for the synthesis of any of the specific compounds as described herein.

Any convenient methods of organic and heterocyclic chemistry may be utilized in preparation of the subject dye compounds. Synthesis of the subject dye compounds may be achieved via initial preparation of certain intermediates. Some intermediates of interest have the following general structures (for simplicity, all but a few of the possible substituents of such structures are shown as hydrogen):

Scheme 1. Intermediate structures of reactive dye compounds showing RGM positions of interest

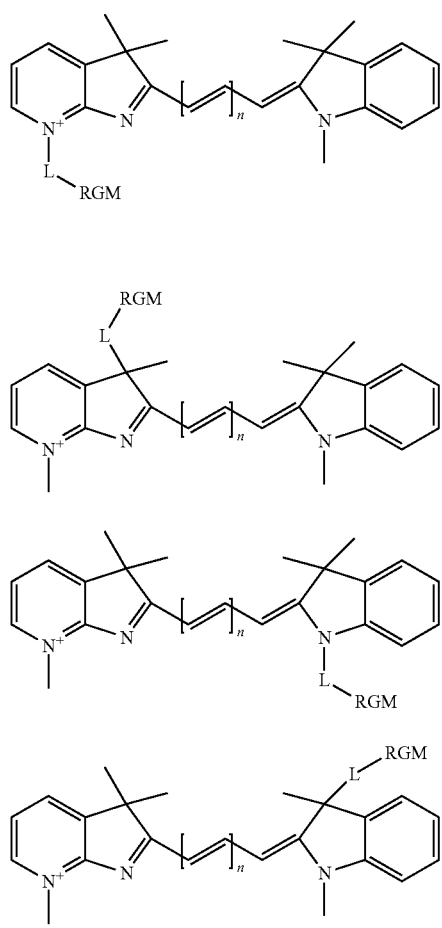

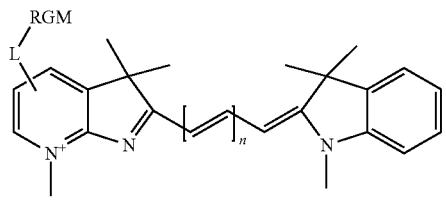

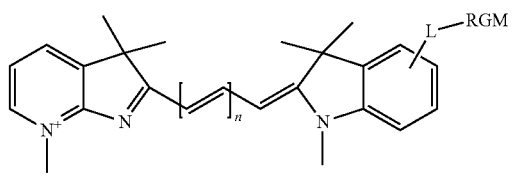

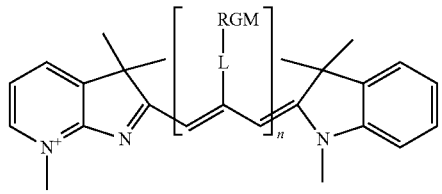

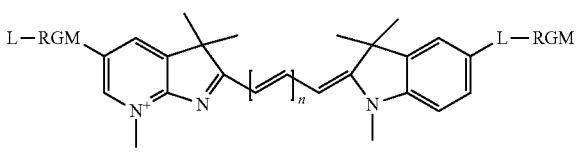

Figure 5:
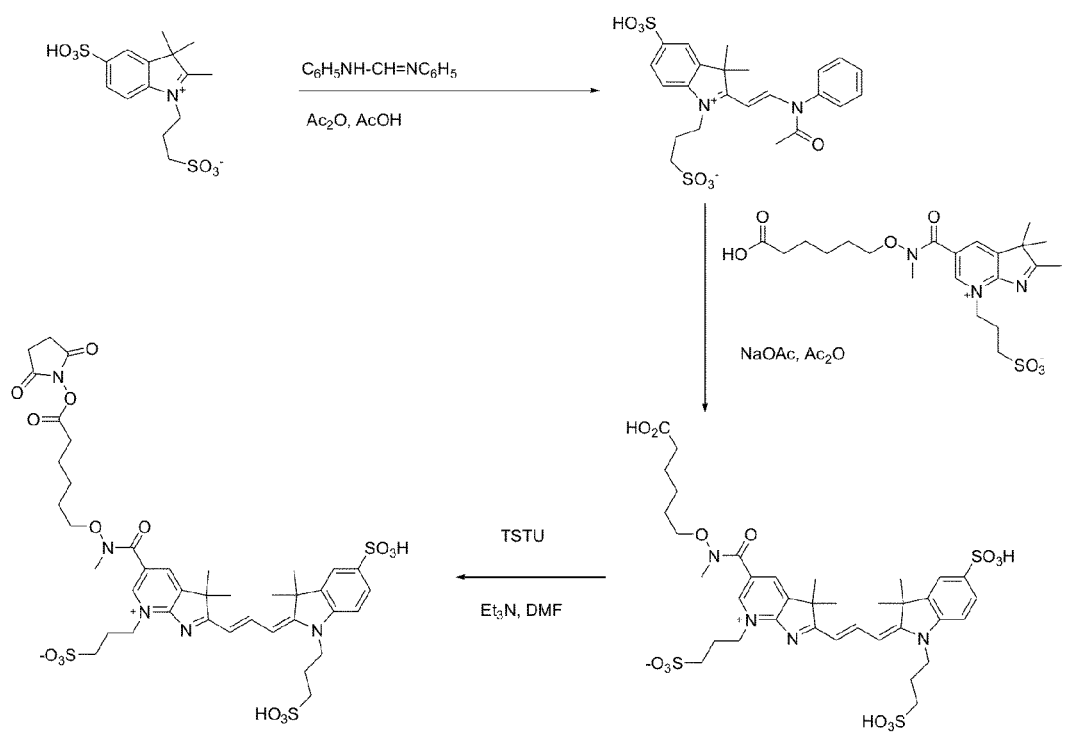
FIG. 5 shows a synthesis scheme of a hydroxamate substituted azaindoline-cyanine dye that includes a linker reactive group moiety (L-RGM) attached to the hydroxamate.
Figure 6:
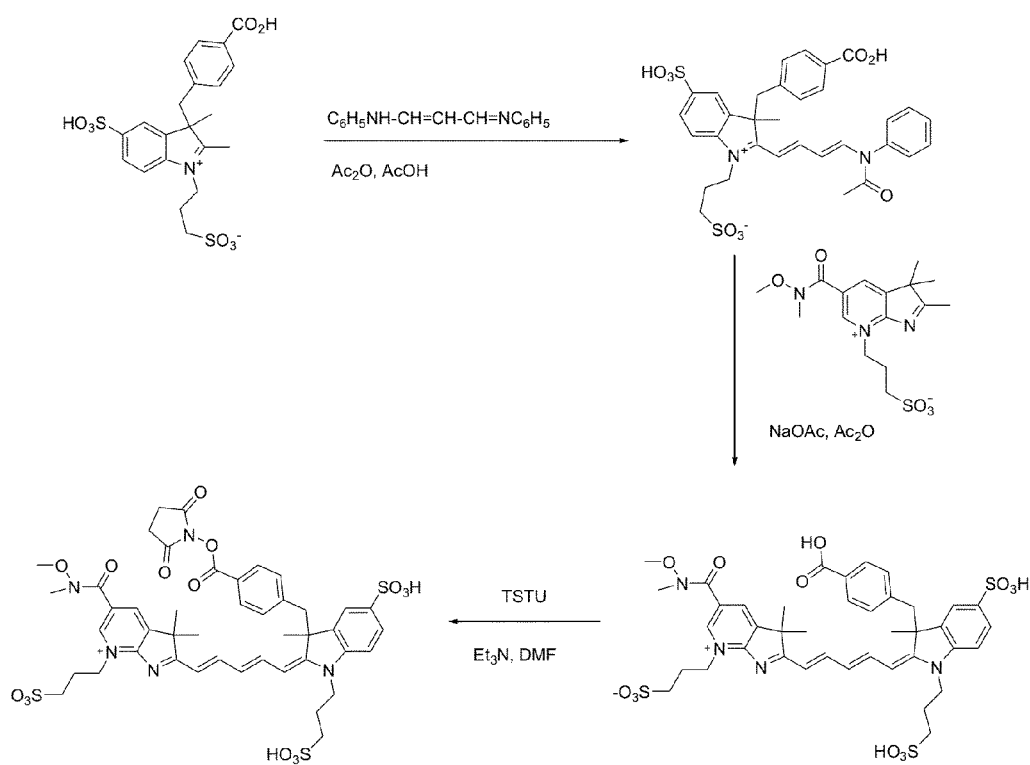
FIG. 6 shows a synthesis of a hydroxamate substituted azaindoline-cyanine that includes a L-RGM substituted indoline ring.
Figure 7:
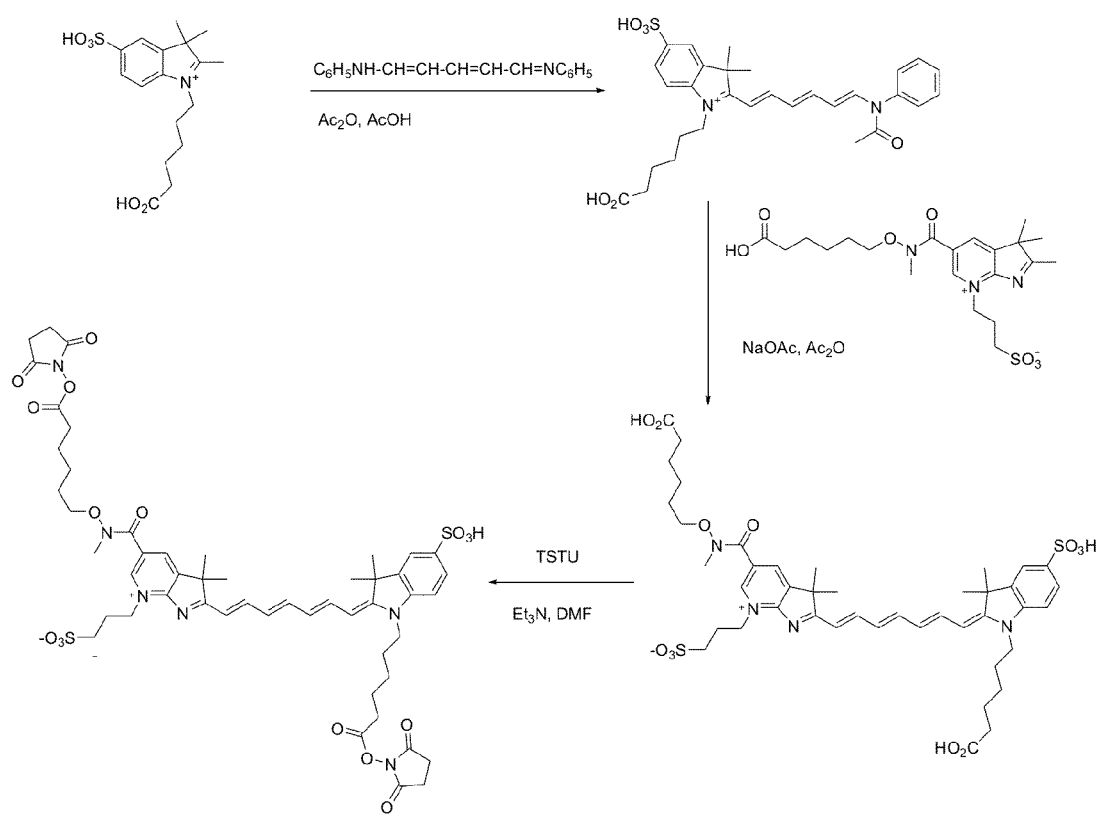
FIG. 7 shows a synthesis of a hydroxamate substituted azaindoline-cyanine that includes two L-RGM groups located respectively at the hydroxamate and an indoline moiety.

These structures may be optionally further substituted, during or after synthesis, to give the corresponding dye substituents as defined above. For carbocyanines, the indoline intermediates may be readily synthesized by a reaction that is analogous to a Fischer indole synthesis (see Sundberg R J. THE CHEMISTRY OF INDOLES, Organic chemistry, a series of monographs, 1970, Academic Press) as shown in Scheme 2. In some cases, the synthesis of different substituted carbocyanines is achieved using schemes as illustrated in FIGS. 5-7.

Scheme 2. Synthesis of azaindoline intemedates

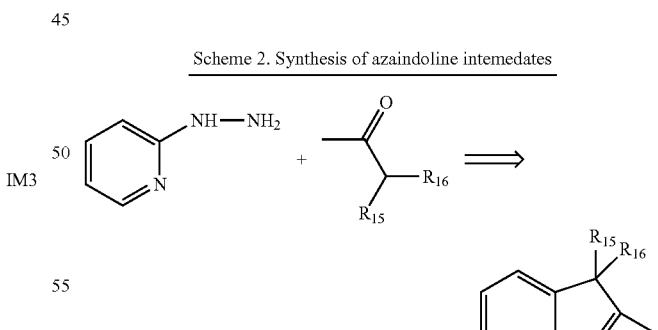

Synthesis of the cyanine dyes of the invention, where an RGM group is attached at an azaindoline ring, an indolium ring or the polymethine linker, may be achieved either through the initial preparation of the corresponding indoline intermediate or through the post modification of carbocyanines through the common functional group transformations (Larock, "Comprehensive Organic Transformations", 1999, John Wiley & Sons). Indolines can be readily converted to desired carbocyanines following any convenient methods. For example, N,N'-diphenylformamidine, triethylorthoformate, malonaldehyde bis(phenylimine) hydrochloride, 1,1,3-trimethoxypropane, 1,1,3,3-tetramethoxypropane and glutaconaldehyde dianil monochloride are convenient intermediates used in the synthesis of carbocyanines. Exemplary carbocyanines that have conjugated double bonds are described in U.S. Pat. No. 5,831,098 to Ollmann, Jr (1998); U.S. Pat. No. 6,086,737 to Patonay, et al. (2000); U.S. Pat. No. 6,048,982 to Waggoner (2000); and U.S. Pat. No. 5,453,505 to Lee, et al. (1995); U.S. Pat. No. 5,639,874 to Middendorf, et al. (1997); U.S. Pat. No. 3,864,644 to Lincoln, et al. (1975); U.S. Pat. No. 4,011,086 to Simson (1977).

For the synthesis of carbocyanines, a substituted aryl hydrazine (for simplicity, all but a few of the possible substituents are shown as hydrogen), which may be a substituted pyridinehydrazine, is reacted with a substituted methyl ketone to yield a 3,3-disubstituted 2-methylindole derivative (see Scheme 2). It is possible to utilize a sulfonated pyridinehydrazine derivative or a sulfonated quinolinehydrazine derivative to increase the solubility of the final dye. The 3,3-disubstituted-2-methylazaindoline is then quaternized on the nitrogen atom to an pyridium derivative with an alkylating agent that may be an alkyl halide such as ethyl iodide, an alkylsulfonate such as methyl p-toluenesulfonate or a cyclic sulfonate such as propanesultone or butanesultone. In some cases, the key azaindoline or benzoazaindoline intermediates are sulfonated one or more times before or after quaternization and subsequent condensation with the indolium moiety and polymethine moiety to form the subject dyes. Variations on these methods may be used that yield substituents on the polymethine bridge or on the indolium or azaindoline portion of the dye precursor. See, e.g., Leung W, et al., WO 02/26891; Brooker, et al., J. AM. CHEM. SOC., 64, 199 (1942); Chu-Moyer, et al. J. ORG. CHEM., 60, 5721 (1995); Turner, J. ORG. CHEM., 48, 3401 (1983); Couture, et al. J. HETEROCYCLIC CHEM., 24, 1765 (1987); Petric, et al. J. HETEROCYCLIC CHEM., 14, 1045, (1977); Barlin, et al. AUST. J. CHEM., 37, 1729 (1984); Saikachi et al. CHEM. & PHARM. BULL., 9, 941 (1961); Barlin, AUST. J. CHEM., 36, 983 (1983); Foye, et al., J. PHARM. SCI., 64, 1371 (1975); Khanna, et al. J. ORG. CHEM., 60, 960 (1995)); British Patent No. 870,753 to Ficken, et al. (1961).

In some cases, the synthesis of the subject dyes involves three precursors: the appropriate benzazolium or azabenzazolium salt and a source for the polymethine spacer. Typically each component is selected so as to incorporate the desired chemical substituents, or functional groups (e.g. RGM) that can be converted to the appropriate substituents. A variety of chemistries and materials may be used to prepare and combine these precursors so as to yield any of the subject dye compounds.

It is recognized that there are many possible variations that may yield equivalent results. The substituents on the aromatic carbons of the azabenzazolium moiety may be incorporated in the parent aza- or polyazabenzazole molecule prior to quaternization with an alkylating agent. However, such substituents may also be incorporated during the synthesis of the azabenzazole moiety. Alkyl, alkoxy, carboxyl, and halogen substituents at aromatic carbons may already be present as substituents on the benzazole or azabenzazole precursors, or on compounds that are readily converted to such precursors using any convenient methods. Sulfonic acid groups may be introduced on the precursors prior to condensation of the cyanine dye [see, e.g., U.S. Pat. No. 5,767,287 to Bobrow, et al. (1998)]. Aminoalkyl groups may contain a protecting group when they are first introduced, e.g., by substitution onto the benzazole or azabenzazole precursor. The protecting group may then be removed after condensation of the cyanine dye. Aromatic amino groups may be prepared via the reduction of a nitro substituted benzazolium precursor, which in turn is prepared by the nitration of the benzazole precursor.

Any convenient methods may be used for synthesis of dyes that contain a variety of reactive groups such as those described in Table 3. In some cases, amine-reactive dyes such as "activated esters" of carboxylic acids, may be synthesized by coupling a carboxylic acid to a relatively acidic "leaving group". Other amine-reactive groups of interest include, but are not limited to, sulfonyl halides, which may be prepared from sulfonic acids using a halogenating agent such as $PCl_5$ or $POCl_3$; halotriazines, which may be prepared by the reaction of cyanuric halides with amines; and isocyanates or isothiocyanates, which may be prepared from amines and phosgene or thiophosgene, respectively.

Dyes containing amines and hydrazides are useful for conjugation to carboxylic acids, aldehydes and ketones. In some case, these are synthesized by reaction of an activated ester of a carboxylic acid or a sulfonyl halide with a diamine, such as cadaverine, or with a hydrazine. Alternatively, aromatic amines may be synthesized by chemical reduction of a nitroaromatic compound. Amines and hydrazines are useful precursors for synthesis of thiol-reactive haloacetamides or maleimides by any convenient methods.

Nucleosides and nucleotides labeled with dyes of the invention are useful for some applications of nucleic acid labeling. In some cases, carbocyanine-amidites are used for labeling nucleotides and nucleosides using methods similar to those described by U.S. Pat. No. 5,986,086 to Brush, et al. (1999); U.S. Pat. No. 5,808,044 to Brush, et al. (1998); and U.S. Pat. No. 5,556,959 to Brush, et al. (1996).

Dye Conjugates

The present disclosure provides conjugates. By "conjugate" is meant a first moiety that is stably associated with a second moiety. By "stably associated" is meant that a moiety is bound to another moiety or structure under standard conditions. In certain embodiments, the first and second moieties are bound to each other through one or more covalent bonds. In some cases, the dyes of the invention are coupled to a substrate through one or more chemically reactive groups (RGM) to produce a dye conjugate. The reactive dyes of the invention can react with a wide variety of substrates that contain or are modified to contain functional groups with suitable reactivity, resulting in conjugation of the dye to the substance.

Any convenient substance (e.g., organic or inorganic substances) may be utilized as a substrate in the subject dye conjugates. In some cases, the substrate is a biopolymer. Substrates of interest include an amino acid, a peptide, a protein, a tyramine, a polysaccharide, an ion-complexing moiety, a nucleoside, a nucleotide, an oligonucleotide, a nucleic acid, an antibody or antibody fragment or derivative, a hapten, a psoralen, a drug, a hormone, a lipid, a lipid assembly, a polymer, a polymeric microparticle, a biological cell or virus, as described in further detail below. Useful dye-conjugates also include, but are not limited to, conjugates where the substrate is an amino acid, a nucleotide, a biopolymer (e.g., amino acid polymer, nucleic acid polymer, polysaccharide, carbohydrate, or lipid), an antigen, steroid, vitamin, drug, hapten, metabolite, toxin, environmental pollutant, ion-complexing moiety, or a glass, plastic, or other non-biological polymer. In some embodiments, the substrate is a cell, cellular system, cellular fragment or component, or subcellular particle (e.g., a virus particle, bacterial particle, or a component thereof), a virus particle, a bacterial particle, a virus component, a biological cell (such as animal cell, plant cell, bacteria, yeast, or protist), or a cellular component. Reactive dyes may also be used to label functional groups at the cell surface, in cell membranes, organelles, or cytoplasm.

In certain instances, the conjugates are conjugates of R-phycoerythrin and of allophycocyanin with selected dyes of the invention that serve as excited-state energy acceptors or donors. In these conjugates, excited state energy transfer results in long wavelength fluorescence emission when excited at relatively short wavelengths.

In some embodiments, the dye conjugate is a hydroxamate substituted azaindoline-cyanine dye conjugate, where the conjugate includes a 5-hydroxamate-azaindoline group linked to a 5-membered heterocylic ring via a divalent polymethine linking group, wherein one or more of the 5-hydroxamate-azaindoline group, the divalent polymethine linking group and the 5-membered heterocylic ring is conjugated to a substrate.

In some instances, the dye conjugate includes a dye (e.g., as described above), of one of formulae I to VI, where the RGM is conjugated to a substrate of interest to produce the conjugate. In certain embodiments, the dye bioconjugate is prepared by coupling a dye compound of one of Formulae of I, II, III, IV, V or VI with an antibody.

In some cases, the dye conjugate is described by Formula VII:

In some embodiments, in Formula VII, n is 0. In some embodiments, in Formula VII, n is 1. In some embodiments, in Formula VII, n is 2. In some embodiments, in Formula VII, n is 3.

In some cases, in Formula VII, $R_1$-$R_3$ are independently a hydrogen, a halogen, an alkyl having 1-20 carbons, a cycloalkyl having 3-20 carbons, an aryl, a heteroaryl, an amino, an alkylamino, an arylamino, a thiol, an alkylthiol, an arylthiol, a heteroarylthiol, a polyethyleneglycol, an alkoxy, an aryloxy, a carboxyalkyl, or a L-SUBSTRATE. In certain cases, $R_1$-$R_3$ are each hydrogen. In certain cases, in Formula VII, two of $R_1$-$R_3$ are cyclically linked to form a six-membered carbocycle or heterocycle ring. In certain embodiments, in Formula VII, one of $R_1$-$R_3$ is an alkoxy, an aryloxy, or a L-SUBSTRATE.

In some cases, in Formula VII, $R_4$ and $R_5$ are independently an alkyl having 1-20 carbons, a cycloalkyl having 3-20 carbons, an arylalkyl, a heteroarylalkyl, a carboxyalkyl, a sulfoalkyl, or a L-SUBSTRATE.

In some cases, in Formula VII, $R_4$ and $R_5$ are each independently selected from an alkyl having 1-20 carbons, where the alkyl may be substituted with one or more substituents selected from a SUBSTRATE, a sulfonate, a phosphate, amino, a substituted amino, an ammonium, a carboxy, and a hydroxyl. In certain embodiments, $R_4$ and $R_5$ are each inde-

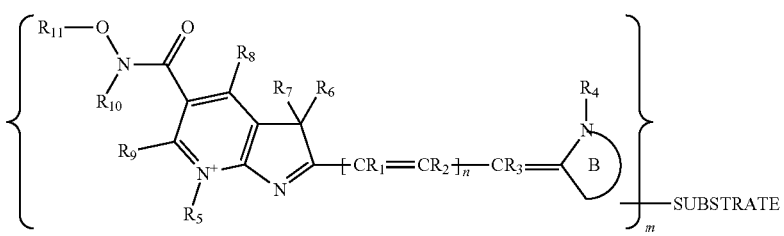

Formula VII where B, n and $R_1$-$R_{11}$ are as described above for Formula I except that RGM is substrate, and m is 1 to 50.

In certain instances, in Formula VII, Ring B represents the atoms necessary to form a nitrogen-containing five-membered heterocyclic ring and further includes zero to three fused aromatic rings; where each atom of the five-membered heterocyclic ring and the zero to three fused aromatic ring is independently selected from the group consisting of C, CH, C(alkyl), C(aryl), O, S, N, N(aryl), N(acyl) and N(alkyl), and the five-membered heterocyclic ring and the zero to three aromatic rings are optionally substituted with one or more substituents independently selected from the group consisting of a hydrogen, an alkyl having 1-20 carbons, a hydroxy, an alkoxy having 1-20 carbons, a trifluoromethyl, a halogen, a methylthio, a sulfonate, a carbonyl, an amino, a thiol, a phosphonate, and a L-SUBSTRATE.

In certain embodiments, in formula VII, m is 1 to 50, such as 3 to 35, 6 to 35, 10 to 35 or 15 to 20. In some instances, 1 to about 50 dye molecules are conjugated to the SUBSTRATE, such as about 3 to about 35 dye molecules, about 6 to about 35 dye molecules, about 10 to about 35 dye molecules, or about 15 to about 20 dye molecules per SUBSTRATE. In some embodiments, as many as about 35 dye molecules can be conjugated to the SUBSTRATE without significant self-quenching. In certain instances, m is 1, 2, 3, 4, 5, 6, 7, 8, 9, 10, 11, 12, 13, 14, 15, 20, 25, 30, 35, 40, 45 or 50. In certain instances, m is about 5, about 10, about 15, about 20, about 25, about 30, about 35, about 40, about 45 or about 50.

pendently selected from —$(CH_2)_m$—Z, where m is 1-12 and Z is selected from —H, —$CO_2H$, —$NH_2$, —$SO_3^-$, —$PO_3H$ and SUBSTRATE.

In certain instances, in Formula VII, $R_6$ and $R_7$ are independently an alkyl having 1-20 carbons, a cycloalkyl having 3-20 carbons, an aryl, an arylalkyl, a heteroaryl, a heteroarylalkyl, a carboxyalkyl, a carboxyaryl, a sulfoalkyl, or a L-SUBSTRATE. In certain instances, in Formula VII, $R_6$ and $R_7$ are each independently an alkyl having 1-20 carbons. In certain instances, in Formula VII, $R_6$ and $R_7$ are each independently a lower alkyl. In certain instances, in Formula VII, $R_6$ and $R_7$ are each methyl. In some embodiments, $R_6$ is a lower alkyl (e.g., a methyl or an ethyl) and $R_7$ is L-SUBSTRATE. In some embodiments, $R_7$ is L-Z (e.g., —$(CH_2)_m$—Z, where m is 1-12 and Z is selected from —H, —$CO_2H$, —$NH_2$, —$SO_3^-$, —$PO_3H$ and SUBSTRATE).

In some instances, in Formula VII, $R_8$ and $R_9$ are independently a hydrogen, an alkyl having 1-20 carbons, a hydroxy, an alkoxy having 1-20 carbons, a trifluoromethyl, a halogen, a methylthio, a sulfonate, a carbonyl, a hydroxy, an amino, a thiol, a phosphonyl, or a L-SUBSTRATE. In some instances, in Formula VII, $R_8$ and $R_9$ are each independently a hydrogen or an alkyl having 1-20 carbons. In some instances, in Formula VII, $R_8$ and $R_9$ are each independently a hydrogen or L-SUBSTRATE. In some instances, in Formula VII, $R_8$ and $R_9$ are each hydrogen. In certain embodiments, $R_9$ is cyclically linked to the adjacent N of the azaindoline ring, e.g., to form a 6 membered ring.

In some embodiments, in Formula VII, $R_{10}$ and $R_{11}$ are each independently, a hydrogen, an alkyl, an aryl, an arylalkyl, a heteroaryl, a heteroarylalkyl, a carboxyalkyl, a sulfoalkyl, or a L-SUBSTRATE. In certain embodiments, in Formula VII, $R_{10}$ and $R_{11}$ are each independently hydrogen, an alkyl, an aryl or L-SUBSTRATE. In some instances, in Formula VII, $R_{10}$ and $R_{11}$ are each independently an alkyl, such as a lower alkyl (e.g., methyl, ethyl, propyl, isopropyl, etc.). In certain instances, in Formula VII, $R_{10}$ is L-SUBSTRATE. In certain cases, in Formula VII, $R_{11}$ is L-SUBSTRATE.

In some cases, L is none, an alkyl, or a polyethyleneglycol. In certain instances, SUBSTRATE is a biological molecule, either a small bioactive ligand, or a biopolymer.

In certain embodiments, in Formula VII, at one or more of $R_1$-$R_{11}$ includes a L-SUBSTRATE.

In certain embodiments, in Formula VII, at two of $R_1$-$R_{11}$ includes a L-SUBSTRATE. In certain instances, in Formula VII, B includes a L-SUBSTRATE.

In some embodiments, the dye conjugate is described by Formula VIII:

1-20 carbons, a carboxyalkyl, a sulfoalkyl, or a L-SUBSTRATE; $R_6$, $R_7$, $R_{15}$ and $R_{16}$ are each independently an alkyl having 1-20 carbons, a cycloalkyl having 3-20 carbons, a carboxyalkyl, a carboxyaryl, a sulfoalkyl, a sulfoalkyl, or a L-SUBSTRATE; $R_8$, $R_9$ and $R_{17}$-$R_{20}$ are each independently a hydrogen, a halogen, sulfonate, or a L-SUBSTRATE; and $R_{10}$ and $R_{11}$ are each independently an alkyl, or a L-SUBSTRATE.

In some cases, in Formula VIII, $R_1$-$R_3$ are each a hydrogen; $R_4$ and $R_5$ are each independently an alkyl having 1-20 carbons, a carboxyalkyl, a sulfoalkyl, or a L-SUBSTRATE; $R_6$, $R_7$, $R_{15}$ and $R_{16}$ are each independently an alkyl having 1-20 carbons, a cycloalkyl having 3-20 carbons, an aryl, an arylalkyl, a carboxyalkyl, a carboxyaryl, a sulfoalkyl, or a L-SUBSTRATE; $R_8$, $R_9$, $R_{17}$, $R_{19}$ and $R_{20}$ are each hydrogen; $R_{18}$ is sulfonate; and $R_{10}$ and $R_{11}$ are each independently an alkyl, or a L-SUBSTRATE.

In certain cases, in Formula VIII, L is none, an alkyl, an alkoxy, a thioalkyl, an amino acid, a sulfo amino acid, polyamine, a polyethyleneglycol, an aryl, an arylalkyl, a heteroaryl alkyl, or a heteroaryl. In some embodiments, in formula VIII, L is none, an alkyl, or a polyethyleneglycol.

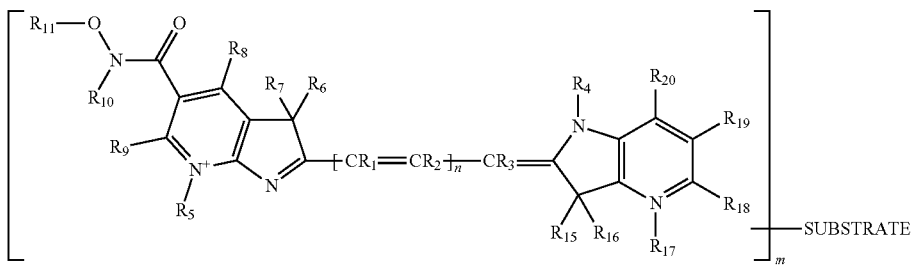

Formula VIII where n and $R_1$-$R_{11}$ and $R_{15}$-$R_{20}$ are as described above for Formula II except that RGM is substrate, and m is 1 to 50.

In certain embodiments, in formula VIII, m is 1 to 50, such as 3 to 35, 6 to 35, 10 to 35 or 15 to 20. In some instances, 1 to about 50 dye molecules are conjugated to the SUBSTRATE, such as about 3 to about 35 dye molecules, about 6 to about 35 dye molecules, about 10 to about 35 dye molecules, or about 15 to about 20 dye molecules per SUBSTRATE. In some embodiments, as many as about 35 dye molecules can be conjugated to the SUBSTRATE without significant self-quenching. In certain instances, m is 1, 2, 3, 4, 5, 6, 7, 8, 9, 10, 11, 12, 13, 14, 15, 20, 25, 30, 35, 40, 45 or 50. In certain instances, m is about 5, about 10, about 15, about 20, about 25, about 30, about 35, about 40, about 45 or about 50.

In some instances, in Formula VIII, $R_1$-$R_3$ are each independently a hydrogen, an alkyl having 1-20 carbons, a cycloalkyl having 3-20 carbons, an aryl, an alkylamino, an arylamino, a thioalkyl, a thiol aryl, an aryloxy, or a L-SUBSTRATE; $R_4$ and $R_5$ are each independently an alkyl having 1-20 carbons, a carboxyalkyl, a sulfoalkyl, or a L-SUBSTRATE; $R_6$, $R_7$, $R_{15}$ and $R_{16}$ are each independently an alkyl having 1-20 carbons, a cycloalkyl having 3-20 carbons, an aryl, an arylalkyl, a carboxyalkyl, a carboxylaryl, a sulfoalkyl, or a L-SUBSTRATE; $R_8$, $R_9$ and $R_{17}$-$R_{20}$ are each independently a hydrogen, an alkyl having 1-20 carbons, a halogen, sulfonate, or a L-SUBSTRATE; $R_{10}$ and $R_{11}$ are each independently an alkyl, an aryl, an arylalkyl, a carboxyalkyl, a sulfoalkyl, or a L-SUBSTRATE.

In certain instances, in Formula VIII, $R_1$-$R_3$ are each a hydrogen; $R_4$ and $R_5$ are each independently an alkyl having In some embodiments, in Formula VIII, n is 0. In some embodiments, in Formula VIII, n is 1. In some embodiments, in Formula VIII, n is 2. In some embodiments, in Formula VIII, n is 3.

In certain instances, in Formula VIII, $R_1$-$R_3$ are independently a hydrogen, a halogen, an alkyl having 1-20 carbons, a cycloalkyl having 3-20 carbons, an aryl, a heteroaryl, an amino, an alkylamino, an arylamino, a thiol, an alkylhiol, an arylthiol, a heteroarylthiol, a polyethyleneglycol, an alkoxy, an aryloxy, a carboxyalkyl, or a L-SUBSTRATE. In certain cases, $R_1$-$R_3$ are each hydrogen. In certain cases, in Formula VIII, two of $R_1$-$R_3$ are cyclically linked to form a six-membered carbocycle or heterocycle ring. In certain embodiments, in Formula VIII, one of $R_1$-$R_3$ is an alkoxy, an aryloxy, or a L-SUBSTRATE.

In some cases, in Formula VIII, $R_4$ and $R_5$ are independently an alkyl having 1-20 carbons, a cycloalkyl having 3-20 carbons, an arylalkyl, a heteroarylalkyl, a carboxyalkyl, a sulfoalkyl, or a L-SUBSTRATE. In some cases, in Formula VIII, $R_4$ and $R_5$ are each independently selected from an alkyl having 1-20 carbons, where the alkyl may be substituted with one or more substituents selected from a SUBSTRATE, a sulfonate, a phosphate, amino, a substituted amino, an ammonium, a carboxy, and a hydroxyl. In certain embodiments, $R_4$ and $R_5$ are each independently selected from —$(CH_2)_m$—Z, where m is 1-12 and Z is selected from —H, —$CO_2H$, —$NH_2$, —$SO_3^-$, —$PO_3H$ and SUBSTRATE.

In some embodiments, in Formula VIII $R_6$, $R_7$, $R_{15}$ and $R_{16}$ are independently an alkyl having 1-20 carbons, a cycloalkyl having 3-20 carbons, an aryl, an arylalkyl, a heteroaryl, a heteroarylalkyl, a carboxyalkyl, a carboxyaryl, a sulfoalkyl, or a L-SUBSTRATE. In certain instances, in Formula VIII, $R_6$, $R_7$, $R_{15}$ and $R_{16}$ are each independently an alkyl having 1-20 carbons. In certain instances, in Formula VIII, $R_6$, $R_7$, $R_{15}$ and $R_{16}$ are each independently a lower alkyl. In certain instances, in Formula VIII, $R_6$ and $R_7$ are each methyl. In certain instances, in Formula VIII, $R_{15}$ and $R_{16}$ are each methyl. In some embodiments, $R_6$ is a lower alkyl (e.g., a methyl or an ethyl) and $R_7$ is L-SUBSTRATE. In some embodiments, $R_7$ is L-Z (e.g., —$(CH_2)_m$—Z, where m is 1-12 and Z is selected from —H, —$CO_2H$, —$NH_2$, —$SO_3^-$, —$PO_3H$ and SUBSTRATE.) In some embodiments, $R_{15}$ is a lower alkyl (e.g., a methyl or an ethyl) and $R_{16}$ is L-SUBSTRATE. In some embodiments, $R_{16}$ is L-Z (e.g., —$(CH_2)_m$—Z, where m is 1-12 and Z is selected from —H, —$CO_2H$, —$NH_2$, —$SO_3^-$, —$PO_3H$ and SUBSTRATE.)

In some instances, in Formula VIII, $R_8$, $R_9$ and $R_{17}$-$R_{20}$ are each independently a hydrogen, an alkyl having 1-20 carbons, a hydroxy, an alkoxy having 1-20 carbons, a trifluoromethyl, a halogen, a methylthio, a carbonyl, an amino, a thiol, a sulfonate, a phosphonyl, or a L-SUBSTRATE. In some instances, in Formula VIII, $R_8$, $R_9$ and $R_{17}$-$R_{20}$ are each independently a hydrogen or an alkyl having 1-20 carbons. In some instances, in Formula VIII, $R_8$, $R_9$ and $R_{17}$-$R_{20}$ are independently a hydrogen or L-SUBSTRATE. In some instances, in Formula VIII, $R_8$ and $R_9$ are each hydrogen. In some instances, in Formula VIII, $R_{17}$-$R_{20}$ are each hydrogen. In certain embodiments, $R_9$ is cyclically linked to the adjacent N of the azaindoline ring, e.g., to form a 6 membered ring.

In some cases, in Formula VIII, $R_{10}$ and $R_{11}$ are each independently hydrogen, an alkyl, an aryl, an arylalkyl, a heteroaryl, a heteroarylalkyl, a carboxyalkyl, a sulfoalkyl, or a L-SUBSTRATE. In certain embodiments, in Formula VIII, $R_{10}$ and $R_{11}$ are each independently hydrogen, an alkyl, an aryl or L-SUBSTRATE. In some instances, in Formula VIII, $R_{10}$ and $R_{11}$ are each independently an alkyl, such as a lower alkyl (e.g., methyl, ethyl, propyl, isopropyl, etc.). In certain instances, in Formula VIII, $R_{10}$ is L-SUBSTRATE. In certain cases, in Formula VIII, $R_{11}$ is L-SUBSTRATE.

One or more of $R_4$ and $R_5$, $R_6$ and $R_7$, $R_5$ and $R_9$, $R_{15}$ and $R_{16}$, $R_4$ and $R_{20}$, $R_4$ and $R_6/R_7$, or $R_6/R_7$ and $R_{15}/R_{16}$ might be taken in combination to form a 5- to 50-membered ring (e.g., a 5- to 12-membered ring, such as a 5, 6, 7 or 8-membered ring).

In some cases, L is none, an alkyl, or a polyethyleneglycol. In certain instances, SUBSTRATE is a biological molecule, either a small bioactive ligand, or a biopolymer.

In certain embodiments, in Formula VIII, one or more of $R_1$-$R_{11}$ and $R_{15}$-$R_{20}$ includes a L-SUBSTRATE. In certain embodiments, in Formula VIII, two of $R_1$-$R_{11}$ and $R_{15}$-$R_{20}$ includes a L-SUBSTRATE.

In some embodiments, the dye conjugate is described by Formula IX:

where n and $R_1$-$R_{11}$ and $R_{15}$-$R_{22}$ are as described above for Formula III except that RGM is substrate, and m is 1 to 50.

In certain embodiments, in formula X, m is 1 to 50, such as 3 to 35, 6 to 35, 10 to 35 or 15 to 20. In some instances, 1 to about 50 dye molecules are conjugated to the SUBSTRATE, such as about 3 to about 35 dye molecules, about 6 to about 35 dye molecules, about 10 to about 35 dye molecules, or about 15 to about 20 dye molecules per SUBSTRATE. In some embodiments, as many as about 35 dye molecules can be conjugated to the SUBSTRATE without significant self-quenching. In certain instances, m is 1, 2, 3, 4, 5, 6, 7, 8, 9, 10, 11, 12, 13, 14, 15, 20, 25, 30, 35, 40, 45 or 50. In certain instances, m is about 5, about 10, about 15, about 20, about 25, about 30, about 35, about 40, about 45 or about 50.

In some embodiments, in Formula IX, n is 0. In some embodiments, in Formula IX, n is 1. In some embodiments, in Formula IX, n is 2. In some embodiments, in Formula IX, n is 3.

In certain cases, in Formula IX, $R_1$-$R_3$ are independently a hydrogen, a halogen, an alkyl having 1-20 carbons, a cycloalkyl having 3-20 carbons, an aryl, a heteroaryl, an amino, an alkylamino, an arylamino, a thiol, an alkylthiol, an arylthiol, a heteroarylthiol, a polyethyleneglycol, an alkoxy, an aryloxy, a carboxyalkyl, or a L-RGM. In certain instances, in Formula IX, $R_1$-$R_3$ are each a hydrogen. In certain cases, in Formula IX, two of $R_1$-$R_3$ are cyclically linked to form a six-membered carbocycle or heterocycle ring. In certain embodiments, in Formula IX, one of $R_1$-$R_3$ is an alkoxy, an aryloxy, or a L-RGM.

In some embodiments, in Formula IX, $R_4$ and $R_5$ are independently an alkyl having 1-20 carbons, a cycloalkyl having 3-20 carbons, an arylalkyl, a heteroarylalkyl, a carboxyalkyl, a sulfoalkyl, or a L-RGM. In certain embodiments, in Formula IX, $R_4$ and $R_5$ are each independently an alkyl having 1-20 carbons, a carboxyalkyl, a sulfoalkyl, or a L-RGM. In some cases, in Formula IX, $R_4$ and $R_5$ are each independently selected from an alkyl having 1-20 carbons, where the alkyl may be substituted with one or more substituents selected from a RGM, a sulfonate, a phosphate, amino, a substituted amino, an ammonium, a carboxy, and a hydroxyl. In certain embodiments, $R_4$ and $R_5$ are each independently selected from —$(CH_2)_m$—Z, where m is 1-12 and Z is selected from —H, —$CO_2H$, —$NH_2$, —$SO_3^-$, —$PO_3H$ and RGM.

In some embodiments, in Formula IX, $R_6$, $R_7$, $R_{15}$ and $R_{16}$ are independently an alkyl having 1-20 carbons, a cycloalkyl having 3-20 carbons, an aryl, an arylalkyl, a heteroaryl, a heteroarylalkyl, a carboxyalkyl, a carboxyaryl, a sulfoalkyl, or a L-RGM. In certain instances, in Formula IX, $R_6$, $R_7$, $R_{15}$ and $R_{16}$ are each independently an alkyl having 1-20 carbons. In certain instances, in Formula IX, $R_6$, $R_7$, $R_{15}$ and $R_{16}$ are each independently a lower alkyl. In certain instances, in Formula IX, $R_6$ and $R_7$ are each methyl. In certain instances,

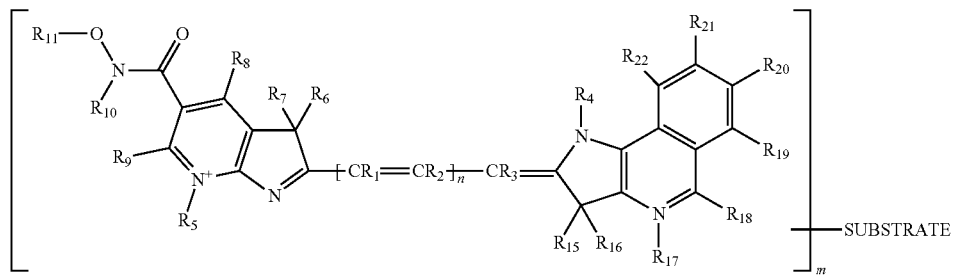

Formula IX in Formula IX, $R_{15}$ and $R_{16}$ are each methyl. In some embodiments, $R_6$ is a lower alkyl (e.g., a methyl or an ethyl) and $R_7$ is L-RGM. In some embodiments, $R_7$ is L-Z (e.g., —$(CH_2)_m$—Z, where m is 1-12 and Z is selected from —H, —$CO_2H$, —$NH_2$, —$SO_3^-$, —$PO_3H$ and RGM.) In some embodiments, $R_{15}$ is a lower alkyl (e.g., a methyl or an ethyl) and $R_{16}$ is L-RGM. In some embodiments, $R_{16}$ is L-Z (e.g., —$(CH_2)_m$—Z, where m is 1-12 and Z is selected from —H, —$CO_2H$, —$NH_2$, —$SO_3^-$, —$PO_3H$ and RGM.)

In some embodiments, in Formula IX, $R_8$, $R_9$ and $R_{17}$-$R_{22}$ are independently a hydrogen, an alkyl having 1-20 carbons, a hydroxy, an alkoxy having 1-20 carbons, a trifluoromethyl, a halogen, a methylthio, a carbonyl, an amino, a thiol, a sulfonate, a phosphonyl, or a L-RGM. In some instances, in Formula IX, $R_8$, $R_9$ and $R_{17}$-$R_{22}$ are each independently a hydrogen or an alkyl having 1-20 carbons. In some instances, in Formula IX, $R_8$, $R_9$ and $R_{17}$-$R_{22}$ are independently a hydrogen or L-RGM. In some instances, in Formula IX, $R_8$ and $R_9$ are each hydrogen. In some instances, in Formula IX, $R_{17}$-$R_{22}$ are each hydrogen. In certain embodiments, $R_9$ is cyclically linked to the adjacent N of the azaindoline ring, e.g., to form a 6 membered ring.

In some embodiments, in Formula IX, $R_{10}$ and $R_{11}$ are each independently hydrogen, an alkyl, an aryl, an arylalkyl, a heteroaryl, a heteroarylalkyl, a carboxyalkyl, a sulfoalkyl, or a L-RGM. In certain embodiments, in Formula IX, $R_{10}$ and $R_{11}$ are each independently hydrogen, an alkyl, an aryl or L-RGM. In some instances, in Formula IX, $R_{10}$ and $R_{11}$ are each independently an alkyl, such as a lower alkyl (e.g., methyl, ethyl, propyl, isopropyl, etc.). In certain instances, in Formula IX, $R_{10}$ is L-RGM. In certain cases, in Formula II, $R_{11}$ is L-RGM.

In some embodiments, in Formula IX, one or more of $R_4$ and $R_5$, $R_6$ and $R_7$, $R_5$ and $R_9$, $R_{15}$ and $R_{16}$, $R_4$ and $R_{22}$, $R_4$ and $R_6/R_7$, or $R_6/R_7$ and $R_{15}/R_{16}$ might be taken in combination to form a 5- to 50-membered ring (e.g., a 5- to 12-membered ring, such as a 5, 6, 7 or 8-membered ring).

In some cases, L is none, an alkyl, or a polyethyleneglycol. In certain instances, SUBSTRATE is a biological molecule, either a small bioactive ligand, or a biopolymer.

In some instances, in Formula IX, at least one of $R_1$-$R_{11}$ and $R_{15}$-$R_{20}$ includes a L-SUBSTRATE. In certain embodiments, in Formula III, two of $R_1$-$R_{11}$ and $R_{15}$-$R_{22}$ include a L-SUBSTRATE.

In some instances, the dye conjugate is described by Formula X:

dye molecules, about 10 to about 35 dye molecules, or about 15 to about 20 dye molecules per SUBSTRATE. In some embodiments, as many as about 35 dye molecules can be conjugated to the SUBSTRATE without significant self-quenching. In certain instances, m is 1, 2, 3, 4, 5, 6, 7, 8, 9, 10, 11, 12, 13, 14, 15, 20, 25, 30, 35, 40, 45 or 50. In certain instances, m is about 5, about 10, about 15, about 20, about 25, about 30, about 35, about 40, about 45 or about 50.

In some embodiments, in Formula X, n is 0. In some embodiments, in Formula X, n is 1. In some embodiments, in Formula X, n is 2. In some embodiments, in Formula X, n is 3.

In certain cases, in Formula X, $R_1$-$R_3$ are independently a hydrogen, a halogen, an alkyl having 1-20 carbons, a cycloalkyl having 3-20 carbons, an aryl, a heteroaryl, an amino, an alkylamino, an arylamino, a thiol, an alkylthiol, an arylthiol, a heteroarylthiol, a polyethyleneglycol, an alkoxy, an aryloxy, a carboxyalkyl, or a L-SUBSTRATE. In certain instances, in Formula X, $R_1$-$R_3$ are each a hydrogen. In certain cases, in Formula X, two of $R_1$-$R_3$ are cyclically linked to form a six-membered carbocycle or heterocycle ring. In certain embodiments, in Formula X, one of $R_1$-$R_3$ is an alkoxy, an aryloxy, or a L-SUBSTRATE.

In some embodiments, in Formula X, $R_4$ and $R_5$ are independently an alkyl having 1-20 carbons, a cycloalkyl having 3-20 carbons, an arylalkyl, a heteroarylalkyl, a carboxyalkyl, a sulfoalkyl, or a L-SUBSTRATE. In certain embodiments, in Formula X, $R_4$ and $R_5$ are each independently an alkyl having 1-20 carbons, a carboxyalkyl, a sulfoalkyl, or a L-SUBSTRATE. In some cases, in Formula X, $R_4$ and $R_5$ are each independently selected from an alkyl having 1-20 carbons, where the alkyl may be substituted with one or more substituents selected from a SUBSTRATE, a sulfonate, a phosphate, amino, a substituted amino, an ammonium, a carboxy, and a hydroxyl. In certain embodiments, $R_4$ and $R_5$ are each independently selected from —$(CH_2)_m$—Z, where m is 1-12 and Z is selected from —H, —$CO_2H$, —$NH_2$, —$SO_3^-$, —$PO_3H$ and SUBSTRATE.

In some embodiments, in Formula X, $R_6$, $R_7$, $R_{15}$ and $R_{16}$ are independently an alkyl having 1-20 carbons, a cycloalkyl having 3-20 carbons, an aryl, an arylalkyl, a heteroaryl, a heteroarylalkyl, a carboxyalkyl, a carboxyaryl, a sulfoalkyl, or a L-SUBSTRATE. In certain instances, in Formula X, $R_6$, $R_7$, $R_{15}$ and $R_{16}$ are each independently an alkyl having 1-20 carbons. In certain instances, in Formula X, $R_6$, $R_7$, $R_{15}$ and $R_{16}$ are each independently a lower alkyl. In certain instances,

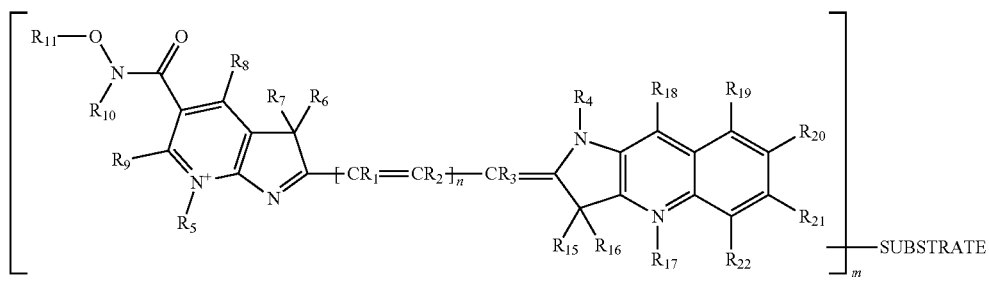

Formula X where n and $R_1$-$R_{11}$ and $R_{15}$-$R_{22}$ are as described above for Formula IV except that RGM is substrate, and m is 1 to 50.

In certain embodiments, in formula X, m is 1 to 50, such as 3 to 35, 6 to 35, 10 to 35 or 15 to 20. In some instances, 1 to about 50 dye molecules are conjugated to the SUBSTRATE, such as about 3 to about 35 dye molecules, about 6 to about 35 in Formula X, $R_6$ and $R_7$ are each methyl. In certain instances, in Formula X, $R_{15}$ and $R_{16}$ are each methyl. In some embodiments, $R_6$ is a lower alkyl (e.g., a methyl or an ethyl) and $R_7$ is L-SUBSTRATE. In some embodiments, $R_7$ is L-Z (e.g., —$(CH_2)_m$—Z, where m is 1-12 and Z is selected from —H, —$CO_2H$, —$NH_2$, —$SO_3^-$, —$PO_3H$ and SUBSTRATE.) In some embodiments, $R_{15}$ is a lower alkyl (e.g., a methyl or an ethyl) and $R_{16}$ is L-SUBSTRATE. In some embodiments, $R_{16}$ is L-Z (e.g., —$(CH_2)_m$—Z, where m is 1-12 and Z is selected from —H, —$CO_2H$, —$NH_2$, —$SO_3^-$, —$PO_3H$ and SUBSTRATE.)

In some embodiments, in Formula X, $R_8$, $R_9$ and $R_{17}$-$R_{22}$ are independently a hydrogen, an alkyl having 1-20 carbons, a hydroxy, an alkoxy having 1-20 carbons, a trifluoromethyl, a halogen, a methylthio, a carbonyl, an amino, a thiol, a sulfonate, a phosphonyl, or a L-SUBSTRATE. In some instances, in Formula X, $R_8$, $R_9$ and $R_{17}$-$R_{22}$ are each independently a hydrogen or an alkyl having 1-20 carbons. In some instances, in Formula X, $R_8$, $R_9$ and $R_{17}$-$R_{22}$ are independently a hydrogen or L-SUBSTRATE. In some instances, in Formula X, $R_8$ and $R_9$ are each hydrogen. In some instances, in Formula X, $R_{17}$-$R_{22}$ are each hydrogen. In certain embodiments, $R_9$ is cyclically linked to the adjacent N of the azaindoline ring, e.g., to form a 6 membered ring.

In some embodiments, in Formula X, $R_{10}$ and $R_{11}$ are each independently hydrogen, an alkyl, an aryl, an arylalkyl, a heteroaryl, a heteroarylalkyl, a carboxyalkyl, a sulfoalkyl, or a L-SUBSTRATE. In certain embodiments, in Formula X, $R_{10}$ and $R_{11}$ are each independently hydrogen, an alkyl, an aryl or L-SUBSTRATE. In some instances, in Formula X, $R_{10}$ and $R_{11}$ are each independently an alkyl, such as a lower alkyl (e.g., methyl, ethyl, propyl, isopropyl, etc.). In certain instances, in Formula X, $R_{10}$ is L-SUBSTRATE. In certain cases, in Formula II, $R_{11}$ is L-SUBSTRATE.

In some embodiments, in Formula X, one or more of $R_4$ and $R_5$, $R_6$ and $R_7$, $R_5$ and $R_9$, $R_{15}$ and $R_{16}$, $R_4$ and $R_{22}$, $R_4$ and $R_6/R_7$, or $R_6/R_7$ and $R_{15}/R_{16}$ might be taken in combination to form a 5- to 50-membered ring (e.g., a 5- to 12-membered ring, such as a 5, 6, 7 or 8-membered ring).

In some cases, L is none, an alkyl, or a polyethyleneglycol. In certain instances, SUBSTRATE is a biological molecule, either a small bioactive ligand, or a biopolymer. In certain embodiments, in Formula X, at least one of $R_1$-$R_{11}$ and $R_{15}$-$R_{22}$ includes a L-SUBSTRATE. In certain embodiments, in Formula X, two of $R_1$-$R_{11}$ and $R_{15}$-$R_{22}$ include a L-SUBSTRATE.

In some embodiments, the conjugate is a compound of Formula XI:

embodiments, as many as about 35 dye molecules can be conjugated to the SUBSTRATE without significant self-quenching. In certain instances, m is 1, 2, 3, 4, 5, 6, 7, 8, 9, 10, 11, 12, 13, 14, 15, 20, 25, 30, 35, 40, 45 or 50. In certain instances, m is about 5, about 10, about 15, about 20, about 25, about 30, about 35, about 40, about 45 or about 50.

In certain cases, in formula XI, $R_1$-$R_3$ are each independently a hydrogen, or a L-SUBSTRATE; $R_4$ and $R_5$ are each independently an alkyl having 1-20 carbons, a carboxyalkyl, a sulfoalkyl, or a L-SUBSTRATE; $R_6$, $R_7$, $R_{15}$ and $R_{16}$ are each independently an alkyl having 1-20 carbons, a cycloalkyl having 3-20 carbons, a carboxyalkyl, a carboxylaryl, a sulfoalkyl, or a L-SUBSTRATE; $R_8$, $R_9$ and $R_{17}$-$R_{22}$ are each independently a hydrogen, an alkyl having 1-20 carbons, a sulfonate, or a L-SUBSTRATE; and $R_{10}$ and $R_{11}$ are each independently an alkyl, a carboxyalkyl, or a L-SUBSTRATE.

In some embodiments, in formula XI, $R_1$-$R_3$ are each hydrogen; $R_4$ and $R_5$ are independently an alkyl having 1-20 carbons, a carboxyalkyl, a sulfoalkyl, or a L-SUBSTRATE; $R_6$, $R_7$, $R_{15}$ and $R_{16}$ are each independently an alkyl having 1-20 carbons, a cycloalkyl having 3-20 carbons, an aryl, an arylalkyl, a carboxyalkyl, a carboxylaryl, a sulfoalkyl, or a L-SUBSTRATE; $R_8$, $R_9$ and $R_{17}$-$R_{22}$ are each independently a hydrogen or a sulfonate; and $R_{10}$ and $R_{11}$ are each independently an alkyl, or a L-SUBSTRATE.

In some cases, L is none, an alkyl, or a polyethyleneglycol. In certain instances, SUBSTRATE is a biological molecule, either a small bioactive ligand, or a biopolymer.

In some embodiments, in Formula XI, n is 0. In some embodiments, in Formula XI, n is 1. In some embodiments, in Formula XI, n is 2. In some embodiments, in Formula XI, n is 3.

In certain cases, in Formula XI, $R_1$-$R_3$ are independently a hydrogen, a halogen, an alkyl having 1-20 carbons, a cycloalkyl having 3-20 carbons, an aryl, a heteroaryl, an amino, an alkylamino, an arylamino, a thiol, an alkylthiol, an arylthiol, a heteroarylthiol, a polyethyleneglycol, an alkoxy, an aryloxy, a carboxyalkyl, or a L-SUBSTRATE. In certain instances, in Formula XI, $R_1$-$R_3$ are each a hydrogen. In certain cases, in Formula XI, two of $R_1$-$R_3$ are cyclically linked to form a six-membered carbocycle or heterocycle

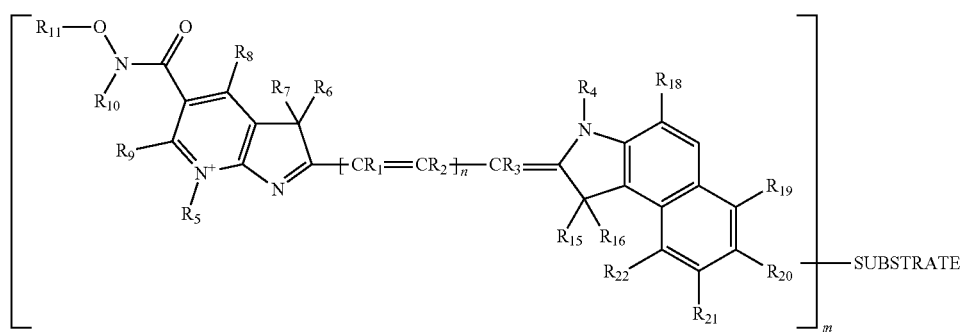

Formula XI where n and $R_1$-$R_{11}$ and $R_{15}$-$R_{22}$ are as described above for Formula V except that RGM is substrate, and m is 1 to 50.

In certain embodiments, in formula XI, m is 1 to 50, such as 3 to 35, 6 to 35, 10 to 35 or 15 to 20. In some instances, 1 to about 50 dye molecules are conjugated to the SUBSTRATE, such as about 3 to about 35 dye molecules, about 6 to about 35 dye molecules, about 10 to about 35 dye molecules, or about 15 to about 20 dye molecules per SUBSTRATE. In some ring. In certain embodiments, in Formula XI, one of $R_1$-$R_3$ is an alkoxy, an aryloxy, or a L-SUBSTRATE.

In some embodiments, in Formula XI, $R_4$ and $R_5$ are independently an alkyl having 1-20 carbons, a cycloalkyl having 3-20 carbons, an arylalkyl, a heteroarylalkyl, a carboxyalkyl, a sulfoalkyl, or a L-SUBSTRATE. In certain embodiments, in Formula XI, $R_4$ and $R_5$ are each independently an alkyl having 1-20 carbons, a carboxyalkyl, a sulfoalkyl, or a L-SUB- STRATE. In some cases, in Formula XI, $R_4$ and $R_5$ are each independently selected from an alkyl having 1-20 carbons, where the alkyl may be substituted with one or more substituents selected from a SUBSTRATE, a sulfonate, a phosphate, amino, a substituted amino, an ammonium, a carboxy, and a hydroxyl. In certain embodiments, $R_4$ and $R_5$ are each independently selected from —$(CH_2)_m$—Z, where m is 1-12 and Z is selected from —H, —$CO_2H$, —$NH_2$, —$SO_3^-$, —$PO_3H$ and SUBSTRATE.

In some embodiments, in Formula XI, $R_6$, $R_7$, $R_{15}$ and $R_{16}$ are independently an alkyl having 1-20 carbons, a cycloalkyl having 3-20 carbons, an aryl, an arylalkyl, a heteroaryl, a heteroarylalkyl, a carboxyalkyl, a carboxyaryl, a sulfoalkyl, or a L-SUBSTRATE. In certain instances, in Formula XI, $R_6$, $R_7$, $R_{15}$ and $R_{16}$ are each independently an alkyl having 1-20 carbons. In certain instances, in Formula XI, $R_6$, $R_7$, $R_{15}$ and $R_{16}$ are each independently a lower alkyl. In certain instances, in Formula XI, $R_6$ and $R_7$ are each methyl. In certain instances, in Formula XI, $R_{15}$ and $R_{16}$ are each methyl. In some embodiments, $R_6$ is a lower alkyl (e.g., a methyl or an ethyl) and $R_7$ is L-SUBSTRATE. In some embodiments, $R_7$ is L-Z (e.g., —$(CH_2)_m$—Z, where m is 1-12 and Z is selected from —H, —$CO_2H$, —$NH_2$, —$SO_3^-$, —$PO_3H$ and SUBSTRATE.) In some embodiments, $R_{15}$ is a lower alkyl (e.g., a methyl or an ethyl) and $R_{16}$ is L-SUBSTRATE. In some embodiments, $R_{16}$ is L-Z (e.g., —$(CH_2)_m$—Z, where m is 1-12 and Z is selected from —H, —$CO_2H$, —$NH_2$, —$SO_3^-$, —$PO_3H$ and SUBSTRATE.)

In some embodiments, in Formula XI, $R_8$, $R_9$ and $R_{17}$-$R_{22}$ are independently a hydrogen, an alkyl having 1-20 carbons, a hydroxy, an alkoxy having 1-20 carbons, a trifluoromethyl, a halogen, a methylthio, a carbonyl, an amino, a thiol, a sulfonate, a phosphonyl, or a L-SUBSTRATE. In some instances, in Formula XI, $R_8$, $R_9$ and $R_{17}$-$R_{22}$ are each independently a hydrogen or an alkyl having 1-20 carbons. In some instances, in Formula XI, $R_8$, $R_9$ and $R_{17}$-$R_{22}$ are independently a hydrogen or L-SUBSTRATE. In some instances, in Formula XI, $R_8$ and $R_9$ are each hydrogen. In some instances, in Formula XI, $R_{17}$-$R_{22}$ are each hydrogen. In certain embodiments, $R_9$ is cyclically linked to the adjacent N of the azaindoline ring, e.g., to form a 6 membered ring.

In some embodiments, in Formula XI, $R_{10}$ and $R_{11}$ are each independently hydrogen, an alkyl, an aryl, an arylalkyl, a heteroaryl, a heteroarylalkyl, a carboxyalkyl, a sulfoalkyl, or a L-SUBSTRATE. In certain embodiments, in Formula XI, $R_{10}$ and $R_{11}$ are each independently hydrogen, an alkyl, an aryl or L-SUBSTRATE. In some instances, in Formula XI, $R_{10}$ and $R_{11}$ are each independently an alkyl, such as a lower alkyl (e.g., methyl, ethyl, propyl, isopropyl, etc.). In certain instances, in Formula XI, $R_{10}$ is L-SUBSTRATE. In certain cases, in Formula II, $R_{11}$ is L-SUBSTRATE.

In some embodiments, in Formula XI, one or more of $R_4$ and $R_5$, $R_6$ and $R_7$, $R_5$ and $R_9$, $R_{15}$ and $R_{16}$, $R_4$ and $R_{22}$, $R_4$ and $R_6/R_7$, or $R_6/R_7$ and $R_{15}/R_{16}$ might be taken in combination to form a 5- to 50-membered ring (e.g., a 5- to 12-membered ring, such as a 5, 6, 7 or 8-membered ring).

In certain embodiments, in Formula XI, at least one of $R_1$-$R_{11}$ and $R_{15}$-$R_{22}$ includes a L-SUBSTRATE. In certain embodiments, in Formula XI, two of $R_1$-$R_{11}$ and $R_{15}$-$R_{22}$ include a L-SUBSTRATE.

In certain instances, the conjugate is a compound of Formula XII:

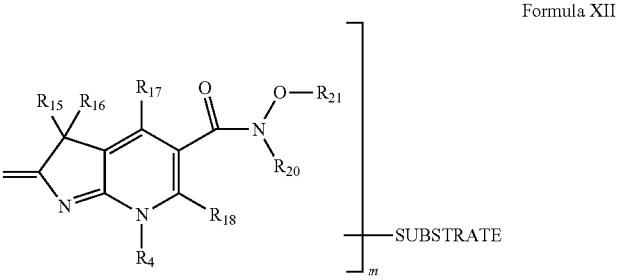

Formula XII where n and $R_1$-$R_{11}$, $R_{15}$-$R_{18}$, $R_{20}$ and $R_{21}$ are as described above for Formula VI except that RGM is substrate, and m is 1 to 50.

In some cases, in Formula XII, m is 1 to 50, such as 3 to 35, 6 to 35, 10 to 35 or 15 to 20. In some instances, 1 to about 50 dye molecules are conjugated to the SUBSTRATE, such as about 3 to about 35 dye molecules, about 6 to about 35 dye molecules, about 10 to about 35 dye molecules, or about 15 to about 20 dye molecules per SUBSTRATE. In some embodiments, as many as about 35 dye molecules can be conjugated to the SUBSTRATE without significant self-quenching. In certain instances, m is 1, 2, 3, 4, 5, 6, 7, 8, 9, 10, 11, 12, 13, 14, 15, 20, 25, 30, 35, 40, 45 or 50. In certain instances, m is about 5, about 10, about 15, about 20, about 25, about 30, about 35, about 40, about 45 or about 50.

In some instances, in Formula XII, $R_1$-$R_3$ are independently a hydrogen, a halogen, an alkyl having 1-20 carbons, a cycloalkyl having 3-20 carbons, an aryl, a heteroaryl, an amino, an alkylamino, an arylamino, a thiol, an alkylthiol, an arylthiol, a heteroarylthiol, a polyethyleneglycol, an alkoxy, an aryloxy, a carboxyalkyl, or a L-SUBSTRATE; $R_4$ and $R_5$ are independently an alkyl having 1-20 carbons, a cycloalkyl having 3-20 carbons, an arylalkyl, a heteroarylalkyl, a carboxyalkyl, or a L-SUBSTRATE; $R_6$, $R_7$, $R_{15}$ and $R_{16}$ are independently an alkyl having 1-20 carbons, a cycloalkyl having 3-20 carbons, an aryl, an arylalkyl, a heteroaryl, a heteroarylalkyl, a carboxyalkyl, a carboxyaryl, or a L-SUBSTRATE; $R_8$, $R_9$, $R_{17}$ and $R_{18}$ are independently a hydrogen, an alkyl having 1-20 carbons, a hydroxy, an alkoxy having 1-20 carbons, a trifluoromethyl, a halogen, a methylthio, a sulfonate, a carbonyl, an amino, a thiol, a phosphonate, or a L-SUBSTRATE; $R_{10}$, $R_{11}$, $R_{20}$ and $R_{21}$ are a hydrogen, an alkyl, an aryl, an arylalkyl, a heteroaryl, a heteroarylalkyl, a carboxyalkyl, a sulfonylalkyl, or a L-SUBSTRATE; L is a linker between SUBSTRATE and dye; SUBSTRATE is a biological molecule, either a small bioactive ligand, or a biopolymer; One or more of $R_4$ and $R_5$, $R_6$ and $R_7$, $R_5$ and $R_9$, $R_{15}$ and $R_{16}$, $R_4$ and $R_{18}$, $R_4$ and $R_6/R_7$, or $R_6/R_7$ and $R_{15}/R_{16}$ might be taken in combination to form a 5- to 50-membered ring.

In certain cases, $R_1$-$R_3$ are each hydrogen. In certain cases, in Formula XII, two of $R_1$-$R_3$ are cyclically linked to form a six-membered carbocycle or heterocycle ring. In certain embodiments, in Formula XII, one of $R_1$-$R_3$ is an alkoxy, an aryloxy, or a L-SUBSTRATE.

In some cases, in Formula XII, $R_4$ and $R_5$ are each independently selected from an alkyl having 1-20 carbons, where the alkyl may be substituted with one or more substituents selected from a SUBSTRATE, a sulfonate, a phosphate, amino, a substituted amino, an ammonium, a carboxy, and a hydroxyl. In certain embodiments, $R_4$ and $R_5$ are each independently selected from —$(CH_2)_m$—Z, where m is 1-12 and Z is selected from —H, —$CO_2H$, —$NH_2$, —$SO_3^-$, —$PO_3H$ and SUBSTRATE.

In certain instances, in Formula XII, $R_6$ and $R_7$ are each independently an alkyl having 1-20 carbons. In certain instances, in Formula XII, $R_6$ and $R_7$ are each independently a lower alkyl. In certain instances, in Formula XII, $R_6$ and $R_7$ are each methyl. In some embodiments, $R_6$ is a lower alkyl (e.g., a methyl or an ethyl) and $R_7$ is L-SUBSTRATE. In some embodiments, $R_7$ is L-Z (e.g., —$(CH_2)_m$—Z, where m is 1-12 and Z is selected from —H, —$CO_2H$, —$NH_2$, —$SO_3^-$, —$PO_3H$ and SUBSTRATE).

In some instances, in Formula XII, $R_8$ and $R_9$ are each independently a hydrogen or an alkyl having 1-20 carbons. In some instances, in Formula XII, $R_8$ and $R_9$ are each independently a hydrogen or L-SUBSTRATE. In some instances, in Formula XII, $R_8$ and $R_9$ are each hydrogen. In certain embodiments, $R_9$ is cyclically linked to the adjacent N of the azaindoline ring, e.g., to form a 6 membered ring.

In some instances, in Formula XII, $R_{17}$ and $R_{18}$ are each independently a hydrogen or an alkyl having 1-20 carbons. In some instances, in Formula XII, $R_{17}$ and $R_{18}$ are each independently a hydrogen or L-SUBSTRATE. In some instances, in Formula XII, $R_{17}$ and $R_{18}$ are each hydrogen. In certain embodiments, $R_{18}$ is cyclically linked to the adjacent N—R4 of the azaindoline ring, e.g., to form a 6 membered ring.

In some instances, in formula XII, $R_1$-$R_3$ are each independently a hydrogen, or a L-SUBSTRATE; $R_4$ and $R_5$ are each independently an alkyl having 1-20 carbons, a carboxyalkyl, a sulfoalkyl, or a L-SUBSTRATE; $R_6$, $R_7$, $R_{15}$ and $R_{16}$ are each independently an alkyl having 1-20 carbons, a cycloalkyl having 3-20 carbons, an aryl, an arylalkyl, a carboxyalkyl, carboxylaryl, a sulfoalkyl, or a L-SUBSTRATE; $R_8$, $R_9$ and $R_{17}$-$R_{22}$ are each independently a hydrogen, an alkyl having 1-20 carbons, a sulfonate, a phosphonyl or L-SUBSTRATE; and $R_{10}$ and $R_{11}$ are each independently an alkyl, an aryl, an arylalkyl, a carboxyalkyl, a sulfoalkyl, or a L-SUBSTRATE.

In certain instances, in formula XII, $R_1$-$R_3$ are each hydrogen; $R_4$ and $R_5$ are each independently an alkyl having 1-20 carbons, a carboxyalkyl, a sulfoalkyl, or a L-SUBSTRATE; $R_6$, $R_7$, $R_{15}$ and $R_{16}$ are each independently an alkyl having 1-20 carbons, a cycloalkyl having 3-20 carbons, a carboxyalkyl, a carboxylaryl, a sulfoalkyl, or a L-SUBSTRATE; $R_8$, $R_9$, $R_{17}$, and $R_{18}$ are each independently a hydrogen, 20 or a sulfonate; and $R_{10}$ and $R_{11}$ are each independently an alkyl, or a L-SUBSTRATE.

In certain cases, in formula XII, L is none, an alkyl, or a polyethyleneglycol. In certain instances, SUBSTRATE is a biological molecule, such as a small bioactive ligand, or a biopolymer.

In some cases, in Formula XII, n is 0. In some instances, in Formula XII, n is 1. In certain cases, in Formula XII, n is 2. In some cases, in Formula XII, n is 3.

In certain embodiments, in Formula XII, one or more of $R_1$-$R_{11}$, $R_{15}$-$R_{18}$ and $R_{20}$-$R_{21}$ includes a L-SUBSTRATE. In certain embodiments, in Formula XII, two of $R_1$-$R_{11}$, $R_{15}$-$R_{18}$ and $R_{20}$-$R_{21}$ includes a L-SUBSTRATE.

In some embodiments, the dye conjugate is derived from conjugation of any one of the reactive dyes of Table 1 with a compatible functional group of a substrate of interest (e.g., as described herein).

In some embodiments, in the dye conjugate, $R^4$ and $R^5$ are each independently —$(CH_2)_q$—Z, wherein Z is a water-soluble group and q is an integer from 1 to 12. In certain embodiments, Z is $SO_3H$ and n is 3.

In some embodiments, in the dye conjugate, $R^{15}$ is a lower alkyl and $R^{16}$ is —$(CH_2)_m$—Y-RGM, where Y is a cycloalkyl, a heterocycloalkyl, a heterocycle, or an aryl and m is 0 or an integer from 1 to 6. In some instances, Y is a phenyl, a pyridyl, a cyclohexyl, or a piperidinyl. In certain embodiments, $R^{15}$ is methyl. In certain instances, RGM is an active ester. In some cases, Y is phenyl. In certain embodiments, $R^{16}$ is —$(CH_2)_m$-Ph-C(O)—NHS, where m is 0 or 1 and NHS is N-hydroxy succinimidyl.

In certain cases, in the dye conjugate, $R^6$ and $R^7$ are each independently a lower alkyl. In certain instances, $R^6$ and $R^7$ are each methyl.

In certain embodiments, the dye conjugate does not include a PEG-containing substituent. In certain embodiments, the dye conjugate does not include a water-soluble polyalkylene oxide polymer of MW 300 to 5000.

In certain embodiments, the dye conjugate does not include a cleavable linker. In certain embodiments, the dye conjugate does not include a linker that includes a labile —C=N— group.

In certain embodiments, the conjugate is a polypeptide conjugate, which includes a polypeptide conjugated to a dye compound (e.g., as described above). The dye of interest can be conjugated to the polypeptide at any desired site of the polypeptide. Thus, the present disclosure provides, for example, a modified polypeptide having a dye conjugated at a site at or near the C-terminus of the polypeptide. Other examples include a modified polypeptide having a dye conjugated at a position at or near the N-terminus of the polypeptide. Examples also include a modified polypeptide having a dye conjugated at a position between the C-terminus and the N-terminus of the polypeptide (e.g., at an internal site of the polypeptide). Combinations of the above are also possible where the modified polypeptide is conjugated to two or more dyes.

Embodiments of the present disclosure include conjugates where a polypeptide is conjugated to one or more dyes, such as 2 dyes, 3 dyes, 4 dyes, 5 dyes, 6 dyes, 7 dyes, 8 dyes, 9 dyes, or 10 or more dyes. The dyes may be conjugated to the polypeptide at one or more sites in the polypeptide. For example, one or more dyes may be conjugated to a single amino acid residue of the polypeptide. In some cases, one dye is conjugated to an amino acid residue of the polypeptide. In other embodiments, two dyes may be conjugated to the same amino acid residue of the polypeptide. In other embodiments, a first dye is conjugated to a first amino acid residue of the polypeptide and a second dye is conjugated to a second amino acid residue of the polypeptide. Combinations of the above are also possible, for example where a polypeptide is conjugated to a first dye at a first amino acid residue and conjugated to two other dyes at a second amino acid residue. Other combinations are also possible, such as, but not limited to, a polypeptide conjugated to first and second dyes at a first amino acid residue and conjugated to third and fourth moieties at a second amino acid residue, etc. In some instances, the polypeptide is an antibody.

In some embodiments, the dye conjugates find use in biological assays, where the substrate may be an amino acid, a nucleotide, or a biopolymer, such as an amino acid polymer, a nucleic acid polymer, a carbohydrate, or a polysaccharide. Dye-polymer conjugates can be prepared that incorporate a plurality of dye molecules conjugated to the substrate to increase the fluorescent signal from the dye-conjugate.

In some embodiments, the substrate is an amino acid or an amino acid polymer, such as a peptide or protein. Amino acid polymers of interest include, but are not limited to, antibodies (e.g., as defined, above), IgG-binding proteins (e.g., protein A, protein G, protein A/G, etc.), enzymes, lectins, glycoproteins, histones, albumins, lipoproteins, avidin, streptavidin, protein A, protein G, phycobiliproteins and other fluorescent proteins, hormones, toxins, chemokines, growth factors, neuropeptides, cytokines, toxins, protease substrates, and protein kinase substrates. In certain embodiments, the biopolymer substrate is a monoclonal antibody.

In certain embodiments, the substrate is a nucleic acid base, nucleoside, nucleotide or a nucleic acid polymer. Nucleic acid polymers of interest include, but are not limited to, those that are modified to possess an additional linker or spacer for attachment of the dyes of the invention, such as an alkynyl linkage (see e.g., U.S. Pat. No. 5,047,519), an aminoallyl linkage (see e.g., U.S. Pat. No. 4,711,955), a heteroatom-substituted linker (see e.g., U.S. Pat. No. 5,684,142), or other linkage. In some embodiments, the conjugated substance is a nucleoside or nucleotide analog that links a purine or pyrimidine base to a phosphate or polyphosphate moiety through a noncyclic spacer. In certain embodiments, the dye is conjugated to the carbohydrate portion of a nucleotide or nucleoside, e.g., through a hydroxyl group or through a thiol or amino group (e.g., as described in U.S. Pat. Nos. 5,659,025; 5,668,268; 5,679,785). In some instances, the conjugated nucleotide is a nucleoside triphosphate or a deoxynucleoside triphosphate or a dideoxynucleoside triphosphate. Incorporation of methylene moieties or nitrogen or sulfur heteroatoms into the phosphate or polyphosphate moiety is also useful. Nonpurine and nonpyrimidine bases such as 7-deazapurines (see e.g., U.S. Pat. No. 6,150,510) and nucleic acids containing such bases can also be coupled to the subject dye compounds. Nucleic acid adducts prepared by reaction of depurinated nucleic acids with amine, hydrazide or hydroxylamine derivatives provide an additional means of labeling and detecting nucleic acids, see e.g. "A method for detecting abasic sites in living cells: age-dependent changes in base excision repair." Atamna et al., 2000, Proc Natl Acad Sci 97: 686-691.

Nucleic acid polymer conjugates of interest include, but are not limited to, labeled, single- or multi-stranded, natural or synthetic DNA or RNA, DNA or RNA oligonucleotides, or DNA/RNA hybrids, or nucleic acids that incorporate an unusual linker such as morpholine derivatized phosphates, or peptide nucleic acids such as N-(2-aminoethyl)glycine units. When the nucleic acid is a synthetic oligonucleotide, it may contain fewer than 50 nucleotides, e.g., fewer than 25 nucleotides. Conjugates of peptide nucleic acids (PNA) (see e.g., Nielsen et al U.S. Pat. No. 5,539,082) may be used for some applications because of their generally faster hybridization rates.

In some embodiments, the substrate is a carbohydrate that is a polysaccharide, such as a dextran, heparin, glycogen, amylopectin, mannan, inulin, starch, agarose or cellulose. Alternatively, the carbohydrate is a polysaccharide that is a lipopolysaccharide. Polysaccharide conjugates of interest include, but are not limited to, dextran and lipopolysaccharide conjugates.

In certain embodiments, the substrate is a lipid (e.g., having 6-60 carbons), including glycolipids, phospholipids, sphingolipids, and steroids. Alternatively, the conjugated substance is a lipid assembly, such as a liposome. The lipophilic moiety may be used to retain the conjugated substances in cells, e.g., as described in U.S. Pat. No. 5,208,148. Certain polar dyes of the invention may also be trapped within lipid assemblies.

Conjugates in which the substrate is an ion-complexing moiety may serve as indicators for calcium, sodium, magnesium, zinc, potassium, or other biologically important metal ions. Ion-complexing moieties of interest include, but are not limited to, crown ethers (see e.g., U.S. Pat. No. 5,405,975); derivatives of 1,2-bis-(2-aminophenoxyethane)-N,N,N',N'-tetraacetic acid (BAPTA chelators; see e.g., U.S. Pat. Nos. 5,453,517, 5,516,911, and 5,049,673); derivatives of 2-carboxymethoxyaniline-N,N-di-acetic acid (see e.g., APTRA chelators; Am. J. Physiol. 256, C540 (1989)); pyridine- and phenanthroline-based metal ion chelators (see e.g., U.S. Pat. No. 5,648,270); and derivatives of nitrilotriacetic acid, see e.g. "Single-step synthesis and characterization of biotinylated nitrilotriacetic acid, a unique reagent for the detection of histidine-tagged proteins immobilized on nitrocellulose", McMahan et al., 1996, Anal Biochem 236:101-106. The ion-complexing moiety may be a crown ether chelator, a BAPTA chelator, an APTRA chelator or a derivative of nitrilotriacetic acid.

Other conjugates of interest include non-biological materials, including but not limited to, dye-conjugates of organic or inorganic polymers, polymeric films, polymeric wafers, polymeric membranes, polymeric particles, or polymeric microparticles; including magnetic and non-magnetic microspheres; iron, gold or silver particles; conducting and non-conducting metals and non-metals; and glass and plastic surfaces and particles. Conjugates are optionally prepared by copolymerization of a dye that contains an appropriate functionality while preparing the polymer, or by chemical modification of a polymer that contains functional groups with suitable chemical reactivity. Other types of reactions that are useful for preparing dye-conjugates of polymers include catalyzed polymerizations or copolymerizations of alkenes and reactions of dienes with dienophiles, transesterifications or transaminations.

In some embodiments, dye-conjugates are further labeled with at least one second dye, which is optionally an additional dye of the present invention. In certain embodiments, the first and second dyes form an energy-transfer pair, e.g., a fluorescence energy transfer pair (FRET). In some aspects of the invention, the labeled conjugate functions as an enzyme substrate, and enzymatic hydrolysis disrupts the energy transfer.

In some instances, the fluorescent dye-conjugates, particularly where the substrate is a biopolymer, can incorporate multiple dyes per substrate molecule to increase the fluorescent signal. In some cases, 3 or more molecules of dyes are incorporated into dye-biopolymer conjugates. In some embodiments in which the biopolymer is an antibody, three or more, such as 4 or more, 5 or more or 6 or more dye molecules are conjugated to the antibody. In some instances, 1 to about 50 dye molecules are conjugated to the antibody, such as about 3 to about 35 dye molecules, about 6 to about 35 dye molecules, about 10 to about 35 dye molecules, or about 15 to about 20 dye molecules per antibody. In some embodiments, as many as about 35 dye molecules can be conjugated to the antibody without significant self-quenching. It is understood by one of skill in the art that each stated range of dyes per conjugate substrate is intended to describe all values within the range. Thus, for example, by stating that fluorescent biopolymers of the intention contain 6-15 dye molecules, biopolymers containing 6, 7, 8, . . . , or 15 dye molecules are also part of the invention. It is understood that the stated ranges and values of dyes per conjugate described herein may be an average value.

The substrate and the subject dye compound (e.g., as described above) may be conjugated to each other through a coupling moiety. In some cases, the substrate and the subject dye compound may each be bound (e.g., covalently bonded) to the coupling moiety, thus indirectly binding the substrate and the dye compound together. In some cases, the coupling moiety includes the product of a conjugation reaction between a RGM of the dye compound and a compatible functional group of the substrate. The substrate may contain such a functional group(s) or may be modified to contain such functional groups with suitable reactivity, resulting in chemical attachment to the dye to the substance. In some cases, the conjugation reaction between the reactive dye and the functional group(s) on the substrate results in one or more atoms of the reactive group RGM to be incorporated into a new linkage (e.g., coupling moiety) attaching the dye to the substrate.

In some cases, the substrate is an amino acid, a peptide, a protein, a tyramine, a polysaccharide, an ion-complexing moiety, a nucleoside, a nucleotide, an oligonucleotide, a nucleic acid, a hapten, a psoralen, a drug, a hormone, a lipid, a lipid assembly, a polymer, a polymeric microparticle, a biological cell or virus. In some instances, the substrate is a peptide, a protein, a nucleotide, an oligonucleotide, or a nucleic acid. When conjugating dyes of the invention to such biopolymers, it is possible to incorporate more dyes per molecule to increase the fluorescent signal. In certain instances, it is possible to incorporate three or more molecules of such dyes per molecule of antibody without loss of total fluorescence, whereas fluorescence of the spectrally comparable Cy5 (wherein n=2) is strongly quenched when greater than approximately two Cy5 dyes are incorporated per antibody. In some instances, the labeled conjugates of the invention are more fluorescent than conjugates of the spectrally similar cyanine dyes such as Alexa Fluor® 700 at the same antibody concentration.

In some embodiments, the substrate is an amino acid (such as amino acids that are protected or are substituted by phosphonates, carbohydrates, or $C_1$ to $C_{25}$ carboxylic acids), or is a polymer of amino acids such as a peptide or protein. In certain embodiments, the conjugates of peptides contain at least five amino acids, such as 5 to 36 amino acids. Peptides of interest include, but are not limited to, neuropeptides, cytokines, toxins, protease substrates, and protein kinase substrates. Protein conjugates of interest include enzymes, antibodies, lectins, glycoproteins, histones, albumins, lipoproteins, avidin, streptavidin, protein A, protein G, phycobiliproteins and other fluorescent proteins, hormones, toxins, chemokines and growth factors.

In some instances, the conjugated protein is a phycobiliprotein, such as allophycocyanin, phycocyanin, phycoerythrin, allophycocyanin B, B-phycoerythrin, and phycoerythrocyanin, (for example, see U.S. Pat. No. 5,714,386 to Roederer (1998)). In certain instances, the conjugates are conjugates of R-phycoerythrin and of allophycocyanin (APC) with selected dyes of the invention that serve as excited-state energy acceptors or donors. In these conjugates, excited state energy transfer results in long wavelength fluorescence emission when excited at relatively short wavelengths.

In some embodiments, the dye conjugate is part of a tandem conjugate with a second substrate. A tandem conjugate may include a dye conjugated to a fluorochrome (e.g., a fluorescent protein such as a phycobiliprotein) where the dye-fluorochrome conjugate is further conjugated to a substrate of interest. In some embodiments, the dye-fluorochrome conjugate is a dye-APC conjugate. In certain embodiments, the dye-APC conjugate is conjugated to a member of a specific binding pair, e.g., as described in Table 2. In some instances, the tandem conjugate is a dye-APC-antibody conjugate. In certain embodiments, the dye-APC conjugate includes one or more reactive group moieties for conjugating to a substrate of interest. As such, in some cases, the dye-APC conjugate may be referred to as a reactive dye (e.g., as described herein) Any convenient methods may be used in preparing the subject tandem conjugates. In one aspect of the invention, the substrate is a conjugated substance that is an antibody (including intact antibodies, antibody fragments, and antibody sera, etc.), an amino acid, an angiostatin or endostatin, an avidin or streptavidin, a biotin (e.g. an amidobiotin, a biocytin, a desthiobiotin, etc.), a blood component protein (e.g. an albumin, a fibrinogen, a plasminogen, etc.), a dextran, an enzyme, an enzyme inhibitor, an IgG-binding protein (e.g. a protein A, protein G, protein A/G, etc.), a fluorescent protein (e.g. a phycobiliprotein, an aequorin, a green fluorescent protein, etc.), a growth factor, a hormone, a lectin (e.g. a wheat germ agglutinin, a conconavalin A, etc.), a lipopolysaccharide, a metal-binding protein (e.g. a calmodulin, etc.), a microorganism or portion thereof (e.g. a bacteria, a virus, a yeast, etc.), a neuropeptide and other biologically active factors (e.g. a dermorphin, a deltropin, an endomorphin, an endorphin, a tumor necrosis factor etc.), a non-biological microparticle (e.g. of ferrofluid, gold, polystyrene, etc.), a nucleotide, an oligonucleotide, a peptide toxin (e.g. an apamin, a bungarotoxin, a phalloidin, etc.), a phospholipid-binding protein (e.g. an annexin, etc.), a small-molecule drug (e.g. a methotrexate, etc.), a structural protein (e.g. an actin, a fibronectin, a laminin, a microtubule-associated protein, a tublin, etc.), or a tyramide.

Preparation of Dye-Conjugates

The dye-conjugates of the present invention may be synthesized as the product of a reaction between a substrate and a subject dye (e.g., as described herein). A variety of chemically reactive groups (RGM) and compatible substrates, and bioconjugation chemistries may be utilized in preparing the subject dye conjugates (see e.g., Bioconjugate Techniques, Greg T. Hermanson, Academic Press, New York, 3rd Ed., 2013). The preparation of dye conjugates using reactive dyes may be achieved using any convenient methods, see, e.g., Hermanson, ibid; Haugland, 1995, Methods Mol. Biol. 45:205-21; and Brinkley, 1992, Bioconjugate Chemistry 3:2. Conjugates may result from mixing appropriate reactive dyes and the substrate to be conjugated in a suitable solvent in which both are soluble. Solutions of the reactive dyes described herein are readily created, facilitating conjugation reactions with any convenient substrates. For those reactive dyes that are photoactivated, conjugation may be achieved via illumination of the reaction mixture to activate the reactive dye.

The dye conjugates may be synthesized as the product of a reaction between a biopolymer and a reactive dye, wherein the reaction conditions result in the conjugation of multiple dye molecules to each biopolymer. In some cases, the dye biopolymer conjugates can be synthesized as a polymerization reaction of subunit molecules, wherein one or more of the subunit molecules have been conjugated to a reactive dye prior to polymerization of the biopolymer. An example of the latter method is the synthesis of oligonucleotides using standard phosphoramidite chemistry, where at least one phosphoramidite is dye-labeled.

In some cases, a chemically reactive group is an electrophile or nucleophile that can form a covalent linkage through exposure to a corresponding functional group that is a nucleophile or electrophile, respectively. Some examples of reactive pairs of electrophilic and nucleophilic groups, along with the covalent linkage resulting from their reaction, are shown in Table 3, below.

TABLE 3

Reactive Electrophilic and Nucleophilic Groups, and the Resulting Coupling Moieties

| Electrophilic Group | Nucleophilic Group | Resulting Conjugate |
|---|---|---|
| activated esters* | amines/anilines | carboxamides |
| acrylamides | thiols | thioethers |
| acyl azides** | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carbodiimides | carboxylic adds | N-acylureas or anhydrides |
| diazoalkanes | carboxylic acids | esters |
| epoxides | thiols | thioethers |
| haloacetamides | thiols | thioethers |
| haloplatinate | amino | platinum complex |
| haloplatinate | heterocycle | platinum complex |
| haloplatinate | thiol | platinum complex |
| halotriazines | amines/anilines | aminotriazines |
| halotriazines | alcohols/phenols | triazinyl ethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

*Activated esters, may have the formula —COW, where W is a good leaving group (e.g. succinimidyloxy (—OC$_4$H$_4$O$_2$) sulfosuccinimidyloxy (—OC$_4$H$_3$O$_2$—SO$_3$H), -1-oxybenzotriazolyl (—OC$_6$H$_4$N$_3$); or an aryloxy group or aryloxy substituted one or more times by electron withdrawing substituents such as nitro, fluoro, chloro, cyano, or trifluoromethyl, or combinations thereof, used to form activated aryl esters; or a carboxylic acid activated by a carbodiimide to form an anhydride or mixed anhydride —OCOAlk or —OCN(Alk$_1$)NH (Alk$_2$), where Alk$_1$ and Alk$_2$, which may be the same or different, are C$_1$-C$_{20}$ alkyl, C$_1$-C$_{20}$ perfluoroalkyl, or C$_1$-C$_{20}$ alkoxy; or cyclohexyl, 3-dimethylaminopropyl, or N-morpholinoethyl).
**Acyl azides can also rearrange to isocyanates.

The choice of the reactive group used to attach the dye to a substrate to be conjugated may depend on the functional group on the substance to be conjugated and the type or length of covalent linkage desired. The types of functional groups that may be present on the organic or inorganic substrate include, but are not limited to, amines, amides, thiols, alcohols, phenols, aldehydes, ketones, phosphates, imidazoles, hydrazines, hydroxylamines, disubstituted amines, halides, epoxides, carboxylate esters, sulfonate esters, purines, pyrimidines, carboxylic acids, olefinic bonds, or a combination of these groups. A single type of reactive site may be available on the substrate (e.g., as may occur for polysaccharides), or a variety of sites may occur (e.g. amines, thiols, alcohols, phenols), e.g., as may occur for proteins. A conjugated substrate may be conjugated to more than one dye, which may be the same or different, or to a substrate that is additionally modified by any convenient moiety (e.g., by a hapten, such as biotin). In some cases, selectivity can be obtained by careful control of the reaction conditions. In some cases, selectivity of labeling may be obtained by selection of a convenient reactive dye.

In some instances, the reactive group, RGM, reacts with an amine, a thiol, an alcohol, an aldehyde or a ketone. In certain cases, the RGM reacts with an amine or a thiol functional group. In certain embodiments, the RGM is an acrylamide, a reactive amine (including a cadaverine or ethylenediamine), an activated ester of a carboxylic acid (e.g., a succinimidyl ester of a carboxylic acid), an acyl azide, an acyl nitrile, an aldehyde, an alkyl halide, an anhydride, an aniline, an aryl halide, an azide, an aziridine, a boronate, a carboxylic acid, a diazoalkane, a haloacetamide, a halotriazine, a hydrazine (including hydrazides), an imido ester, an isocyanate, an isothiocyanate, a maleimide, a phosphoramidite, a reactive platinum complex, a sulfonyl halide, or a thiol group. By "reactive platinum complex" is particularly meant chemically reactive platinum complexes such as described in U.S. Pat. Nos. 5,580,990; 5,714,327; 5,985,566.

Where RGM is an activated ester of a carboxylic acid, the reactive dye may be useful for preparing dye-conjugates of proteins, nucleotides, oligonucleotides, or haptens. Where RGM is a maleimide or haloacetamide the reactive dye may be useful for conjugation to thiol-containing substances. Where RGM is a hydrazide, the reactive dye may be useful for conjugation to periodate-oxidized carbohydrates and glycoproteins, and, in addition, may be an aldehyde-fixable polar tracer for cell microinjection. In some instances, the RGM is a carboxylic acid, a succinimidyl ester of a carboxylic acid, a haloacetamide, a hydrazine, an isothiocyanate, a maleimide group, an aliphatic amine, a perfluorobenzamido, an azidoperfluorobenzamido group, or a psoralen. In certain instances, the RGM is a succinimidyl ester of a carboxylic acid, a maleimide, an iodoacetamide, or a reactive platinum complex. Alternatively, the reactive group, RGM, is a photoactivatable group in which case the dye becomes chemically reactive only after illumination with light of an appropriate wavelength. In some instances, the reactive group is a photoactivatable group, such as an azide, diazirinyl, azidoaryl, or psoralen derivative, and the dye becomes chemically reactive only after illumination with light of an appropriate wavelength.

In certain embodiments, the methods of biomolecule substrate conjugation are compatible with reaction conditions suitable for the biomolecule. For example, the reaction conditions may include a reaction mixture that includes water. In some cases, the reaction mixture may have a pH compatible with the polypeptide, such as, but not limited to, a pH of 4 to 11, or a pH of 5 to 10, or a pH of 6 to 9, or a pH of 6 to 8. In certain instances, the reaction mixture has a pH of 7. In some embodiments, the reaction conditions are performed at a temperature compatible with the polypeptide. For example, the reaction conditions may be at a temperature of 20° C. to 45° C., such as 25° C. to 40° C., or 30° C. to 40° C., or 35° C. to 40° C. In some cases, the reaction conditions are at room temperature (e.g., 25° C.). In some instances, the reaction conditions are at a temperature of 37° C. The ordinarily skilled artisan will appreciate that factors such as pH and steric hindrance (i.e., the accessibility of the modified amino acid residue to reaction with a reactive partner of interest) are of importance. Modifying reaction conditions to provide for optimal conjugation conditions is well within the skill of the ordinary artisan, and is routine in the art. Where conjugation is conducted with a polypeptide present in or on a living cell, the conditions are selected so as to be physiologically compatible. For example, the pH can be dropped temporarily for a time sufficient to allow for the reaction to occur but within a period tolerated by the cell (e.g., from about 30 min to 1 hour). Physiological conditions for conducting modification of polypeptides on a cell surface can be similar to those used in a ketone-azide reaction in modification of cells bearing cell-surface azides (see, e.g., U.S. Pat. No. 6,570,040).

In certain embodiments, the present disclosure provides a polypeptide conjugate, where the polypeptide is an antibody. As such, embodiments include an antibody conjugated to a moiety of interest, where an antibody conjugated to a moiety of interest is referred to as an "antibody conjugate." An Ig polypeptide generally includes at least an Ig heavy chain constant region or an Ig light chain constant region, and can further include an Ig variable region (e.g., a $V_L$ region and/or a $V_H$ region). Ig heavy chain constant regions include Ig constant regions of any heavy chain isotype, non-naturally occurring Ig heavy chain constant regions (including consensus Ig heavy chain constant regions). An Ig constant region can be modified to be conjugated to a moiety of interest, where the moiety of interest is present in or adjacent a solvent-accessible loop region of the Ig constant region.

Based on the above-mentioned attributes, reactive dyes of the invention are selected for the preparation of the desired dye-conjugates, whose advantageous properties make them useful for a wide variety of applications.

Methods

Aspects of the disclosure include methods of detecting an analyte in a sample. Contacting the sample with a detection reagent may result in labeling of the analyte and provide for detection of the analyte by fluorescence. In some instances, the analyte is labeled via complexation with the detection reagent. In certain instances, the analyte is labeled via conjugation to a detection reagent.

In some embodiments, the method includes contacting the sample with a detection reagent comprising a dye-conjugate (e.g., as described herein) under conditions in which the detection reagent forms a complex with the analyte. In certain embodiments, the contacting step occurs under conditions sufficient for the detection reagent to specifically bind the analyte.

In some cases, the detection reagent includes a specific binding moiety that specifically binds the analyte. In some embodiments, the method includes contacting the sample with a detection reagent comprising a reactive dye (e.g., as described herein) under conditions in which the detection reagent conjugates to the analyte.

As used herein, the terms "analyte" and "target" are used interchangeably and refer to any substance to be analyzed, detected, measured, or labeled. Analytes of interest include, but are not limited to, proteins, peptides, hormones, haptens, antigens, antibodies, receptors, enzymes, nucleic acids, polysaccharides, chemicals, polymers, pathogens, toxins, organic drugs, inorganic drugs, cells, tissues, microorganisms, viruses, bacteria, fungi, algae, parasites, allergens, pollutants, and combinations thereof. By convention, where cells of a given cell type are to be detected, either the cellular component molecules or the cell itself can be described as an analyte.

As used herein, the term "detection reagent" refers to any molecule that is used to facilitate optical detection of an analyte.

In some instances, the detection reagent includes a reactive dye (e.g., as described herein) that is capable of conjugation to an analyte of interest.

In some cases, the detection reagent includes a dye-conjugate in which the substrate component of the conjugate is, itself, an analyte-specific reagent. In some cases, the detection reagent includes an analyte-specific reagent conjugated to a fluorescent dye compound (e.g., as described herein). In some embodiments, the detection reagent includes an analyte-specific reagent conjugated to a dye-conjugate of a fluorescent protein (e.g., a tandem conjugate). In certain cases, the detection reagent includes a dye-conjugate that functions as the fluorescent label and an analyte specific reagent bound to the conjugate. In such cases, the dye-conjugate and the analyte specific reagent may be bound to each other covalently or non-covalently via any convenient methods.

As used herein, the terms "analyte-specific reagent" and "target-specific reagent" are used interchangeably to refer to any reagent that preferentially binds to an analyte or target of interest, relative to other analytes potentially present in a sample. A target (analyte) and target-specific (analyte-specific) reagent may be members of a specific binding pair (e.g., specific binding moieties), and either member of the pair can be used as the target-specific reagent in order to specifically bind to the other member of the pair. Target and target-specific reagent pairs of interest include, but are not limited to, those reagent pairs provided in the Table 2, below. In some instances, the target-specific reagents are antibodies that include an antigen binding site that specifically binds (immunoreacts with) an antigen.

TABLE 2

| Specific binding moiety pairs | |
|---|---|
| Antigen | Antibody |
| Biotin | Avidin, streptavidin, or anti-biotin Antibody |
| IgG (an immunoglobulin) | protein A or protein G |
| Drug | Drug receptor |
| Toxin | Toxin receptor |
| Carbohydrate | Lectin or carbohydrate receptor |
| Peptide | Peptide receptor |
| Nucleotide | Complimentary nucleotide |
| Protein | Protein receptor |
| Enzyme substrate | Enzyme |
| Nucleic acid | Nucleic acid |
| Hormone | Hormone receptor |
| Psoralen | Nucleic acid |
| Target molecule | RNA or DNA aptamer |

Any convenient protocol for contacting the sample with the dye compounds or dye conjugates may be employed. The particular protocol that is employed may vary, e.g., depending on whether the sample is in vitro or in vivo, and whether a dye compound or dye conjugate is used. For in vitro protocols, contact of the sample with the dye compound or dye conjugate may be achieved using any convenient protocol. In some instances, the sample includes cells which are maintained in a suitable culture medium, and the dye compound or dye conjugate is introduced into the culture medium. For in vivo protocols, any convenient administration protocol may be employed. Depending upon the target, the response desired, the manner of administration, e.g. i.v. s.c. i.p. oral, etc, the half-life, the number of cells present, various protocols may be employed. The term "sample" as used herein relates to a material or mixture of materials, typically, although not necessarily, in fluid form, containing one or more components of interest (e.g., an analyte).

In some embodiments, the subject method further includes separation or purification of the labeled analyte (e.g., analyte-detection reagent complex, or dye labeled analyte) from the sample. Any convenient methods maybe utilized in such a separation or purification step, including but not limited to, flow cytometry, scanning cytometry, gel electrophoresis, capillary electrophoresis, ion exchange chromatography, size exclusion chromatography, hydrophobic interaction chromatography, filtration, extraction, ELISA methods, and the like.

Assays in which one or more analytes of interest are labeled using analyte-specific detection reagents and subsequently optically analyzed are well known in the art, and the present fluorescent dye-conjugates are generally useful as detection reagents in such assays. For example, proteins in a sample can be labeled using a detection reagent consisting of a labeled protein, typically an antibody, which binds specifically to the analyte protein. Detection of the resulting labeled analyte proteins can be carried out using a number of well-known assay formats and instrumentation, including using flow cytometry, scanning cytometry, imaging, and gel analysis. Flow cytometry is described at length in the extensive literature in this field, including, for example, Landy et al. (eds.), Clinical Flow Cytometry, Annals of the New York Academy of Sciences Volume 677 (1993); Bauer et al. (eds), Clinical Flow Cytometry: Principles and Applications, Williams & Wilkins (1993); Ormerod (ed.), Flow Cytometry: A Practical Approach, Oxford Univ. Press (1997); Jaroszeski et al. (eds.), Flow Cytometry Protocols, Methods in Molecular Biology No. 91, Humana Press (1997); and Practical Shapiro, Flow Cytometry, 4th ed., Wiley-Liss (2003). Fluorescence imaging microscopy is described in, for example, Pawley (ed), Handbook of Biological Confocal Microscopy, 2nd Edition, Plenum Press (1989).

Illumination sources useful for exciting the fluorescent polymers of the invention include, but are not limited to, hand-held ultraviolet lamps, mercury arc lamps, xenon lamps, lasers and laser diodes. These illumination sources are optionally integrated into laser scanners, fluorescence microplate readers, standard or mini-fluorometers, or chromatographic detectors. In some instances, fluorescent polymers of the invention are excitable at or near 633 nm, and can be excited using a relatively inexpensive red laser excitation source.

Aspects of the invention include an analytical fluidic system that includes an instrument that contains a sample that includes a dye or a dye conjugate, e.g., as described herein. Any convenient instrument or apparatus that is suitable for use in the methods of the invention may be loaded with the sample. Instruments of interest include, but are not limited to flow cytometers, scanning cytometers, imagers, and gel analysis instruments. Any convenient sample, e.g., as described herein, may be loaded into the subject instruments, using any convenient method. The sample may include one or more components such as, an analyte of interest, a dye, or a dye-conjugate, such as a dye-antibody, a dye-oligonucleotide, or a microsphere coated with a dye-protein conjugate. In some instances, the instrument is a flow cytometer loaded with a sample that includes an analyte of interest and a dye-conjugate.

Utility

The dye compounds, conjugates thereof and methods of the invention, e.g., as described above, find use in a variety of applications. Applications of interest include, but are not limited to: research applications and diagnostic applications in a variety of fields including histology, cytology and immunology. Methods of the invention find use in a variety of different applications including any convenient application where detection and/or quantitation of an analyte of interest by fluorescence is of interest.

The subject dye compounds, conjugates and methods find use in a variety of diagnostic and research applications. Diagnostic applications of interest include, but are not limited to, diagnostic assays where identification and separation of subpopulations of cells in a mixture of cells by flow cytometry, diagnostic assays utilizing fluorescence-activated cell sorting and fluorescence microscopy, diagnostic assays involving the determination of the concentration of binding moieties (e.g., antigen-antibody binding), and the like. Such diagnostic assays may include detection of analytes in samples such as blood, urine and cerebrospinal fluid.

The subject dye compounds, conjugates and methods find use in a variety of research applications. Research applications of interest include, but are not limited to, detection of cell surface markers such as CD3, CD4, CD8, CD14, CD19, CD20, CD45, etc.

In one aspect of the invention, the reactive dyes are used to directly label a sample, or components of the sample, so that the sample can be identified or quantitated. Chemically reactive dye compounds covalently attach to a corresponding functional group on a wide variety of materials, forming dye conjugates, as described above.

In some embodiments, the reactive dye compounds are used to directly stain or label samples with biological components. The sample may comprise heterogeneous mixtures of components (including intact cells, cell extracts, bacteria, viruses, organelles, and mixtures thereof), or a single component or homogeneous group of components (e.g. natural or synthetic amino acid, nucleic acid or carbohydrate polymers, or lipid membrane complexes). These dyes are generally non-toxic to living cells and other biological components, within the concentrations of use.

For direct labeling, the dye compound is combined with the sample in any way that facilitates contact between the dye compound and the sample components of interest. In some instances, the dye compound or a solution containing the dye compound is simply added to the sample. Certain dyes of the invention, such as those that are substituted by one or more sulfonic acid moieties, tend to be impermeant to membranes of biological cells, and once inside viable cells are typically well retained. Treatments that permeabilize the plasma membranes, such as electroporation, shock treatments or high extracellular ATP can be used to introduce selected dye compounds into cells. Alternatively, selected dye compounds can be physically inserted into cells, e.g. by pressure microinjection, scrape loading, patch clamp methods, or phagocytosis.

Dyes that incorporate an aliphatic amine or a hydrazine residue can be microinjected into cells, where they can be fixed in place by aldehyde fixatives such as formaldehyde or glutaraldehyde. This fixability makes such dyes useful for intracellular applications such as neuronal tracing.

Dye compounds that possess a lipophilic substituent, such as phospholipids, will non-covalently incorporate into lipid assemblies, e.g. for use as probes for membrane structure; or for incorporation in liposomes, lipoproteins, films, plastics, lipophilic microspheres or similar materials; or for tracing. Lipophilic dyes are useful as fluorescent probes of membrane structure.

For direct staining of analytes in biological applications, the dye compounds of the invention may be used in an aqueous, mostly aqueous or aqueous-miscible solution prepared according to methods generally known in the art. The exact concentration of dye compound is dependent upon the experimental conditions and the desired results, but may range from about one nanomolar to one millimolar or more. The optimal concentration is determined by systematic variation until satisfactory results with minimal background fluorescence are accomplished.

In another aspect of the invention, the fluorescent dye-conjugates of the present invention are useful as, or as part of, detection reagents, such as analyte-specific detection reagents, to facilitate the optical detection and analysis of analytes. In one embodiment, the dye-conjugate substrate itself is an analyte-specific reagent, and the fluorescent dye-conjugate is used as a detection reagent to label an analyte of interest. In an alternative embodiment, the fluorescent dye-conjugate is bound to an analyte-specific reagent, and the combined entity is used as detection reagents to label an analyte of interest. In this alternative embodiment, the dye-conjugate acts as a fluorescent label bound to the analyte-specific reagent.

Assay and Test Kits of Dyes and Conjugates

Aspects of the invention further include kits, where the kits include one or more components employed in methods of the invention. Any of the components described herein may be provided in the kits, e.g., dye compounds, dye conjugates, substrates (e.g., antibody, biopolymer, polynucleotide), analytes, cells, supports (e.g., membranes, beads, particles, films, microspheres), specific binding moieties (e.g., as described in Table 2), buffers, reagents, conjugation reagents, light source, e.g., as described herein. A variety of components suitable for use in making and using conjugates may be included. Kits may also include tubes, buffers, etc., and instructions for use. The various reagent components of the kits may be present in separate containers, or some or all of them may be pre-combined into a reagent mixture in a single container, as desired. The kits optionally further comprise one or more buffering agents, typically present as an aqueous solution. The kits of the invention optionally further comprise additional detection reagents, a purification medium for purifying the resulting labeled substance, luminescence standards, enzymes, enzyme inhibitors, organic solvent, or instructions for carrying out an assay of the invention.

One aspect of the instant invention is the formulation of kits that facilitate the practice of various assays using any of the dyes of the invention, as described above. The kits of the invention may comprise a fluorescent dye of the invention, either present as a chemically reactive label useful for preparing dye-conjugates, or present as a dye-conjugate where the conjugated substance is a specific binding pair member, or a nucleoside, nucleotide, oligonucleotide, nucleic acid polymer, peptide, or protein. In some cases, the dye is present as a tandem conjugate (e.g., as described herein).

In some embodiments, the kit comprises a reactive dye compound having the structure of Formula I, Formula II, Formula III, Formula IV, Formula V, or Formula VI (e.g., as described above); and one or components selected from a dye conjugates, a substrate, an analyte, a cell, a support, a specific binding moiety, a buffer, a reagent, a light source and instructions for use of reactive dye compounds.

In certain embodiments, the kit comprises a dye conjugate having the structure of Formula VII, Formula VIII, Formula IX, Formula X, Formula XI, or Formula XII (e.g., as described above); and one or components selected from a dye compound, a substrate, an analyte, a cell, a support, a specific binding moiety, a buffer, a reagent, a light source and instructions for use of dye conjugates. In certain instances, the dye conjugate includes a dye-APC conjugate.

In certain cases, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another form of these instructions is a computer readable medium, e.g., diskette, compact disk (CD), Hard Drive etc., on which the information has been recorded. Yet another form of these instructions that may be present is a website address which may be used via the internet to access the information at a removed site.

The following examples are put forth so as to provide those of ordinary skill in the art with a complete disclosure and description of how to make and use the present invention, and are not intended to limit or define the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXAMPLES

Some synthetic strategies for dyes of interest, as well as their characterization, synthetic precursors, conjugates and methods of use are provided in the examples below. Further modifications and permutations will be evident to one skilled in the art.

Example 1

Preparation of Compound 2

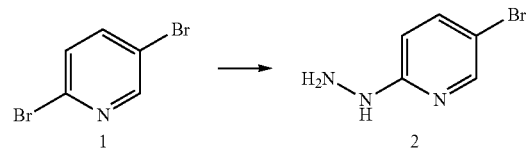 [SMILES: Brc1ccc(Br)nc1 ; NNc1ccc(Br)cn1]

To a solution of 2,5-dibromopyridine (10 g, 42 mmol) in 1-butanol (50 mL), hydrazine hydrate (80%, 13 mL, 211 mmol) is added at room temperature. After 6 hours at 115° C., the mixture is concentrated to around 15 mL. The white solid is formed and collected by filtration, washed by 30 mL cold water. After dried in the air overnight, Compound 2 (8.0 g) is obtained as an off-white solid.

Example 2

Preparation of Compound 3

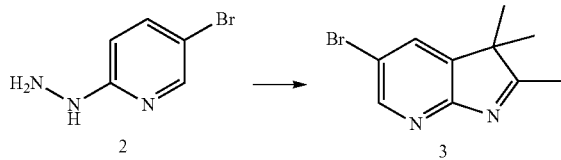

To a solution of Compound 2 (20 g, 106 mmol) in benzene (100 mL), 3-methyl-2-butanone (22.9 mL, 212 mmol) is added at room temperature. The mixture is refluxed overnight using a condenser equipped with a Dean-Stark trap. The mixture is concentrated and the residue is heated in polyphosphoric acid (125 g) at 140° C. for 45 min. The mixture is poured into ice water (500 M) with stirring. NaOH (5 N) is added to neutralize the solution to pH=8.0, and extracted with EtOAc (500 mL). After drying over $Na_2SO_4$, the residue is purified on silica column to give Compound 3 (7.6 g) as a yellow solid.

Example 3

Preparation of Compound 4

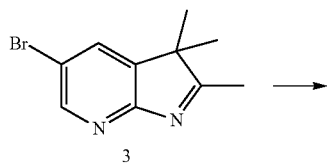

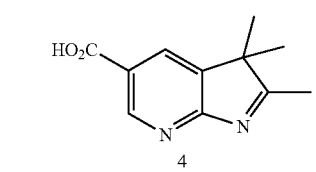

To a solution of Compound 3 (2 g, 8.36 mmol) in dry THF (40 mL) at −78° C., n-BuLi (2.5 M, 7.4 mL, 18.4 mmol) in hexanes is added dropwise. After 1 hour at −78° C., $CO_2$ gas is bubbled through the reaction mixture and kept bubbling at −78° C. for 1 hour. HCl solution (1 N, 50 mL) is added to quench the reaction, and the crude material is purified by HPLC to give Compound 4 (1 g) as a light brown solid.

Example 4

Preparation of Compound 5

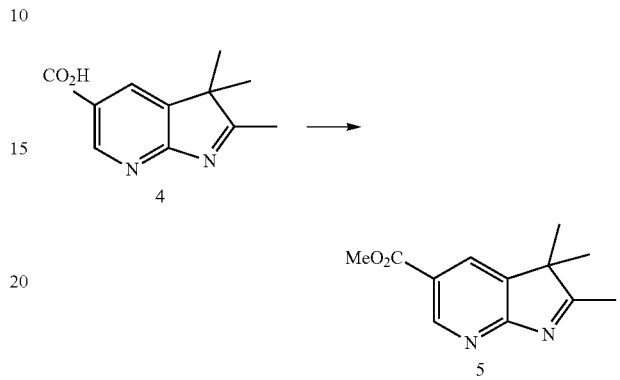

To a solution of Compound 4 (0.5 g, 2.5 mmol) in MeOH (10 mL), concentrated $H_2SO_4$ (few drops) is added and the mixture kept refluxing for 72 hours. NaOAc (1 g) is added and stirred for 30 min. The concentrated and the residue is dissolved in EtOAc (50 mL), washed with $H_2O$ (50 mL), brine (50 mL), dried over $Na_2SO_4$ and concentrated. The brown solid 5 (0.61 g) is used in the next step without further purification.

Example 5

Preparation of Compound 6

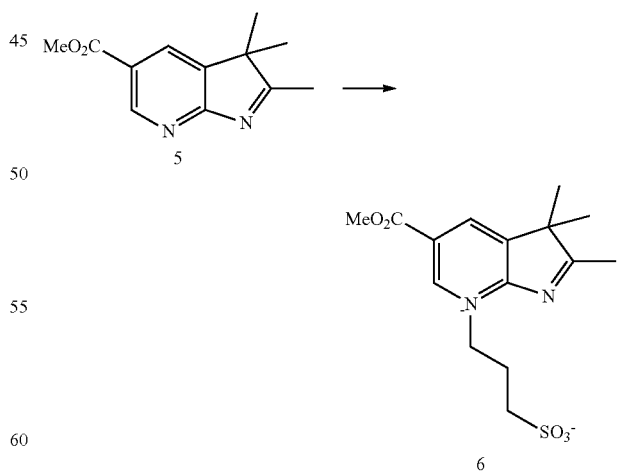

A mixture of Compound 5 (0.61 g, 2.8 mmol) and 1,3-propanesultone (2 g, 16.8 mmol) in 1,2-dichlorobenzene (6 mL) is heated at 65° C. for 3 hours. The mixture is added to ether (50 mL) and the precipitate is collected by filtration, to give compound 6 (0.8 g) as a brown solid. The brown solid Compound 6 is used in the next step without further purification.

Example 6

Preparation of Compound 7

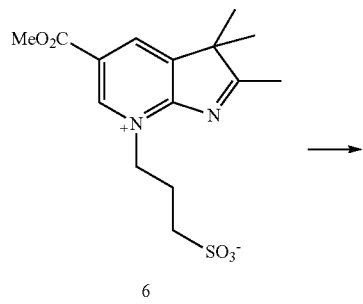
6

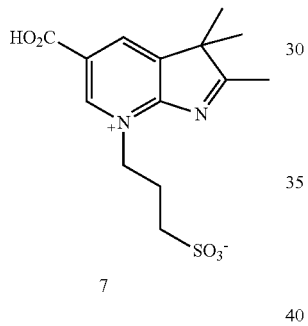
7

To a solution of Compound 6 (0.8 g, 2.4 mmol) in MeOH (15 mL) is dropwise added 1 N NaOH solution (5 mL) at room temperature. After 1 hour at room temperature, 1 N HCl (6 mL) is added to make pH=2.0. The mixture is purified by HPLC to give Compound 7 (0.52 g) as a light brown solid.

Example 7

Preparation of Compound 8

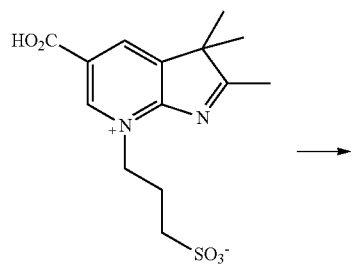
7

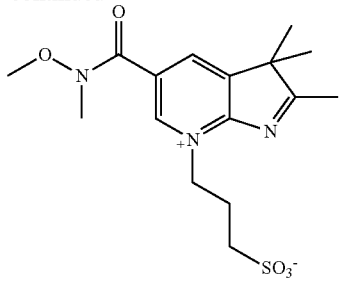
8

At 0° C., to a solution of Compound 7 (1.21 g, 2.75 mmol) in DMF (8 mL) and pyridine (4 mL), 1-ethyl-3-(3-dimethylaminopropyl)carbodiimide (0.633 g, 3.3 mmol) is added. After 15 min at 0° C., N,O-dimethylhydroxylamine hydrochloride (0.32 g, 3.3 mmol) is added. After 2 hours at room temperature, the mixture is added to diethyl ether (50 mL) and the precipitate is collected by filtration. The crude material is purified by HPLC to give Compound 8 (1.12 g) as a light brown solid.

Example 8

Preparation of Compound 10

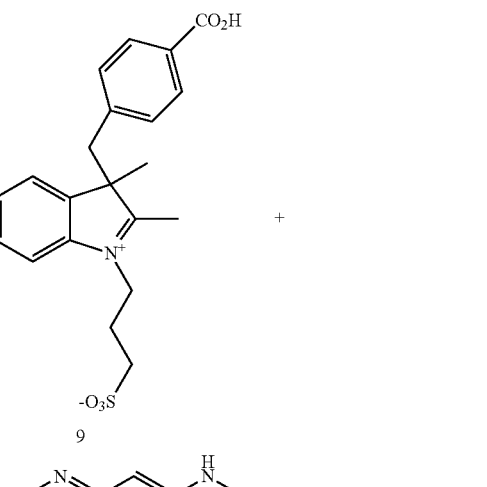
9

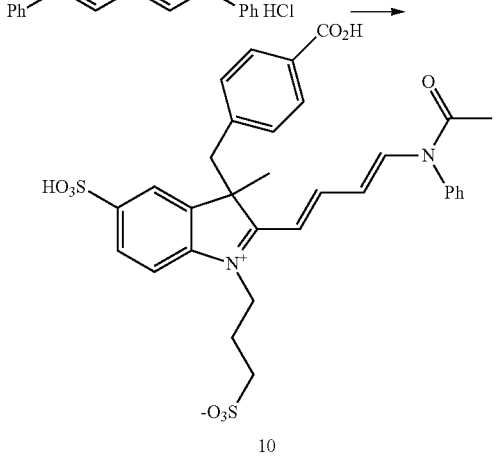
10

To the solution of Compound 9 (1.38 g, 2.32 mmol, Shaanxi Zhendi Chemical Biology Co., Ltd) in acetic anhydride (10 mL) and acetic acid (5 mL), malonaldehyde dianilide hydrochloride (0.69 g, 2.66 mmol) is added. After 30 minutes at 115° C., the mixture is added to EtOAc (50 mL), and the precipitate is collected by filtration, washed by EtOAc (50 mL). The red solid Compound 10 (1.51 g) is used in the next step without further purification.

Example 9

Preparation of Compound 11

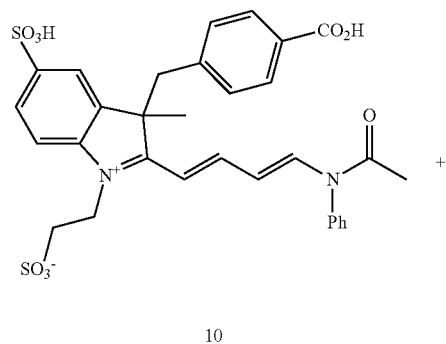

10

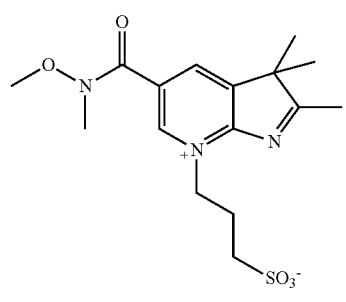

8

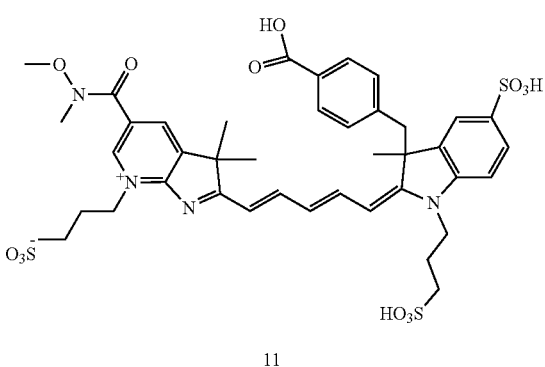

11

To the mixture of Compound 10 (1.51 g, 2.32 mmol) and Compound 8 (1.12 g, 2.32 mmol) in DMF (12 mL), acetic anhydride (1.05 mL, 11.1 mmol) is added, followed by triethylamine (2.58 mL, 18.6 mmol). After 12 hours at room temperature, the crude Compound 11 is precipitated in diethyl ether (200 ml), filtration and dried. The residue is dissolved in $H_2O$ (50 mL), and stirred at room temperature for 6 hours. The mixture is purified by HPLC to give Compound 11 (0.95 g) as a deep red solid.

Example 10

Preparation of Compound 12

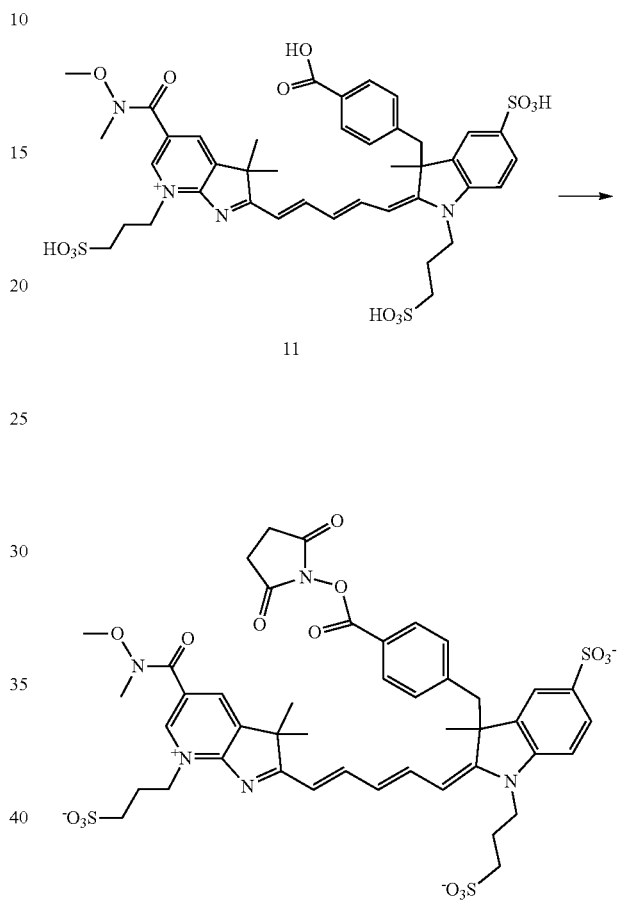

To the solution of Compound 11 (100 mg, 0.1 mmol) in DMF (4 mL) is added O—(N-succinimidyl)-N,N,N',N'-tetramethyluronium tetrafluoroborate (35 mg, 0.12 mmol), followed by triethylamine (0.3 mL). The mixture is stirred at room temperature for 1 hour. The solution is poured into EtOAc (15 mL). The solid is centrifuged and washed with EtOAc (3×10 mL), ether (1×10 mL) and dried under vacuum to give Compound 12 as a bright blue powder (110 mg).

Example 11

Preparation of Compound 14

The desired Indolium 14 is prepared from the reaction of potassium salt of 1,1,2-trimethylbenzindolenium-6,8-disulfonic acid (5.0 g, 0.011 mol) and 6-bromohexanoic acid (5.3 g, 0.027 mol) in dichlorobenzene at 120° C. overnight, followed by a work-up procedure as described in BIOCONJUGATE CHEM., 105-111 (1993) and 356-362 (1996).

Example 12

Preparation of Compound 15

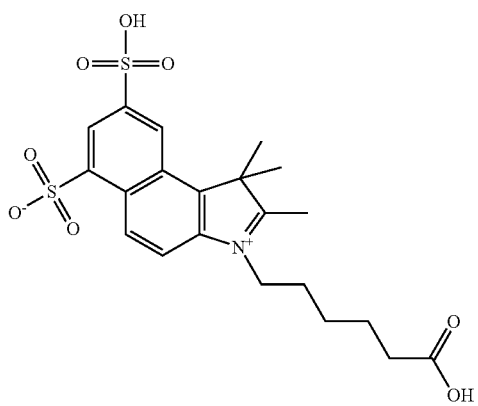

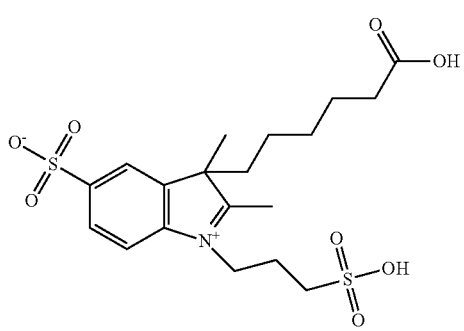

The Compound 15 is analogously synthesized from the Fisher reaction of 4-sulfophenylhydrazine with 7-methyl-8-oxo-nonanoic acid, followed by quaternization with 1,3-propanesultone utilizing a procedure as described in U.S. Pat. No. 7,465,810.

Example 13

Preparation of Compound 16

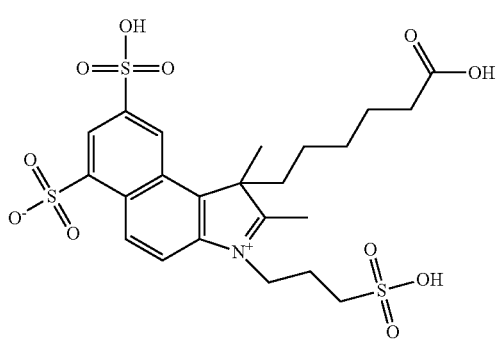

The Compound 16 is analogously synthesized from the reaction of 6-hydrazinonaphthalene 1,3-disulfonate with 7-methyl-8-oxo-nonanoic acid, followed by quaternization with 1,3-propanesultone utilizing a procedure as described in U.S. Pat. No. 7,465,810.

Example 14

Preparation of Compound 17

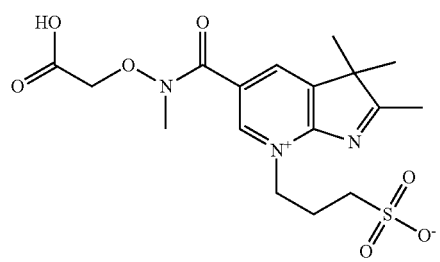

The Compound 17 is analogously synthesized from the reaction of Compound 6 with O-carboxymethylhydroxlamine according to the procedure of Compound 8.

Example 15

Preparation of Compound 18

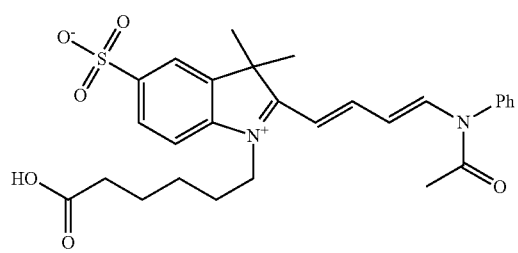

The desired Imine 18 is analogously prepared from the reaction of Compound 13 with malonaldehyde dianilide hydrochloride according to the procedure of Compound 10.

Example 16

Preparation of Compound 19

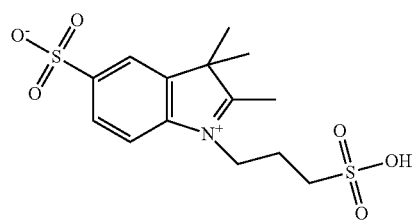

The desired Indolium 19 is prepared from the reaction of potassium salt of 1,1,2-trimethylindolenium-5-sulfonic acid and 1,3-propanesultone as described in BIOCONJUGATE CHEM. 105-111 (1993) and 356-362 (1996).

Example 17

Preparation of Compound 20

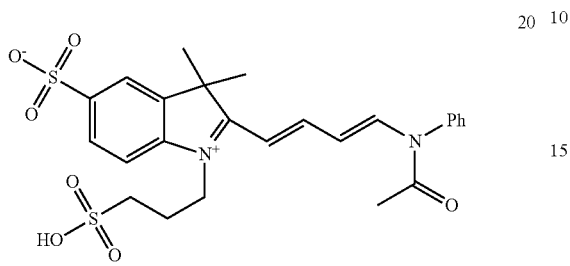

The desired Imine 20 is analogously prepared from the reaction of Compound 19 with malonaldehyde dianilide hydrochloride according to the procedure of Compound 10.

Example 18

Preparation of Compound 21

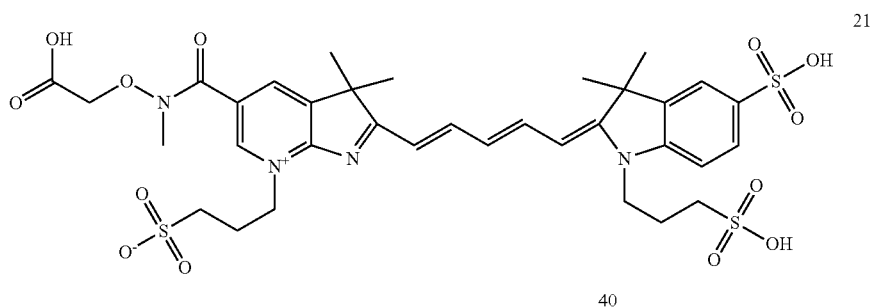

Cyanine 21 is analogously prepared from the condensation of Compound 20 with Compound 17 according to the procedure of Compound 11.

Example 19

Preparation of Compound 22

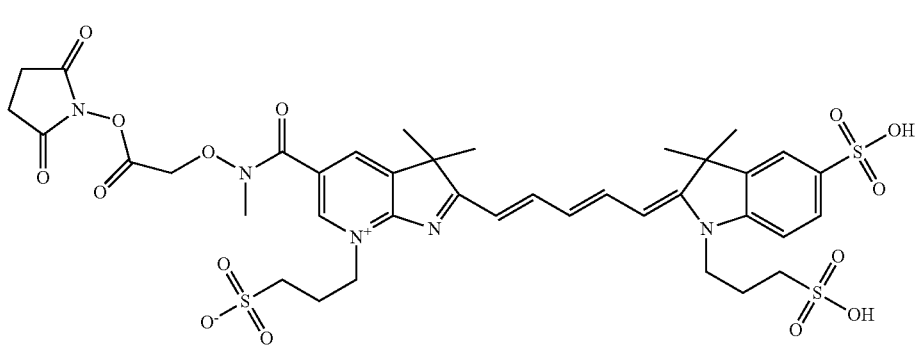

Cyanine 22 is prepared from Compound 21 according to the procedure of Compound 12.

Example 20
Preparation of Compound 23
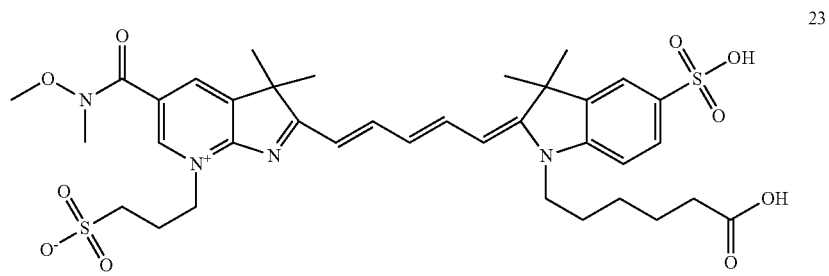 [SMILES: CON(C)C(=O)c1cc2c([n+](CCCS(=O)(=O)[O-])c1)N=C(/C=C/C=C/C=C1/N(CCCCCC(=O)O)c3ccc(S(=O)(=O)O)cc3C1(C)C)C2(C)C]
Cyanine 23 is analogously prepared from the condensation of Compound 18 with Compound 8 according to the procedure of Compound 11.
Example 21
Preparation of Compound 24
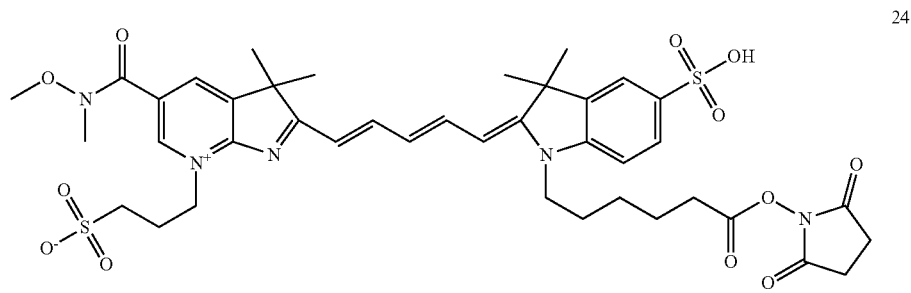 [SMILES: CON(C)C(=O)c1cc2c([n+](CCCS(=O)(=O)[O-])c1)N=C(/C=C/C=C/C=C1/N(CCCCCC(=O)ON3C(=O)CCC3=O)c3ccc(S(=O)(=O)O)cc3C1(C)C)C2(C)C]
Cyanine 24 is analogously prepared from Compound 23 according to the procedure of Compound 12.
Example 22
Preparation of Compound 25
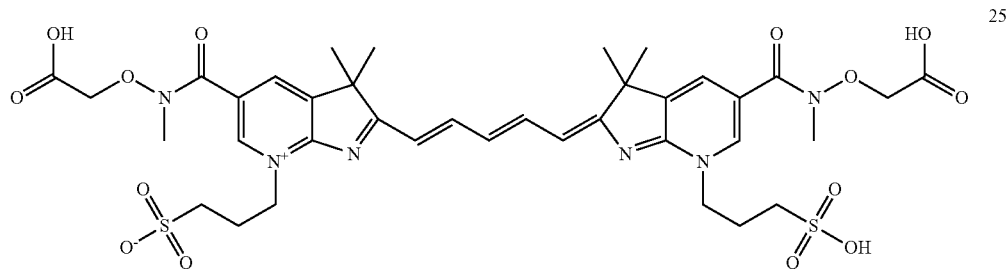 [SMILES: CN(OCC(=O)O)C(=O)C1=CN(CCCS(=O)(=O)O)C2=N/C(=C/C=C/C=C/C3=Nc4c(cc(C(=O)N(C)OCC(=O)O)c[n+]4CCCS(=O)(=O)[O-])C3(C)C)C(C)(C)C2=C1]

A solution of Compound 17 (100 mg, 0.25 mmol) and malonaldehyde bis(phenylimine) monohydrochloride (27 mg, 0.1 mmol) in acetic acid (0.5 mL) and acetic anhydride (0.5 mL) is heated at 120° C. for 1 hour, followed by adding NaOAc (50 mg). The completion of the reaction is monitored by absorption spectra in methanol. The reaction mixture is heated until the anyl intermediate disappears (monitored by absorption spectra). The reaction mixture is cooled and poured into ethyl acetate (50 mL).

The crude product is collected by centrifugation and washed with ethyl acetate twice. Preparative HPLC purification gives Compound 25 as a bright blue powder (90 mg).

Example 23

Preparation of Compound 26

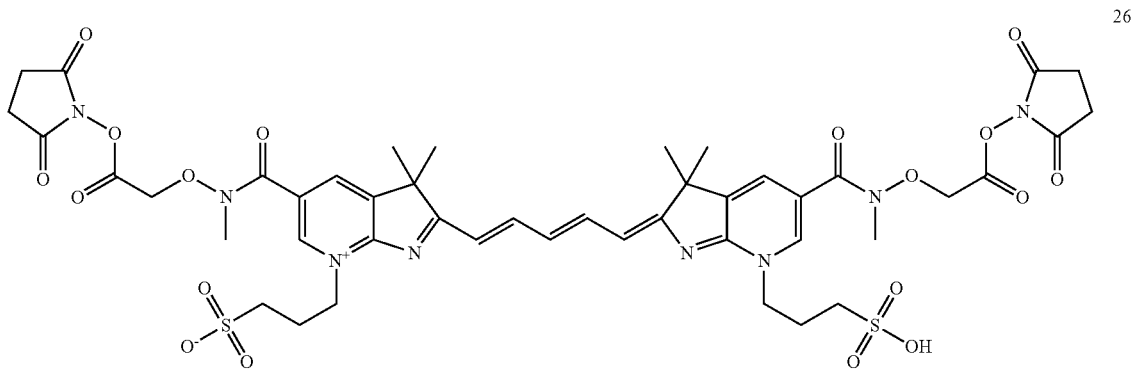 [SMILES: CN(OCC(=O)ON1C(=O)CCC1=O)C(=O)C1=CN(CCCS(=O)(=O)O)C2=N/C(=C/C=C/C=C/C3=Nc4c(cc(C(=O)N(C)OCC(=O)ON5C(=O)CCC5=O)c[n+]4CCCS(=O)(=O)[O-])C3(C)C)C(C)(C)C2=C1]

Cyanine 26 is analogously prepared from Compound 25 according to the procedure of Compound 12.

Example 24

Preparation of Compound 27

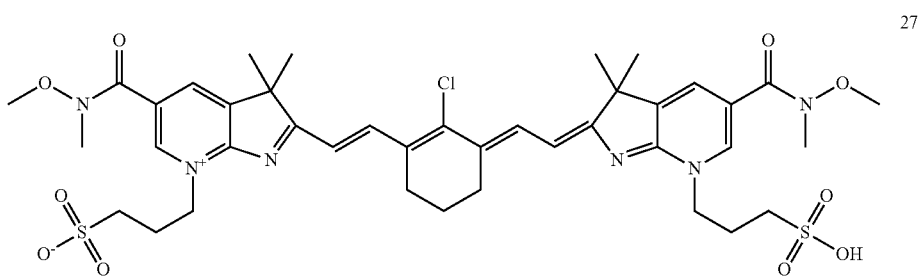

A solution of Compound 8 (370 mg, 1 mmol) and 2-chloro-1-formyl-3-(hydroxymethylene)cyclohex-1-ene (70 mg, 0.4 mmol) in 1-butanol (48 mL) and benzene (12 mL) is heated to reflux for 2 hours. To the reaction mixture is added 1-butanol (7 mL) and benzene (3 mL). The mixture is continued to reflux for 10 hours with removal of water by a Dean-Stark condenser. After removal of solvent, the residue is purified by preparative HPLC to give Compound 27.

Example 25
Preparation of Compound 28
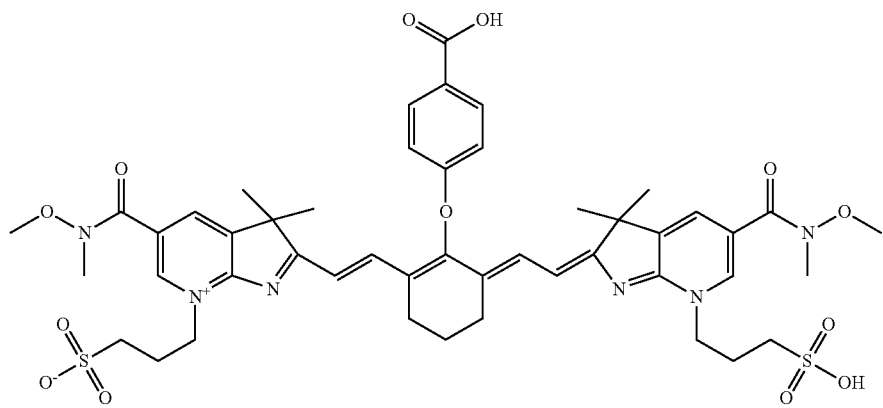
Compound 27 (90 mg) is converted to Compound 28 by 4-hydroxybenoic acid and sodium hydride in DMF according to the procedure of N. Narayanan and G. Patonary (J. ORG. CHEM., 60, 2391 (1995)). Preparative HPLC purification gives pure Compound 28 (80 mg).
Example 26
Preparation of Compound 29
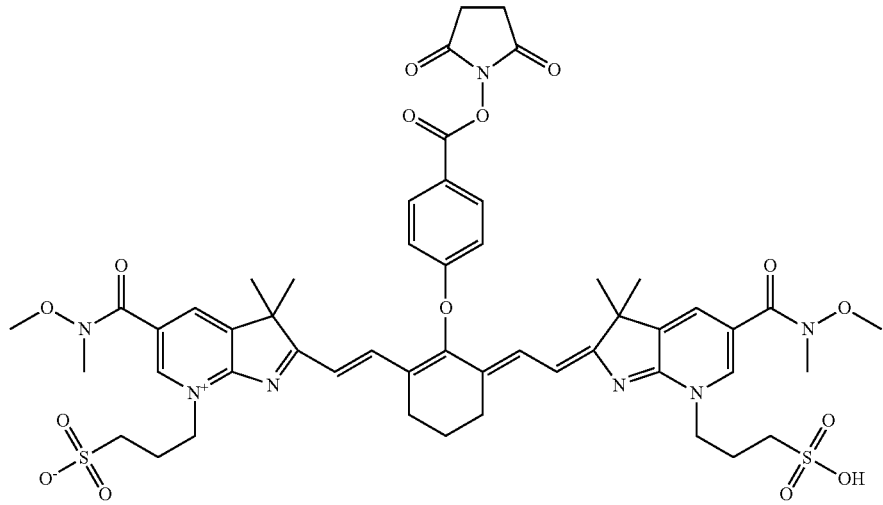

Cyanine 29 is analogously prepared from Compound 28 according to the procedure of Compound 12.

Example 27

Preparation of Compound 31

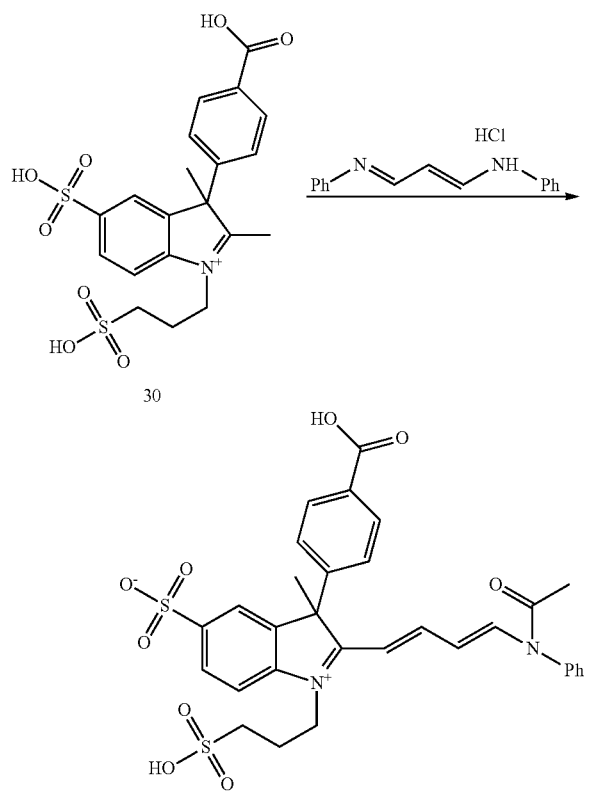

Immine 31 is analogously prepared from Compound 30 (Shaanxi Zhendi Chemical Biology Co., Ltd) according to the procedure of Compound 10.

Example 28

Preparation of Compound 32

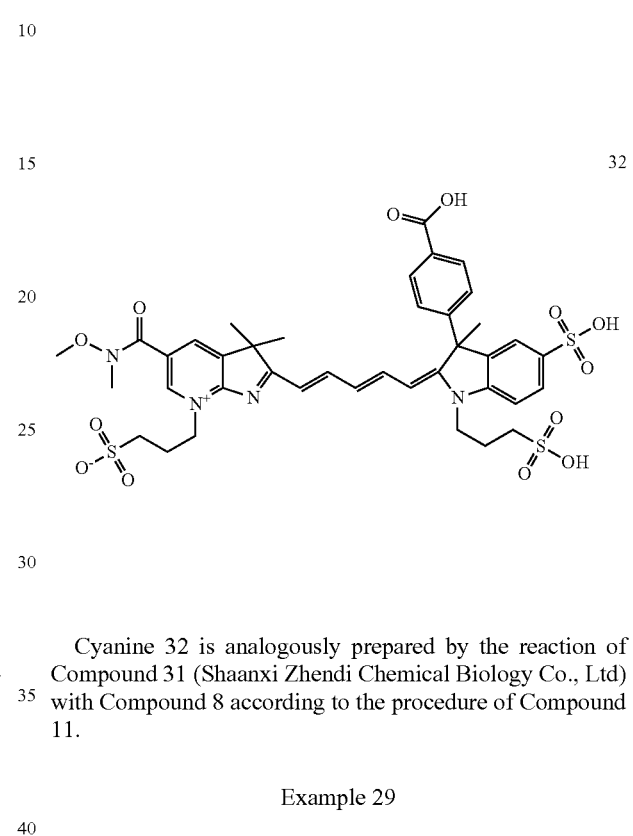

Cyanine 32 is analogously prepared by the reaction of Compound 31 (Shaanxi Zhendi Chemical Biology Co., Ltd) with Compound 8 according to the procedure of Compound 11.

Example 29

Preparation of Compound 33

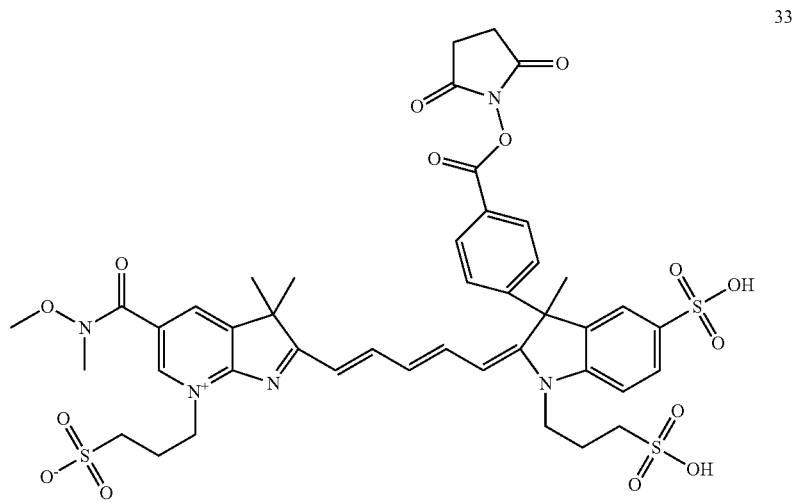 [SMILES: CON(C)C(=O)c1cc2c([n+](CCCS(=O)(=O)[O-])c1)N=C(/C=C/C=C/C=C1/N(CCCS(=O)(=O)O)c3ccc(S(=O)(=O)O)cc3C1(C)c1ccc(C(=O)ON3C(=O)CCC3=O)cc1)C2(C)C]

Cyanine 32 is analogously converted to its active ester 33 according to the procedure of Compound 12.

Example 30

Preparation of Compound 34

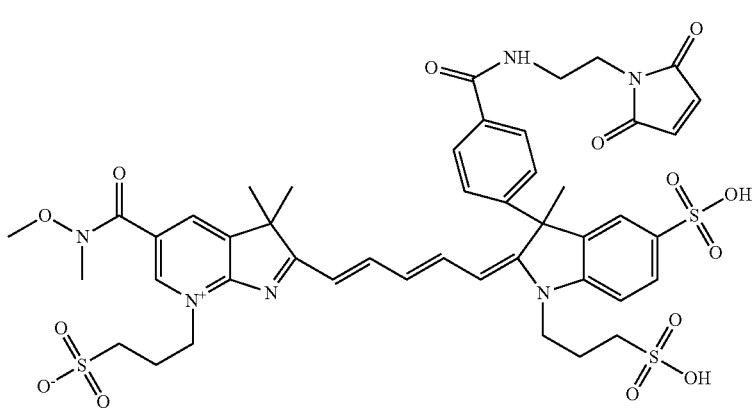

To Compound 33 (10 mg) in DMF (0.2 ml) at room temperature is added 4 equivalents of triethylamine and 1.2 equivalents of N-(2-aminoethyl)maleimide, trifluoroacetic acid salt (Sigma-Aldrich). The mixture is stirred at ambient temperature for 60 minutes. The DMF solution is poured into ether, and resulted suspension is centrifuged to collect the solid that is air-dried. The crude product is further purified with silica gel chromatography to yield the desired Compound 34.

Example 31

Preparation of Compound 35

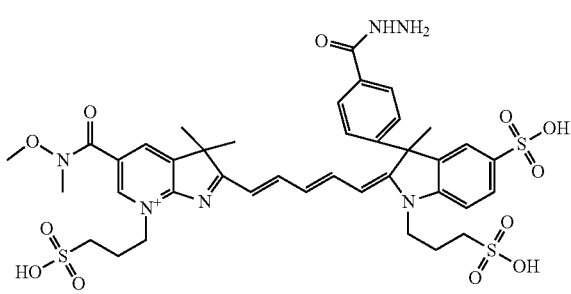

To hydrazine (100 mg in 1 ml water) is added Compound 33 (50 mg) in DMF (0.2 ml) at room temperature. The mixture is stirred at ambient temperature for 60 minutes. The DMF solution is poured into water, and resulted suspension is centrifuged to collect the solid that is air-dried. The crude product is further purified by HPLC to yield the desired Compound 35.

Example 32

Preparation of Protein-Dye Conjugates

Protein-dye conjugates can be prepared using any convenient method, such as those described in, for example, Haugland et al. 1995, Meth. Mol. Biol. 45:205; Haugland, 1995, Meth. Mol. Biol. 45:223; Haugland, 1995, Meth. Mol. Biol. 45:235; Haugland, 2000, Current Protocols in Cell Biology 16.5.1-16.5.22. For example, protein-dye conjugates can be prepared using a subject succinimidyl ester, as follows.

A solution of the protein is prepared at about 10 mg/mL in 0.1 M sodium bicarbonate. The labeling reagents are dissolved in a suitable solvent such as water, or DMF or DMSO at about 10 mg/mL. Predetermined amounts of the labeling reagents are added to the protein solutions with stirring. The reaction mixture is incubated at room temperature for one hour or on ice for several hours. The dye-protein conjugate is typically separated from free unreacted reagent by size-exclusion chromatography, such as on Amersham PD-10 resin (GE Healthcare Bio-Sciences Corp., Piscataway, N.J.) equilibrated with phosphate-buffered saline (PBS). The initial, protein-containing colored band is collected and the degree of substitution is determined from the absorbance at the absorbance maximum of each fluorophore, using the extinction coefficient of the free fluorophore. The dye-protein conjugate thus obtained is optionally subfractionated to yield conjugates with higher, lower or more uniform DOS.

For many applications, such as for producing dye-labeled antibodies, a molar ratio of 10 to 50 equivalents of dye to 1 equivalent of protein is used. It will be understood that optimal reaction conditions and reactant concentrations may be determined empirically. Optimization of dye-protein conjugation is well known in the art, and described in, for example, the references cited herein.

Example 33

Preparation of Antibody-Dye Conjugates

Dye-conjugates of an IgG antibody. Dye-conjugates of Compounds 12, 22, 26, 29, 40, 48, 49 and 50 were prepared using the following general protocol, with minor variations, as noted below.

Step 1. Prepare Protein Solution:

Mix 50 µL of 1 M NaHCO$_3$ with 450 µL of IgG protein solution (4 mg/mL) to obtain a 0.5 mL protein sample solution (Solution A). The resulting solution should have a pH 8.5±0.5.

Step 2. Prepare Dye Solution:
  To 50 μL of DMSO, add 1 mg of the dye compound, and stir until the compound is completely dissolved to obtain a dye solution (Solution B).
Step 3. Carry Out Conjugation Reaction:
  Add the protein solution (A) to the dye solution (B) with effective stirring or shaking, and keep the reaction mixture stirred or shaken for 1-3 hrs to obtain the protein-dye conjugate.
Step 4. Purify the Conjugate:
  a) Load a PD-10 column (Amersham Biosciences, Piscataway, N.J.) with the protein-dye conjugate reaction mixture (from step 3, filtrated if necessary) or supernatant as soon as the liquid in the pre-packed column runs just below the top surface;
  b) Add 1 mL of a 1×PBS elution buffer as soon as the sample runs just below the top resin surface; Repeat this 'sample washing' process twice; Add more 1× elution buffer solution to elute the desired sample;
  c) Collect the faster-running band that is usually the desired labeled protein. Keep the slower-running band that is usually free or hydrolyzed dye until the desired product is identified.
Step 5. Characterizing the Desired Dye-Protein Conjugate:
  a) Measure OD (absorbance) at the maximum absorption wavelength of protein, which is 280 nm, and at the maximum absorption wavelength of the dye. For most spectrophotometers, the samples (from the column fractions) need be diluted with de-ionized water so that the OD values are in the range from 0.1 to 0.9. The maximum absorption wavelength of the Compound 12 amide is about 683 nm. For use with other dye compounds, the maximum absorption wavelength of the dye should be measured prior to the conjugations.
  b) Calculate the degree of substitution (DOS) using the following equation for Compound 12:

$$\text{DOS}=[\text{dye}]/[\text{protein}]=A_{683}\times\epsilon_p/250000(A_{280}-0.035 A_{683})$$

where [dye] is the dye concentration and [protein] is the protein concentration. The dye concentration can be readily calculated from the Beer-Lambert Law: $A=\epsilon_{dye} C \times L$, wherein A is the absorbance, $\epsilon_{dye}$ is the molar extinction coefficient, C is the concentration, and L is the length of the light path through the solution. The protein concentration can be either estimated by the weight (added to the reaction), if the conjugation efficiency is high enough (preferably >70%), or, more accurately, calculated by the Beer-Lambert Law: $A=\epsilon_{protein} C \times L$. For example, IgG has an $\epsilon$ value of 203,000 $cm^{-1}M^{-1}$. It should be noted that to obtain accurate DOS, the conjugate should be free of the non-conjugated dye.

For effective labeling, the degree of substitution should fall between 3-20 moles of Compound 12 to one mole of antibody for most antibodies. The DOS that provides optimal labeling will depend on the antibody, and in some cases, a higher DOS may provide improved labeling. The optimal labeling is determined empirically by preparing dye-conjugates over a range of DOS and comparing the measured fluorescence intensities. Examples are shown in the figures.

Example 34

Preparation of Dye-Conjugates of Periodate-Oxidized Glycoproteins

Samples of 5 mg of goat IgG antibody (which has a polysaccharide chain attached to the protein) in 1 mL of 0.1 M sodium acetate, 0.135 M NaCl, pH 5.5, are treated with 2.1 mg of sodium metaperiodate on ice for a period of time experimentally determined to be sufficient to result in the desired amount of aldehyde groups on the glycoprotein, which are then reacted with Compound 35. The reactions are stopped by addition of 30 μL ethylene glycol. The antibodies are purified on a Sephadex G25 column packed in PBS pH 7.2. One-tenth volume of 1 M sodium bicarbonate is added to raise the pH and Compound 35 is added at a molar ratio of dye to protein of 50:1. The reaction is stirred at room temperature for a period of time experimentally determined to be sufficient to result in the desired dye/protein ratio. Sodium cyanoborohydride is added to a final concentration of 10 mM and the reaction is stirred for 4 hours at room temperature. The antibody conjugates are purified by dialysis and on Sephadex G25 columns as described herein. Periodate-oxidized glycoproteins in gels and on blots can also be labeled, by adapting methods as described in Estep and Miller, 1986, Anal. Biochem. 157:100-105, the disclosure of which is incorporated herein by reference.

Example 35

Preparation of a Protein-Dye Conjugate Using a Thiol-Reactive Dye

A solution of beta-galactosidase, a protein rich in free thiol groups, is prepared in PBS (2.0 mg in 400 μL). The protein solution is then treated with a 10 mg/L solution of the maleimide derivative Compound 34 in DMF. Unreacted dye is removed on a spin column. The degree of substitution by the dye is estimated using the extinction coefficient of the free dye, as described in Example 33. The protein concentration is estimated from the absorbance at 280 nm, corrected for the absorbance of Compound 34 at that wavelength.

Example 36

Preparation of Aminodextran-Dye Conjugates

Aminodextran-dye conjugates are prepared as follows, described using 70,000 MW aminodextran (50 mg) derivatized with an average of 13 amino groups as an example. The aminodextran (50 mg) is dissolved at 10 mg/mL in 0.1 M NaHCO₃. Compound 12, 22, 26, 29, 40, 48, 49 or 50 is added so as to give a dye/dextran ratio of about 10-15. After 6-12 hours, the resulting conjugate is purified on SEPHADEX G-50 and eluted with water. In some cases, 6-10 moles of dye are conjugated to 70,000 MW dextran.

Example 37

Preparation of Dye-labeled Microspheres

Microspheres can be labeled with a subject dye using any convenient protocols. Microspheres chemically modified to have functional groups such as amino, carboxyl, or aldehydes on the surface can be surface-labeled by covalently conjugating the surface groups with a corresponding reactive dyes, as listed in Table 1. For example, amine-modified microspheres are readily conjugated to the dyes of the invention through succinimidyl esters, such as Compound 12, 22, 26, 29, 40, 48, 49 or 50.

A dye-labeled protein, prepared as described above, can be covalently coupled through its amine residues to carboxylate groups on a microsphere using ethyl 3-(dimethylaminopropyl)carbodiimide (EDAC). Alternatively, the dye-labeled protein can be passively adsorbed on the microspheres. For example, carboxylate-modified microspheres are suspended in a solution dye-labeled protein, the protein is allowed to passively adsorb on the microspheres, and excess protein is removed by centrifugation and washing. Microparticles of a size that cannot be centrifuged are separated from excess protein by dialysis through a semi-permeable membrane with a high MW cutoff or by gel filtration chromatography. Biotinylated microspheres can be treated with a streptavidin, avidin or anti-biotin conjugated to a subject dye, as described above.

Example 38

Preparation of Nucleotide-dye Conjugates

Nucleotides conjugated with the subject dyes can be readily prepared using any convenient procedures, such as those described in M. Nimmakayalu et al., 2000, Biotechniques 28, 518-522; Muhlegger et al., 1990, Biol Chem Hoppe Seyler 371, 953-965; and Giaid et al., 1989, Histochemistry 93, 191-196, the disclosures of which are incorporated herein by reference. Examples of particular conjugations are described, below.

To 2 mg of 5-(3-aminoallyl)-2'-deoxyuridine 5'-triphosphate (Sigma-Aldrich) in 100 µl water is added Compound 12, 22, 26, 29, 40, 48, 49 or 50 in 100 µL DMF and 5 µL triethylamine. After 3 hours, the solution is evaporated and the residue is purified by HPLC. The product fractions are lyophilized to give fluorescent nucleotide conjugate.

Alternatively, fluorescent dye-conjugates of deoxyuridine 5'-triphosphate are prepared from 5-(3-amino-1-propynyl)-2'-deoxyuridine 5'-triphosphate, or by treating a thiolated nucleotide or a thiophosphate nucleotide with a thiol-reactive dye of the invention (such as the maleimide Compound 34).

Alternatively, 2'-(or 3')-2-aminoethylaminocarbonyladenosine 5'-triphosphate is reacted with a slight excess of Compound 12, 22, 26, 29, 40, 48, 49 or 50, following precipitation with ethanol, the ribose-modified product is purified by preparative HPLC.

Example 39

Preparation of Oligonucleotide-Dye Conjugates

A 5'-amine-modified, 18-base M13 primer sequence (about 100 µg) is dissolved in 4 µl water. To this is added 250 µg of Compound 12, 22, 26, 29, 40, 48, 49 or 50 in 100 µl 0.1 M sodium borate, pH 8.5. After 16 hours, 10l of 5 M NaCl and 3 volumes of cold ethanol are added. The mixture is cooled to ~20° C., centrifuged, the supernatant is decanted, the pellet is rinsed with ethanol, and the pellet is then dissolved in 100 µL water. The labeled oligonucleotide is purified by HPLC. The desired peak is collected and evaporated to give the fluorescent oligonucleotide-dye conjugate.

Example 40

Cell Analysis by Flow Cytometry Using Dye-Antibody Conjugates

Analyte-specific antibodies conjugated to a subject dye compound (i.e, labeled antibodies) are useful for the analysis of blood cells (for example, in whole blood samples) by flow cytometry. The labeled-antibodies may be used to label (stain) cellular proteins, and the labeled cells detected using a flow cytometer.

Samples (100 µL) of whole blood (preferably collected in EDTA) are stained with antibody-dye conjugate for 30-60 minutes in the dark at a dye-conjugate concentration of 1 µg or less per 0.1 ml of blood. Following staining, 2 mL of 1×FACS™ Lysing Solution (BD Bioscience, San Jose, Calif.) are added to the sample, the sample is mixed at medium speed on a vortex mixer and then incubated at room temperature for 10 min. The sample is centrifuged at 200-500 g (preferably 200-300) for 5 minutes and the supernatant is decanted. The sample is washed (resuspended in 2 mL of 0.5% BSA/PBS wash buffer, mixed, and centrifuged) twice, re-suspended in either 0.5 mL of wash buffer or 150 µl of Fixation Stabilization Buffer, and held at 4° C. until flow cytometric analysis.

Analysis of the stained cells is carried out using a BD Canto II flow cytometer (BD Biosciences, San Jose, Calif.) equipped with a red (~640 nm) laser. Fluorescent biopolymers incorporating dye compounds such as Compounds 12 and 48 to APC exhibit an excitation maximum closely matching the 640 nm emission of the red laser, and the emission from the biopolymers is measured in the 710/20 nm detection channel. The flow cytometer is setup following the manufacturer's instructions. Flow cytometric analysis of the sample of stained cells is carried out according to the manufacturer's protocols, and the data is analyzed using standard techniques well known in the field to obtain the median fluorescence intensity for the cell population of interest.

It will be understood that the particular antibody conjugate used and the specific reaction components and particular reaction conditions used can have an effect on the results obtained. Routine experimentation can be carried out to determine preferred reaction components, such as buffers or lyse solutions, and reaction conditions, including staining times and temperatures. Such routine optimization of assay conditions is standard practice in the field of immunostaining-based assays.

Example 41

Dye-Conjugates of Anti-CD8, CD19 and CD20 Antibodies

Dye-conjugates were prepared using antibodies specific to CD8 and CD20 (BD Biosciences, San Jose, Calif.), each conjugated, in separate preparations, to Compounds 12 and 48 over a range of dye-to-protein ratios. The cell staining was prepared essentially as described in example 40, above. The antibody-conjugates of the CD8, CD19 and CD20 antibodies were used to analyze lymphocytes in whole blood samples, essentially as described in example 40, above.

The data indicated an optimal dye-to-protein ratio for each antibody-dye pair. For each antibody, the optimal dye-to-protein ratio for each of the three dyes occurred at similar ratios. Comparing the different antibodies conjugated to the same dyes, the optimal dye-to-protein ratios were significantly different. Comparing the maximum fluorescence staining obtained using each dye compound, Compounds 12 and 48 yielded better fluorescence staining than did the spectrally similar Alexa Fluor® 700 as seen in FIG. 8 (CD8).

Figure 8:
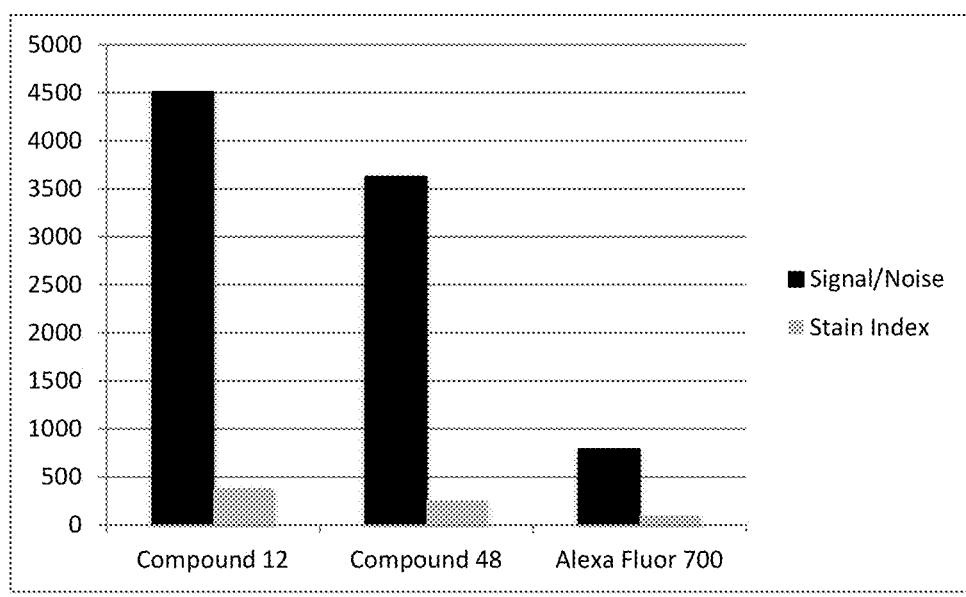
FIG. 8 shows immuno staining data obtained using dye-antibody conjugates of CD8 antibody with Compounds 12 and 48, respectively, in comparison to CD8-Alexa Fluor® 700 conjugate.

FIG. 8. The dye-antibody conjugates of CD8 labeled with Compounds 12 and 48 are observed to provide the adequate labeling of lymphocyte populations for use in flow cytometric immunofluorescence assays, which is superior to the labelings resulted from the spectrally equivalent Alexa Fluor® 700.

The results indicate that all dye-conjugates of the invention are useful in preparing antigen-specific detection reagents for immunofluorescence assays analyzed by flow cytometry. In general, the optimal dye-to-protein ratio is determined empirically for each antibody to be labeled.

Figure 9:
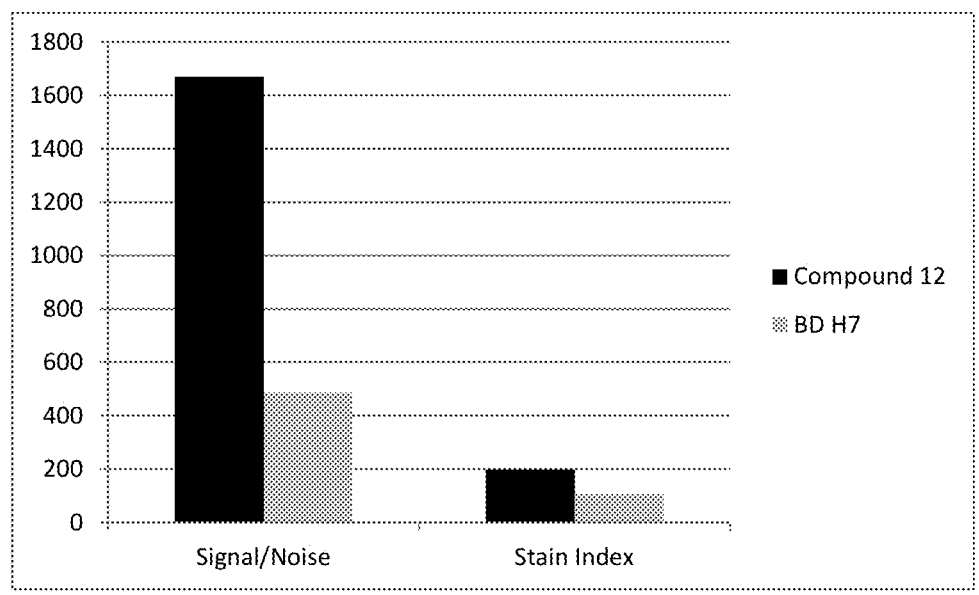
FIG. 9 shows immuno staining data obtained using a dye-antibody conjugate of CD20 antibody with Compound 12 in comparison to APC-H7.

FIG. 9. The dye-antibody conjugate of CD20 labeled with Compound 12 is observed to provide the adequate labeling of lymphocyte populations for use in flow cytometric immunofluorescence assays, which is superior to the labelings resulted from the spectrally equivalent APC-H7.

Example 42

Dye Tandem-Conjugates of Anti-CD8 and Anti-CD19 Antibodies

Dye-APC tandem-conjugates were prepared using antibodies specific to CD 8 (clone SKI from BD Biosciences, San Jose, Calif.), to Compound 12 essentially as described in the literature (U.S. Pat. No. 5,055,556 to Stryer et al.; and Clin. Chem. 2004, 50: 1921-1929). The antibody conjugate of the CD8 antibody were used to analyze lymphocytes in whole blood samples, essentially as described in example 40, above.

Figure 10:
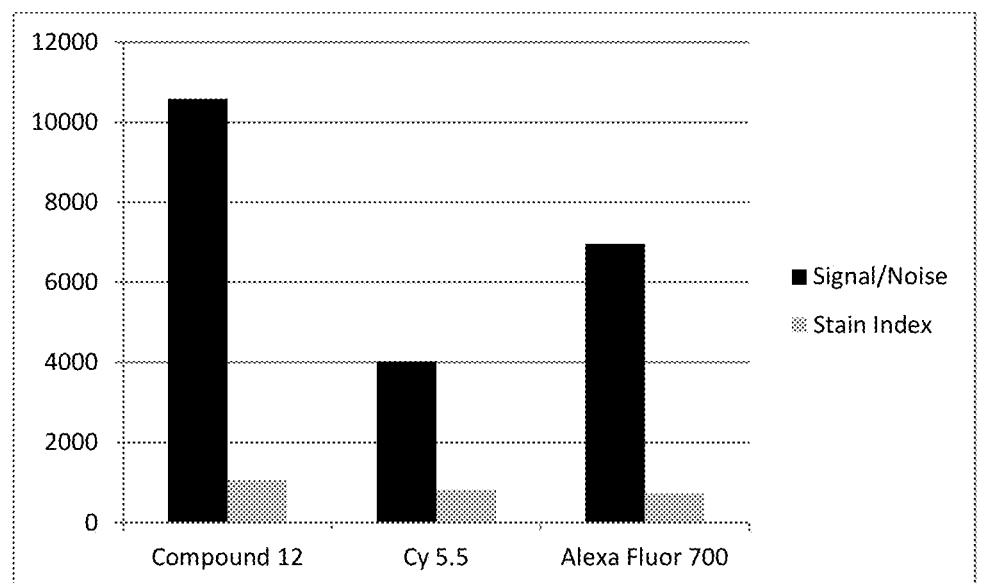
FIG. 10 shows immuno staining data obtained using tandem dye-antibody conjugates of CD8 antibody labeled with APC-Compound 12 in comparison to APC-Cy5.5 and APC-Alexa Fluor® 700.

Comparing the maximum fluorescence staining obtained using each dye conjugate, APC-Compounds 12 tandem conjugate yielded better fluorescence staining than did the spectrally similar Alexa Fluor® 700 as seen in FIGS. 10 (CD8) and 11 (CD19).

The tandem dye-antibody conjugate of CD8 labeled with APC-Compound 12 is observed to provide the adequate labeling of lymphocyte populations for use in flow cytometric immunofluorescence assays, which is superior to the labelings resulted from the spectrally equivalent APC-Alexa Fluor® 700 and APC-Cy5.5 (see FIG. 10).

Figure 11:
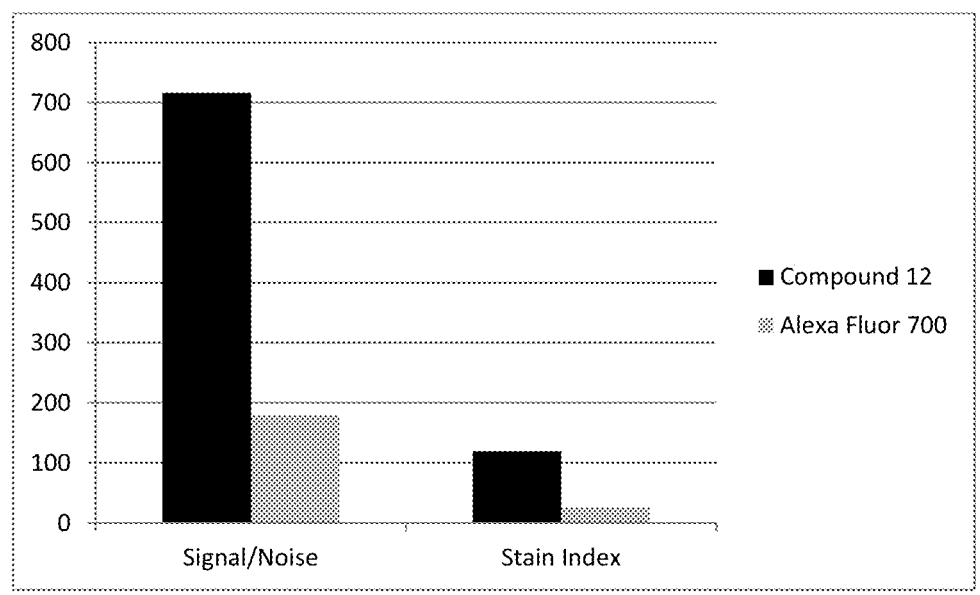
FIG. 11 shows immuno staining data obtained using a dye-antibody conjugate of CD19 antibody labeled with APC-Compound 12 tandem in comparison to CD19 antibody labeled Alexa Fluor®.
Figure 12:
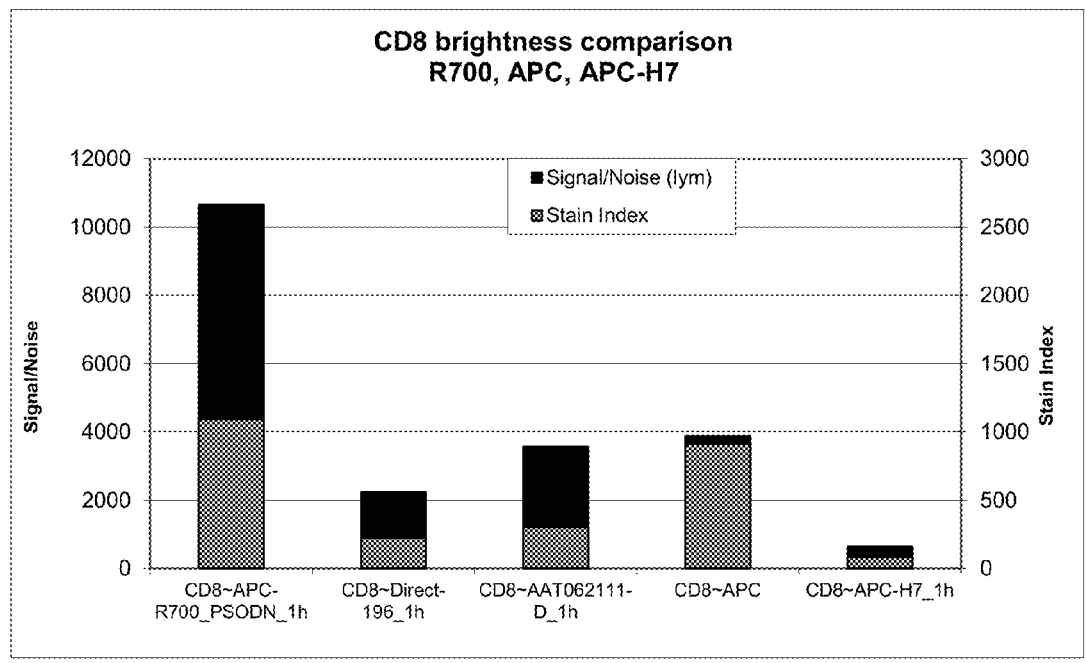
FIG. 12 shows a brightness comparison of Compound 12 (R700) tandem and direct CD8 conjugates versus APC and APC-H7 conjugates. APC-R700 tandem conjugate is brighter than both R700 direct conjugates and legacy dye conjugates.
Figure 12:
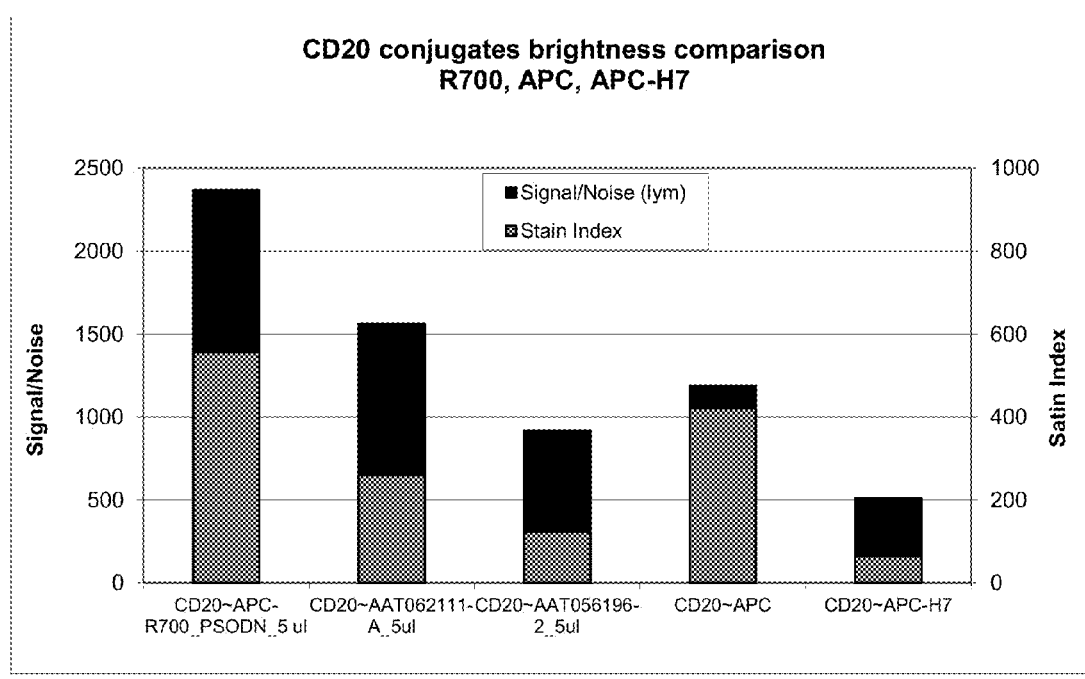
Figure 13:
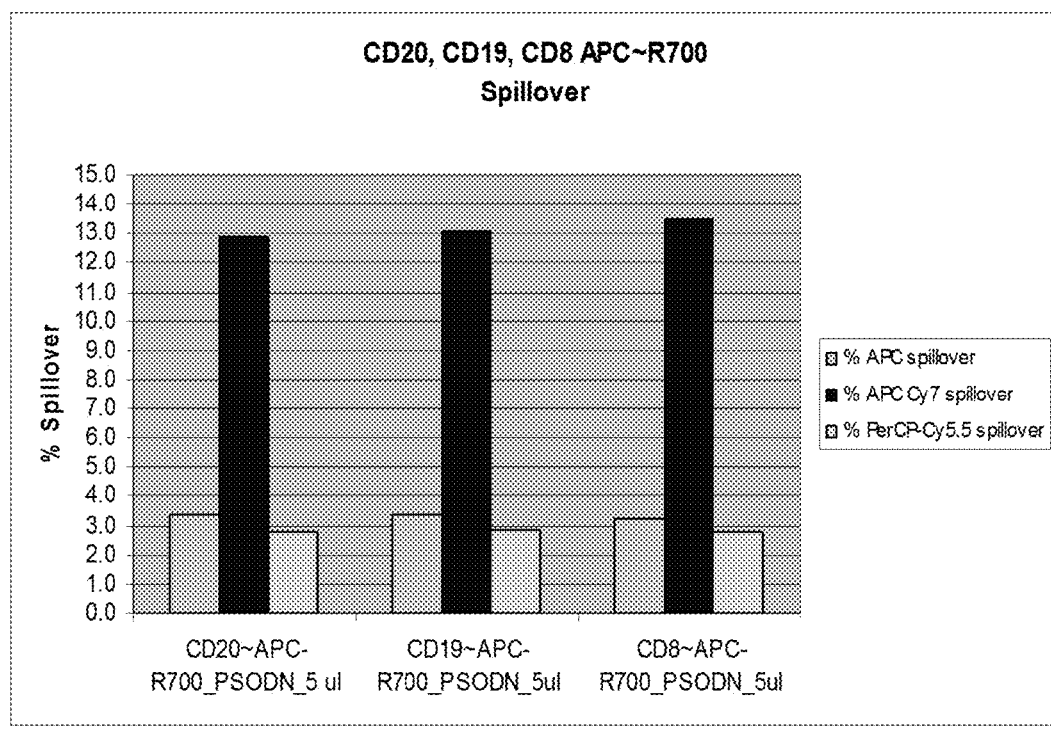
FIG. 13 shows that tandem conjugate of Compounds 12 (R700) has less % spillover into APC and APC-Cy7, and PerCP-Cy5.5 conjugates than an Alexa 700 dye.

The dye-antibody conjugate of CD19 labeled with Compound 12 tandem is observed to provide the adequate labeling of lymphocyte populations for use in flow cytometric immunofluorescence assays, which is superior to the labelings resulted from the CD19 antibody labeled Alexa Fluor® 700 (See FIG. 11).

Example 43

The Photostability Test

Figure 3:
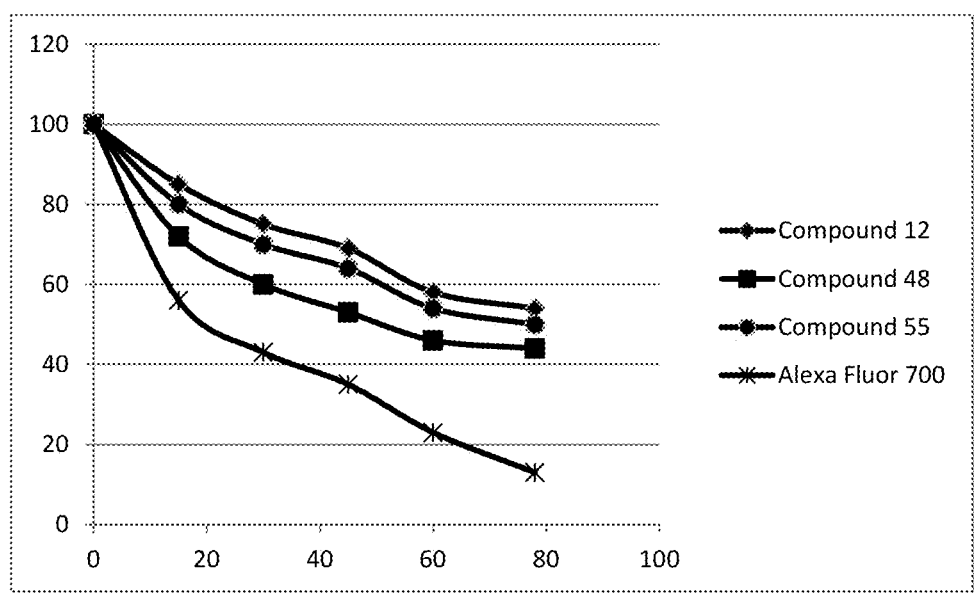
FIG. 3 illustrates a photostability comparison of Compounds 12, 48 and 55 with the Alexa Fluor® 700 NHS ester in PBS buffer (pH 7.4) (Example 43).
Figure 4:
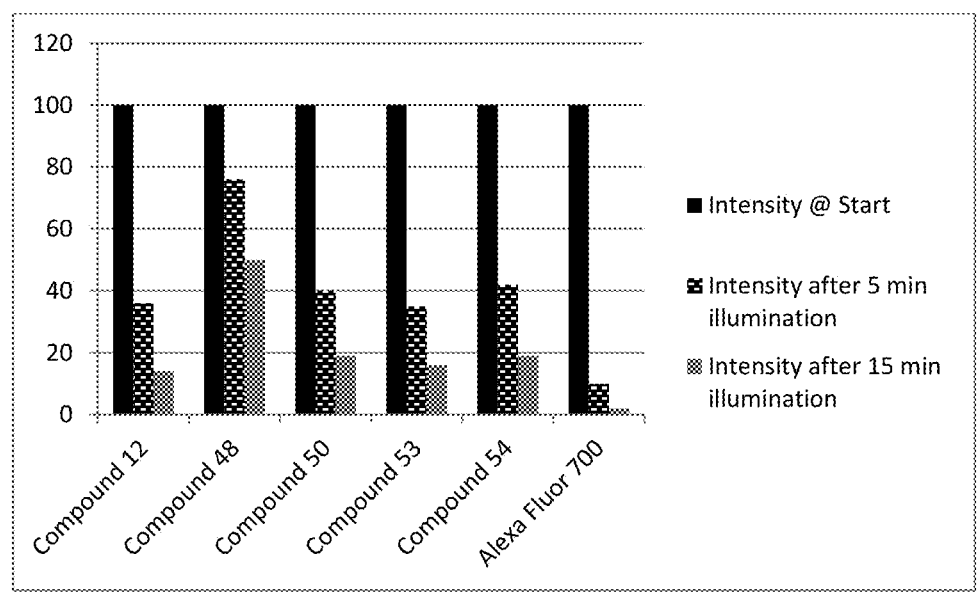
FIG. 4 illustrates a photostability comparison of APC-Compound 12, 48, 50, 53 and 54 tandems with the APC-Alexa Fluor® 700 tandem in PBS buffer (pH 7.4) (Example 43).

Photobleaching experiments are performed at 1 μM concentrations of Compound 12, 48 and 55, and commercially available Alexa Fluor 700. Both of the compounds are irridated with A100 W Mercury lamp in PBS (pH 7.0), where all of the dyes receive the same amount of irradiation as determined by photometric measurements. As shown in FIG. 3, Compound 12, 48 and 55 of the invention exhibit much higher photostability (much slower photobleaching rate) than the Alexa Fluor 700. Their APC tandems (prepared as described in U.S. Pat. No. 5,055,556 to Stryer et al.; and Clin. Chem. 2004, 50: 1921-1929) are also tested for photostability. As shown in FIG. 4, The APC tandem of Compound 12, 48, 50, 53 and 54 of the invention exhibit much higher photostability (much slower photobleaching rate) than that of the spectrally similar Alexa Fluor 700.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A 5-hydroxamate substituted azaindoline-cyanine dye compound, consisting of a 5-hydroxamate-azaindoline group linked to a 5-membered heterocyclic ring via a divalent polymethine linking group, wherein one or more of the 5-hydroxamate-azaindoline group, the divalent polymethine linking group and the 5-membered heterocyclic ring is substituted with a reactive group moiety (RGM).

2. The compound according to claim 1, wherein the compound has an absorbance maximum that is 600nm or greater.

3. The compound according to claim 1, wherein the compound has an emission maximum that is 700nm or greater.

4. The compound according to claim 1, wherein the compound is photostable.

5. The compound according to claim 1, wherein the compound is described by Formula I:

Formula I

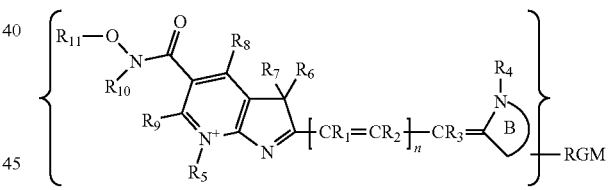

wherein:
ring B represents the atoms necessary to form a nitrogen-containing five-membered heterocyclic ring and further comprises zero to three fused aromatic rings; wherein each atom of the five-membered heterocyclic ring and the zero to three fused aromatic rings is independently selected from the group consisting of C, CH, C(alkyl), C(aryl), O, S, N, N(aryl) and N(alkyl), and the five-membered heterocyclic ring and the zero to three aromatic rings are optionally substituted with one or more substituents selected from the group consisting of a hydrogen, an alkyl having 1-20 carbons, a hydroxy, an alkoxy having 1-20 carbons, a trifluoromethyl, a halogen, a methylthio, a carbonyl, an amino, a thiol, a sulfonate, a phosphonyl, and a L-RGM;

n is 1 to 3;

$R_1$-$R_3$ are each independently a hydrogen, a halogen, an alkyl having 1-20 carbons, a cycloalkyl having 3-20 carbons, an aryl, a heteroaryl, an amino, an alkylamino, an arylamino, a thiol, an alkythiol, an arylthiol, a heteroarylthiol, a polyethyleneglycol, an alkoxy, an aryloxy, a carboxyalkyl, a phosphonylalkyl, a sulfonylalkyl, or a L-RGM;

$R_4$ and $R_5$ are each independently an alkyl having 1-20 carbons, a cycloalkyl having 3-20 carbons, an arylalkyl, a heteroarylalkyl, a carboxyalkyl, a phosphonylalkyl, a sulfoalkyl, or a L-RGM;

$R_6$ and $R_7$ are each independently an alkyl having 1-20 carbons, a cycloalkyl having 3-20 carbons, an aryl, an arylalkyl, a heteroaryl, a heteroarylalkyl, a carboxyalkyl, a carboxylaryl, a phosphonylalkyl, a sulfoalkyl, or a L-RGM;

$R_8$ and $R_9$ are each independently a hydrogen, an alkyl having 1-20 carbons, a hydroxy, an alkoxy having 1-20 carbons, a trifluoromethyl, a halogen, a methylthio, a carbonyl, an amino, a thiol, a sulfonate, a phosphonyl or a L-RGM;

$R_{10}$ and $R_{11}$ are each independently a hydrogen, an alkyl, an aryl, an arylalkyl, a heteroaryl, a heteroarylalkyl, a carboxyalkyl, a phosphonylalkyl, a sulfoalkyl, or a L-RGM;

RGM is a chemically reactive group; and

L is a linker.

6. The compound according to claim 5, wherein the compound is described by Formula II:

$R_4$ and $R_5$ are each independently an alkyl having 1-20 carbons, an arylalkyl, a carboxyalkyl, a phosphonylalkyl, a sulfoalkyl, or a L-RGM;

$R_6$, $R_7$, $R_{15}$ and $R_{16}$ are each independently an alkyl having 1-20 carbons, a cycloalkyl having 3-20 carbons, an aryl, an arylalkyl, a heteroaryl, a heteroarylalkyl, a carboxyalkyl, a carboxylaryl, a sulfoalkyl, or a L-RGM;

$R_8$, $R_9$ and $R_{17}$-$R_{20}$ are each independently a hydrogen, an alkyl having 1-20 carbons, a hydroxy, an alkoxy having 1-20 carbons, a trifluoromethyl, a halogen, a methylthio, a carbonyl, an amino, a thiol, a sulfonate, a phosphonyl, or a L-RGM;

$R_{10}$ and $R_{11}$ are each independently a hydrogen, an alkyl, an aryl, an arylalkyl, a heteroaryl, a heteroarylalkyl, a carboxyalkyl, a phosphonylalkyl, a sulfoalkyl, or a L-RGM;

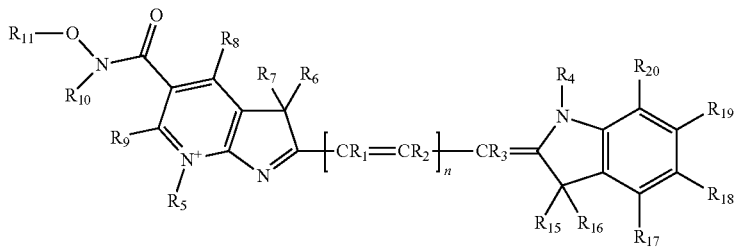

Formula II wherein:

n is 1 to 3;

$R_1$-$R_3$ are each independently a hydrogen, a halogen, an alkyl having 1-20 carbons, a cycloalkyl having 3-20 carbons, an aryl, a heteroaryl, an amino, an alkylamino, an arylamino, a thiol, an alkythiol, an arylthiol, a heteroarylthiol, a polyethyleneglycol, an alkoxy, an aryloxy, a carboxyalkyl, a phosphonylalkyl, a sulfonylalkyl, or a L-RGM;

RGM is a chemically reactive group;

L is a linker; and optionally, one or more of $R_4$ and $R_5$, $R_6$ and $R_7$, $R_5$ and $R_9$, $R_{15}$ and $R_{16}$, $R_4$ and $R_{20}$, $R_4$ and $R_6/R_7$, or $R_6/R_7$ and $R_{15}/R_{16}$ is taken in combination to form a 5- to 50-membered ring.

7. The compound according to claim 5, wherein the compound is described by Formula III:

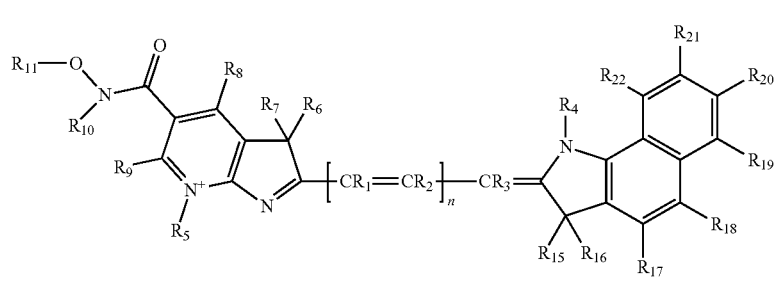

Formula III wherein:

n is 1 to 3;

$R_1$-$R_3$ are each independently a hydrogen, a halogen, an alkyl having 1-20 carbons, a cycloalkyl having 3-20 carbons, an aryl, a heteroaryl, an amino, an alkylamino, an arylamino, a thiol, an alkythiol, an arylthiol, a heteroarylthiol, a polyethyleneglycol, an alkoxy, an aryloxy, a carboxyalkyl, a phosphonylalkyl, a sulfonaylalkyl, or a L-RGM;

$R_4$ and $R_5$ are each independently an alkyl having 1-20 carbons, a cycloalkyl having 3-20 carbons, an arylalkyl, a heteroarylalkyl, a carboxyalkyl, a phosphonylalkyl, a sulfonylalkyl, or a L-RGM;

$R_6$, $R_7$, $R_{15}$ and $R_{16}$ are each independently an alkyl having 1-20 carbons, a cycloalkyl having 3-20 carbons, an aryl, an arylalkyl, a heteroaryl, a heteroarylalkyl, a carboxyalkyl, a carboxyaryl, a phosphonylalkyl, a sulfonylalkyl, or a L-RGM;

$R_8$, $R_9$ and $R_{17}$-$R_{22}$ are each independently a hydrogen, an alkyl having 1-20 carbons, a hydroxy, an alkoxy having 1-20 carbons, a trifluoromethyl, a halogen, a methylthio, a carbonyl, an amino, a thiol, a sulfonate, a phosphonyl, or a L-RGM; $R_{10}$ and $R_{11}$ are a hydrogen, an alkyl, an aryl, an arylalkyl, a heteroaryl, a heteroarylalkyl, a carboxyalkyl, a sulfoalkyl, or a L-RGM;

RGM is a chemically reactive group;

L is a linker; and optionally, one or more of $R_4$ and $R_5$, $R_6$ and $R_7$, $R_5$ and $R_9$, $R_{15}$ and $R_{16}$, $R_4$ and $R_{22}$, $R_4$ and $R_6/R_7$, or $R_6/R_7$ and $R_{15}/R_{16}$ is taken in combination to form a 5- to 50-membered ring.

8. The compound according to claim 5, wherein the compound is described by Formula IV:

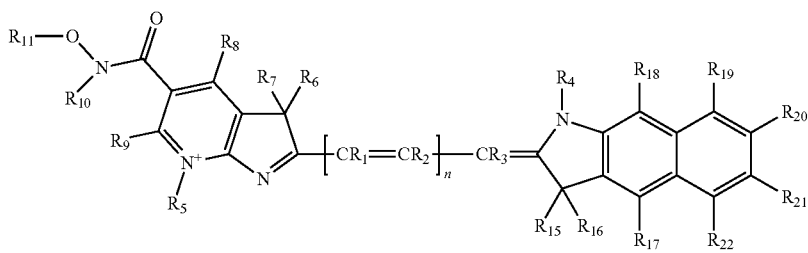

Formula IV wherein:

n is 1 to 3;

$R_1$-$R_3$ are each independently a hydrogen, a halogen, an alkyl having 1-20 carbons, a cycloalkyl having 3-20 carbons, an aryl, a heteroaryl, an amino, an alkylamino, an arylamino, a thiol, an alkythiol, an arylthiol, a heteroarylthiol, a polyethyleneglycol, an alkoxy, an aryloxy, a carboxyalkyl, a phosphonylalkyl, sulfonylalkyl, or a L-RGM;

$R_4$ and $R_5$ are each independently an alkyl having 1-20 carbons, a cycloalkyl having 3-20 carbons, an arylalkyl, a heteroarylalkyl, a carboxyalkyl, a sulfoalkyl, a phosphonylalkyl, or a L-RGM;

$R_6$, $R_7$, $R_{15}$ and $R_{16}$ are each independently an alkyl having 1-20 carbons, a cycloalkyl having 3-20 carbons, an aryl, an arylalkyl, a heteroaryl, a heteroarylalkyl, a carboxyalkyl, carboxylaryl, a phosphonylalkyl, a sulfoalkyl, or a L-RGM;

$R_8$, $R_9$ and $R_{17}$-$R_{22}$ are each independently a hydrogen, an alkyl having 1-20 carbons, a hydroxy, an alkoxy having 1-20 carbons, a trifluoromethyl, a halogen, a methylthio, a carbonyl, an amino, a thiol, a sulfonate, a phosphonyl, or a L-RGM; $R_{10}$ and $R_{11}$ are a hydrogen, an alkyl, an aryl, an arylalkyl, a heteroaryl, a heteroarylalkyl, a carboxyalkyl, a phosphonylalkyl, a sulfoalkyl, or a L-RGM;

RGM is a chemically reactive group;

L is a linker; and optionally, one or more of $R_4$ and $R_5$, $R_6$ and $R_7$, $R_5$ and $R_9$, $R_{15}$ and $R_{16}$, $R_4$ and $R_{18}$, $R_4$ and $R_6/R_7$, or $R_6/R_7$ and $R_{15}/R_{16}$ is taken in combination to form a 5- to 50-membered ring.

9. The compound according to claim 5, wherein the compound is described by Formula V:

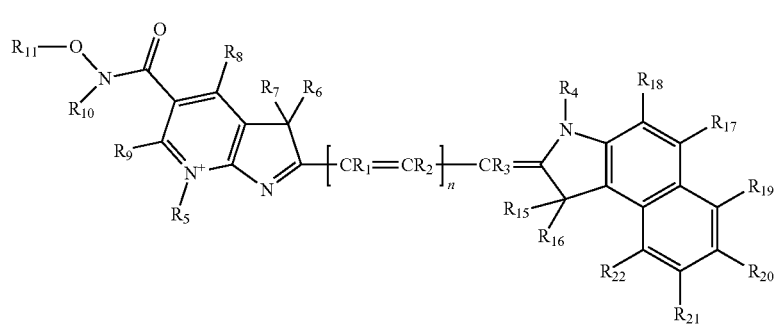

Formula V wherein:

n is 1 to 3;

$R_1$-$R_3$ are each independently a hydrogen, a halogen, an alkyl having 1-20 carbons, a cycloalkyl having 3-20 carbons, an aryl, a heteroaryl, an amino, an alkylamino, an arylamino, a thiol, an alkythiol, an arylthiol, a heteroarylthiol, a polyethyleneglycol, an alkoxy, an aryloxy, a carboxyalkyl, a phosphonylalkyl, a sulfonylalkyl, or a L-RGM;

$R_4$ and $R_5$ are each independently an alkyl having 1-20 carbons, a cycloalkyl having 3-20 carbons, an arylalkyl, a heteroarylalkyl, a carboxyalkyl, a phosphonylalkyl, a sulfonylalkyl, or a L-RGM;

$R_6$, $R_7$, $R_{15}$ and $R_{16}$ are each independently an alkyl having 1-20 carbons, a cycloalkyl having 3-20 carbons, an aryl, an arylalkyl, a heteroaryl, a heteroarylalkyl, a carboxyalkyl, carboxylaryl, a phosphonylalkyl, a sulfoalkyl, or a L-RGM;

$R_8$, $R_9$ and $R_{17}$-$R_{22}$ are each independently a hydrogen, an alkyl having 1-20 carbons, a hydroxy, an alkoxy having 1-20 carbons, a trifluoromethyl, a halogen, a methylthio, a carbonyl, an amino, a thiol, a sulfonate, a phosphonyl, or a L-RGM;

$R_{10}$ and $R_{11}$ are each independently a hydrogen, an alkyl, an aryl, an arylalkyl, a heteroaryl, a heteroarylalkyl, a carboxyalkyl, a sulfoalkyl, a phosphonylalkyl, or a L-RGM;

RGM is a chemically reactive group;
L is a linker; and optionally, one or more of $R_6$ and $R_7$, $R_5$ and $R_9$, $R_{15}$ and $R_{16}$, $R_4$ and $R_{18}$, $R_4$ and $R_6/R_7$, or $R_6/R_7$ and $R_{15}/R_{16}$ is taken in combination to form a 5- to 50-membered ring.

10. The compound according to claim 5, wherein the compound is described by Formula VI:

wherein:

n is 1 to 3;

$R_1$-$R_3$ are each independently a hydrogen, a halogen, an alkyl having 1-20 carbons, a cycloalkyl having 3-20 carbons, an aryl, a heteroaryl, an amino, an alkylamino, an arylamino, a thiol, an alkythiol, an arylthiol, a heteroarylthiol, a polyethyleneglycol, an alkoxy, an aryloxy, a carboxyalkyl, or a L-RGM;

$R_4$ and $R_5$ are each independently an alkyl having 1-20 carbons, a cycloalkyl having 3-20 carbons, an arylalkyl, a heteroarylalkyl, a carboxyalkyl, a sulfoalkyl, or a L-RGM;

$R_6$, $R_7$, $R_{15}$ and $R_{16}$ are each independently an alkyl having 1-20 carbons, a cycloalkyl having 3-20 carbons, an aryl, an arylalkyl, a heteroaryl, a heteroarylalkyl, a carboxyalkyl, a carboxylaryl, a sulfoalkyl, or a L-RGM;

$R_8$, $R_9$, $R_{17}$ and $R_{18}$ are each independently a hydrogen, an alkyl having 1-20 carbons, a hydroxy, an alkoxy having 1-20 carbons, a trifluoromethyl, a halogen, a methylthio, a carbonyl, an amino, a thiol, a sulfonate, a phosphonyl, or a L-RGM;

$R_{10}$, $R_{11}$, $R_{20}$ and $R_{21}$ are each independently a hydrogen, an alkyl, an aryl, an arylalkyl, a heteroaryl, a heteroarylalkyl, a carboxyalkyl, a sulfoalkyl, or a L-RGM;

RGM is a chemically reactive group;

L is a linker; and optionally, one or more of $R_4$ and $R_5$, $R_6$ and $R_7$, $R_5$ and $R_9$, $R_{15}$ and $R_{16}$, $R_4$ and $R_{18}$, $R_4$ and $R_6/R_7$, or $R_6/R_7$ and $R_{15}/R_{16}$ is taken in combination to form a 5- to 50-membered ring.

11. The compound according to claim 5, wherein the compound is described by one of the following structures:

Formula VI

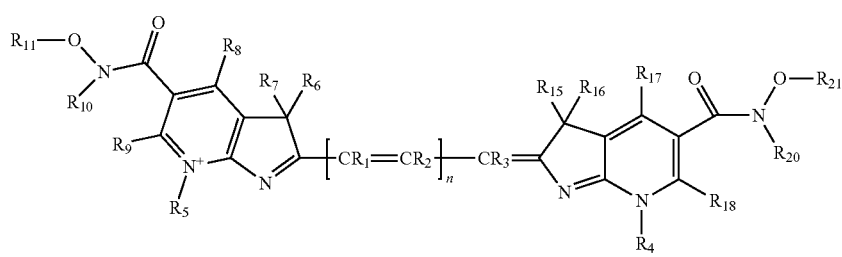

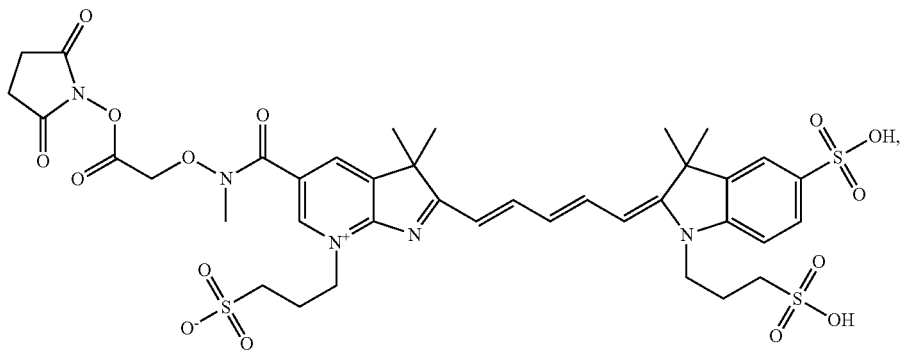
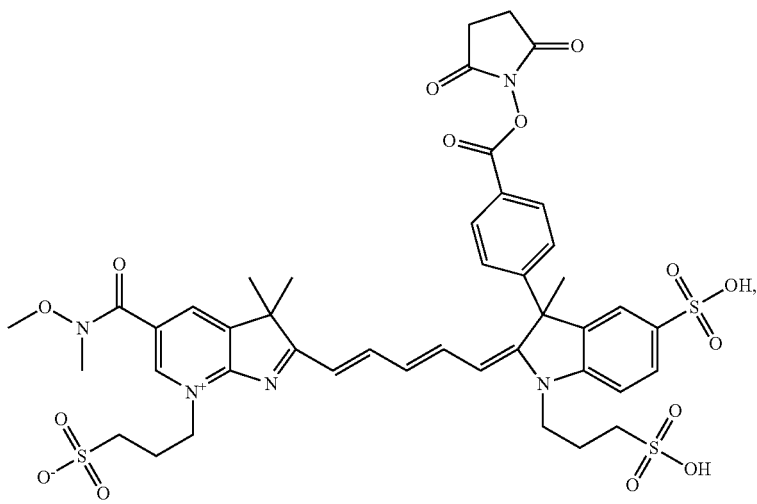
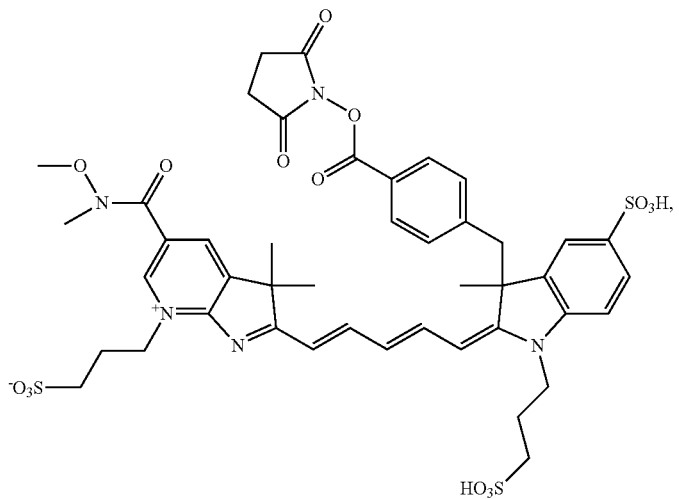

-continued

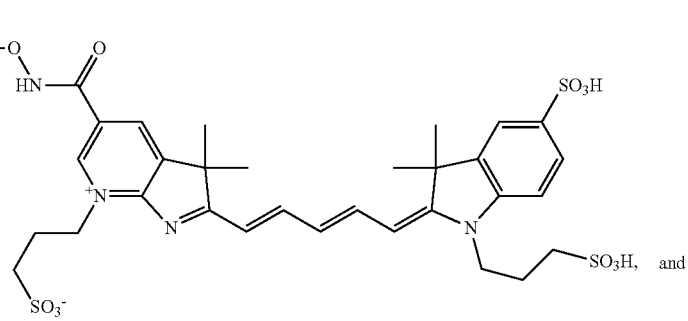

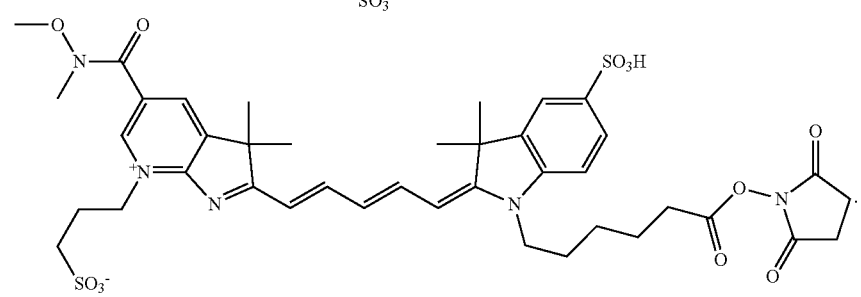

12. A 5-hydroxamate substituted azaindoline-cyanine dye conjugate, comprising: a 5-hydroxamate-azaindoline group linked to a 5-membered heterocylic ring via a divalent polymethine linking group, wherein one or more of the 5-hydroxamate-azaindoline group, the divalent polymethine linking group and the 5-membered heterocylic ring is conjugated to a substrate.

13. The dye conjugate according to claim 12, wherein the dye conjugate is described by Formula VII:

Formula VII

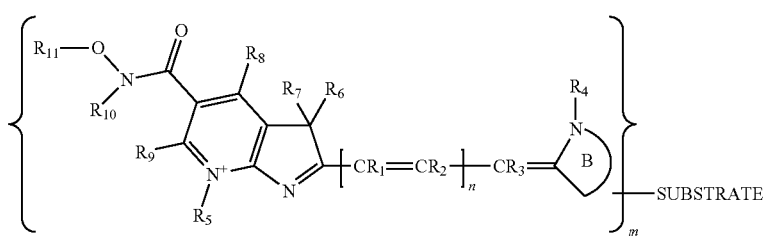

wherein:
ring B represents the atoms necessary to form a nitrogen-containing five-membered heterocyclic ring and further comprises zero to three fused aromatic rings; wherein each atom of the five-membered heterocyclic ring and the zero to three fused aromatic ring is independently selected from the group consisting of C, CH, C(alkyl), C(aryl), O, S, N, N(aryl) and N(alkyl), and the five-membered heterocyclic ring and the zero to three aromatic rings are optionally substituted with one or more substituents selected from the group consisting of a hydrogen, an alkyl having 1-20 carbons, a hydroxy, an alkoxy having 1-20 carbons, a trifluoromethyl, a halogen, a methylthio, a sulfonate, a carbonyl, an amino, a thiol, a phosphonate, and a L-SUBSTRATE;

n is 1 to 3;
m is 1 to 50;
$R_1$-$R_3$ are each independently a hydrogen, a halogen, an alkyl having 1-20 carbons, a cycloalkyl having 3-20 carbons, an aryl, a heteroaryl, an amino, an alkylamino, an arylamino, a thiol, an alkythiol, an arylthiol, a heteroarylthiol, a polyethyleneglycol, an alkoxy, an aryloxy, a carboxyalkyl, or a L-SUBSTRATE;

$R_4$ and $R_5$ are each independently an alkyl having 1-20 carbons, a cycloalkyl having 3-20 carbons, an arylalkyl, a heteroarylalkyl, a carboxyalkyl, or a L-SUBSTRATE;

$R_6$ and $R_7$ are each independently an alkyl having 1-20 carbons, a cycloalkyl having 3-20 carbons, an aryl, an arylalkyl, a heteroaryl, a heteroarylalkyl, a carboxyalkyl, carboxylaryl, or a L-SUBSTRATE;

$R_8$ and $R_9$ are each independently a hydrogen, an alkyl having 1-20 carbons, a hydroxy, an alkoxy having 1-20 carbons, a trifluoromethyl, a halogen, a methylthio, a sulfonate, a carbonyl, an amino, a thiol, a phosphonyl, or a L-SUBSTRATE;

$R_{10}$ and $R_{11}$ are each independently a hydrogen, an alkyl, an aryl, an arylalkyl, a heteroaryl, a heteroarylalkyl, a carboxyalkyl, or a L-SUBSTRATE;

L is a linker between SUBSTRATE and dye; and

SUBSTRATE is a biological molecule.

14. A method of detecting an analyte in a sample, the method comprising:
   a) contacting the sample with a detection reagent comprising a dye-conjugate described by Formula VII under conditions in which the detection reagent forms a complex with the analyte;

arylalkyl, a heteroaryl, a heteroarylalkyl, a carboxyalkyl, a carboxyaryl, or a L-SUBSTRATE;

$R_8$ and $R_9$ are each independently a hydrogen, an alkyl having 1-20 carbons, a hydroxy, an alkoxy having 1-20 carbons, a trifluoromethyl, a halogen, a methylthio, a sulfonate, a carbonyl, an amino, a thiol, a phosphonate, or a L-SUBSTRATE;

$R_{10}$ and $R_{11}$ are each independently a hydrogen, an alkyl, an aryl, an arylalkyl, a heteroaryl, a heteroarylalkyl, a carboxyalkyl, or a L-SUBSTRATE;

L is a linker between SUBSTRATE and dye;
   b) detecting the complex by fluorescence.

15. A method of detecting an analyte in a sample, the method comprising:

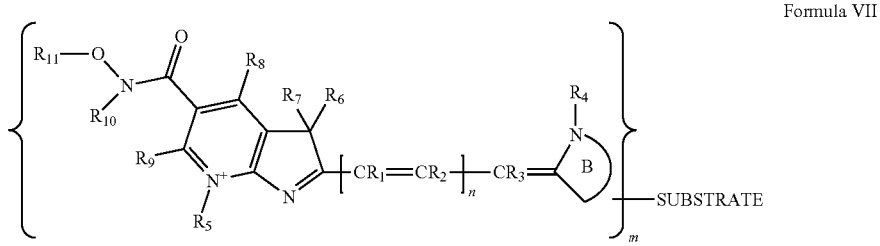

Formula VII wherein:
   ring B represents the atoms necessary to form a nitrogen-containing five-membered heterocyclic ring and further comprises zero to three fused aromatic rings; wherein each atom of the five-membered heterocyclic ring and the zero to three fused aromatic rings is selected from the group consisting of C, CH, C(alkyl), C(aryl), O, S, N, N(aryl) and N(alkyl), and the five-membered heterocyclic ring and the zero to three aromatic rings are optionally substituted with one or more substituents selected from the group consisting of a hydrogen, an alkyl having 1-20 carbons, a hydroxy, an alkoxy having 1-20 carbons, a trifluoromethyl, a halogen, a methylthio, a sulfonate, a carbonyl, an amino, a thiol, a phosphonyl, and a L-SUBSTRATE;

n is 1 to 3;

m is 1 to 50;

$R_1$-$R_3$ are each independently a hydrogen, a halogen, an alkyl having 1-20 carbons, a cycloalkyl having 3-20 carbons, an aryl, a heteroaryl, an amino, an alkylamino, an arylamino, a thiol, an alkylthiol, an arylthiol, a heteroarylthiol, a polyethyleneglycol, an alkoxy, an aryloxy, a carboxyalkyl, or a L-SUBSTRATE;

$R_4$ and $R_5$ are each independently an alkyl having 1-20 carbons, a cycloalkyl having 3-20 carbons, an arylalkyl, a heteroarylalkyl, a carboxyalkyl, or a L-SUBSTRATE;

$R_6$ and $R_7$ are each independently an alkyl having 1-20 carbons, a cycloalkyl having 3-20 carbons, an aryl, an contacting the sample with a 5-hydroxamate substituted azaindoline-cyanine dye compound of claim 1 under conditions sufficient to conjugate the dye to the analyte and produce a labeled analyte conjugate; and detecting the labelled analyte by fluorescence.

16. The method according to claim 15, further comprising separating the labeled analyte from the sample.

17. A kit comprising:
   a 5-hydroxamate substituted azaindoline-cyanine dye compound according to claim 1; and
   one or components selected from a dye conjugates, a substrate, an analyte, a cell, a support, a specific binding moiety, a buffer, a reagent, a light source and instructions for use of reactive dye compounds.

18. A kit comprising:
   a 5-hydroxamate substituted azaindoline-cyanine dye conjugate according to claim 12; and
   one or components selected from a dye compound, a substrate, an analyte, a cell, a support, a specific binding moiety, a buffer, a reagent, a light source and instructions for use of dye conjugates.

19. The kit according to claim 18, wherein the dye conjugate comprises a dye APC conjugate.

* * * * *